(12) United States Patent
Zhou et al.

(10) Patent No.: US 7,884,054 B2
(45) Date of Patent: Feb. 8, 2011

(54) METHODS FOR IDENTIFYING FUNCTIONAL ANTIBODIES

(75) Inventors: Chen Zhou, Thousand Oaks, CA (US); Wenyan Shen, Thousand Oaks, CA (US); Francis H. Martin, Newbury Park, CA (US)

(73) Assignee: Amgen Inc., Thousand Oaks, CA (US)

( * ) Notice: Subject to any disclaimer, the term of this patent is extended or adjusted under 35 U.S.C. 154(b) by 461 days.

(21) Appl. No.: 11/019,027

(22) Filed: Dec. 21, 2004

(65) Prior Publication Data

US 2005/0282181 A1 Dec. 22, 2005

Related U.S. Application Data

(60) Provisional application No. 60/531,714, filed on Dec. 22, 2003, provisional application No. 60/605,902, filed on Aug. 31, 2004.

(51) Int. Cl.
*C12P 21/06* (2006.01)
*C40B 50/06* (2006.01)
*C12N 15/00* (2006.01)
*C12N 5/07* (2010.01)

(52) U.S. Cl. ............ 506/26; 435/69.1; 435/320.1; 435/325

(58) Field of Classification Search ............... None
See application file for complete search history.

(56) References Cited

U.S. PATENT DOCUMENTS

| | | | |
|---|---|---|---|
| 5,654,182 A | 8/1997 | Wahl et al. | |
| 5,677,177 A | 10/1997 | Wahl et al. | |
| 5,885,836 A | 3/1999 | Wahl et al. | |
| 6,706,477 B2 | 3/2004 | Zauderer | |
| 6,800,442 B2 | 10/2004 | Zauderer | |
| 6,830,892 B2 | 12/2004 | Marasco et al. | |
| 2002/0123057 A1* | 9/2002 | Zauderer et al. | 435/6 |
| 2003/0091995 A1 | 5/2003 | Buechler et al. | |
| 2003/0104402 A1 | 6/2003 | Zauderer et al. | |
| 2005/0059082 A1* | 3/2005 | Breitling et al. | 435/7.1 |
| 2005/0196755 A1 | 9/2005 | Zauderer et al. | |

FOREIGN PATENT DOCUMENTS

| | | |
|---|---|---|
| EP | 1 298 207 A1 * | 2/2003 |
| WO | WO 92/15694 | 9/1992 |
| WO | WO 95/20401 | 8/1995 |
| WO | WO 00/55335 | 9/2000 |
| WO | WO 01/25492 A1 | 4/2001 |
| WO | WO 021086096 A2 | 10/2002 |
| WO | WO 02/102855 A2 | 12/2002 |
| WO | WO 03/029456 A1 | 4/2003 |
| WO | WO/2003/029458 A3 * | 10/2003 |
| WO | WO 2005/072112 A2 | 8/2005 |

OTHER PUBLICATIONS

Fukushige and Sauer "Genomic targeting with a positive-selection lox integration vector allows highly reproducible gene expression in mammalian cells", PNAS vol. 89, pp. 7905-7909, Sep. 1992, entire document).*

O'Gorman et al in "Recombinase-mediated gene activation and site-specific integration in mammalian cells" (Science, 1991,vol. 251, pp. 1351-1355).*

Bohn, B., "Flow cytometry: A novel approach for the quantitative analysis of receptor-ligand interactions on surfaces of living cells," *Mol. Cell. Endoctinol.*, 20:1-15, 1980.

Bräuner-Osborne, H. and Brann, M., "Pharmacology of muscarinic acetylcholine receptor subtypes (m1-m5): high throughput assays in mammalian cells," *Eur. J. Pharmacol.*, 295:93-102, 1996.

Davies, J. et al., "Multiple alignment and sorting of peptides derived from phage-displayed random peptide libraries with polyclonal sera allows discrimination of relevant phagotopes," *Mol. Immunol*, 36:659-667, 1999.

Den, W. et al., "A bidirectional phage display vector for the selection and mass transfer of polyclonal antibody libraries," *J. Immunol. Methods*, 222:45-57, 1999.

Embleton, M. et al., "In-cell PCR from mRNA: amplifying and linking the rearranged immunoglobulin heavy and light chain V-genes within single cells," *Nucleic Acids Res.*, 20(15):3831-3837, 1992.

Fredericks, Z. et al., "Identification of potent human anti-IL-1R, antagonist antibodies" *Pro. Eng. Design & Selection*, 17(1):95-106, 2004.

Gao, C. et al., "Making artificial antibodies: A format for phage display of combinatorial heterodimeric arrays," *Proc. Natl. Acad. Sci. USA*, 96:6025-6030, 1999.

Gao, C. et al., "Making chemistry selectable by linking it to infectivity," *Proc. Natl. Acad. Sci. USA*, 94:11777-11782, 1997.

Gao, C. et al., "De novo identification of tumor-specific internalizing human antibody—receptor pairs by phage-display Methods," *J. Immunol. Methods*, 274:185-197, 2003.

Gilliland, L. et al., "Rapid and reliable cloning of antibody variable regions and generation of recombinant single chain antibody fragments," *Tissue Antigens*, 47:1-20, 1996.

(Continued)

*Primary Examiner*—Nancy Vogel
*Assistant Examiner*—Catherine Hibbert
(74) *Attorney, Agent, or Firm*—Rosemary Sweeney

(57) ABSTRACT

The invention provides methods for screening multimeric antibodies produced by mammalian cells to find those that exhibit a biological function. The methods can be used to screen large numbers of antibodies, which may be cell surface, secreted, or intracellular antibodies. Antibodies can be screened to find those that bind antigen more avidly or those that compete with a ligand that binds to the antigen for binding. Any biological function that can be tested in vitro can be used to screen the antibodies. Nucleic acids encoding the antibodies that exhibit the biological function can be obtained in a number of ways.

5 Claims, 18 Drawing Sheets

OTHER PUBLICATIONS

Hoogenboom, H., "Selecting and screening recombinant antibody libraries," *Nature Biotech.*, 23(9):1105-1116, 2005.

Labrijn, A. et al., "Novel strategy for the selection of human recombinant Fab fragments to membrane proteins from a phage-display library," *J. Immunol. Methods*, 261(1-2):37-48, 2002.

Li, S. et al, "Single-chain antibodies against human insulin-like growth factor I receptor: expression, purification, and effect on tumor growth," *Cancer Immunol. Immunother*, 49:243-252, 2000.

Liang, M. et al., "Baculovirus expression cassette vectors for rapid production of complete human IgG from phage display selected antibody fragments," *J. Immunol. Methods*, 247:119-130, 2001.

Mhashilkar, A. et al., "Inhibition of HIV-1 Tat-mediated LTR transactivation and HIV-1 infection by anti-Tat single chain intrabodies," *EMBO J.*, 14(7):1542-1551, 1995.

Müller, K. et al., "A dimeric bispecific miniantibody combines two specificities with avidity," *FEBS Let*. 432:45-49, 1998.

Powers, D. et al., "Expression of single-chain Fv-Fc fusions in *Pichia pastoris*," *J. Immunol. Methods*, 251:123-135, 2001.

Rubera, I. et al., "Specific Cre/Lox recombination in the mouse proximal tubule," *J. Am. Soc. Nephrol*. 15(8):2050-2056, 2004.

Siegel, R. et al., "Recombinatorial cloning using heterologous lox sites," *Genome Res.*, 4(6):1119-1129, 2004.

Sharon, J. et al., "Recombinant polyclonal antibody libraries," *Combinatorial Chem. & High Throughput Screening*, 3(3):185-196, 2000.

Smith, E. et al., "Lethality-based selection of recombinant genes in mammalian cells: Application to identifying tumor antigens," *Nature Med.*, 7(8):967-972, 2001.

Trinh, K. and Morrison, S., "Site-specific and directional gene replacement mediated by Cre recombinase," *J. Immunol. Methods*, 244:185-193, 2000.

Walczak, H. et al., "Trail-R2: a novel apoptosis-mediating receptor for Trail," *EMBO J.*, 16(17):5386-5397, 1997.

Higuchi K. et al., "Cell display library for gene cloning of variable regions of human antibodies to hepatitis B surface antigen," *J Immunol Methods* 202:193-204,1997.

Smith E.S. et al.,"Construction of cDNA libraries in vaccinia virus, " *Methods Mol Biol* 269:65-76, 2004.

Tolonen et al. "Vaccinia Virus DNA Replication Occurs in Endoplasmic Reticulum-enclosed Cytoplasmic Mini-Nuclei, " *Molecular Biology of the Cell*, 2001, vol. 12, pp. 2031-2046.

Wong et al. "Human GM-CSF: Molecular Cloning of the Complementary DNA and Purification of the Natural and Recombinant Proteins, " *Science*, 1985, vol. 228, pp. 810-815.

\* cited by examiner

Clone 14

EVQLVQSGGGKVVQPGGSLRLSCVGSGFMFGRSWMTWVRQAPGKGLEWVA
<u>H1-CDR</u>

NIKQDGSEKHYADSVKGRFTISRDNGKDSLFLEMNSLRSEDTALYYCVR
<u>H2-CDR</u>

EKGYHWFFDLWGRGTLVTVSSGGGGSGGGGSGGGGSAQPVLTQPPSASG
<u>H3-CDR</u>

TPGQRVTISCSGS<span style="border:1px solid">GN</span>KSNIGSNTVNWYRQLPGSAPKLLIFGDDQRPSGVPD
<u>L1-CDR</u>                                                              <u>L2-CDR</u>

RFSGSRSGTSVSLAISGLQSEDEGDYFCAAWDDRLNGGVFGGGTKVTVL
                                       <u>L3-CDR</u>

A.

B.

| Marker | % Gated | Mean |
|---|---|---|
| All | 100.00 | 2.80 |
| M1 | 99.94 | 2.76 |
| M2 | 0.06 | 57.39 |

| Marker | % Gated | Mean |
|---|---|---|
| All | 100.00 | 293.21 |
| M1 | 16.37 | 14.63 |
| M2 | 83.74 | 347.31 |

SEQUENCE LISTING

<160> NUMBER OF SEQ ID NOS: 73

<210> SEQ ID NO 1
<211> LENGTH: 4
<212> TYPE: PRT
<213> ORGANISM: Artificial sequence
<220> FEATURE:
<223> OTHER INFORMATION: ER localization signal

<400> SEQUENCE: 1

Lys Asp Glu Leu
1

<210> SEQ ID NO 2

```
<211> LENGTH: 4
<212> TYPE: PRT
<213> ORGANISM: Artificial sequence
<220> FEATURE:
<223> OTHER INFORMATION: ER localization signal

<400> SEQUENCE: 2

Asp Asp Glu Leu
1

<210> SEQ ID NO 3
<211> LENGTH: 4
<212> TYPE: PRT
<213> ORGANISM: Artificial sequence
<220> FEATURE:
<223> OTHER INFORMATION: ER localization signal

<400> SEQUENCE: 3

Asp Glu Glu Leu
1

<210> SEQ ID NO 4
<211> LENGTH: 4
<212> TYPE: PRT
<213> ORGANISM: Artificial sequence
<220> FEATURE:
<223> OTHER INFORMATION: ER localization signal

<400> SEQUENCE: 4

Asp Lys Glu Leu
1

<210> SEQ ID NO 5
<211> LENGTH: 4
<212> TYPE: PRT
<213> ORGANISM: Artificial sequence
<220> FEATURE:
<223> OTHER INFORMATION: ER localization signal

<400> SEQUENCE: 5

His Asp Glu Leu
1

<210> SEQ ID NO 6
<211> LENGTH: 4
<212> TYPE: PRT
<213> ORGANISM: Artificial sequence
<220> FEATURE:
<223> OTHER INFORMATION: ER localization signal

<400> SEQUENCE: 6

Lys Asp Glu Ile
1

<210> SEQ ID NO 7
<211> LENGTH: 4
<212> TYPE: PRT
<213> ORGANISM: Artificial sequence
<220> FEATURE:
<223> OTHER INFORMATION: ER localization signal

<400> SEQUENCE: 7

Lys Asn Glu Leu
1

<210> SEQ ID NO 8
<211> LENGTH: 4
```

-continued

```
<212> TYPE: PRT
<213> ORGANISM: Artificial sequence
<220> FEATURE:
<223> OTHER INFORMATION: ER localization signal

<400> SEQUENCE: 8

Lys Glu Asp Leu
1

<210> SEQ ID NO 9
<211> LENGTH: 4
<212> TYPE: PRT
<213> ORGANISM: Artificial sequence
<220> FEATURE:
<223> OTHER INFORMATION: ER localization signal

<400> SEQUENCE: 9

Lys Glu Glu Leu
1

<210> SEQ ID NO 10
<211> LENGTH: 4
<212> TYPE: PRT
<213> ORGANISM: Artificial sequence
<220> FEATURE:
<223> OTHER INFORMATION: ER localization signal

<400> SEQUENCE: 10

Lys Asp Asp Leu
1

<210> SEQ ID NO 11
<211> LENGTH: 4
<212> TYPE: PRT
<213> ORGANISM: Artificial sequence
<220> FEATURE:
<223> OTHER INFORMATION: ER localization signal

<400> SEQUENCE: 11

Gln Glu Asp Leu
1

<210> SEQ ID NO 12
<211> LENGTH: 4
<212> TYPE: PRT
<213> ORGANISM: Artificial sequence
<220> FEATURE:
<223> OTHER INFORMATION: ER localization signal

<400> SEQUENCE: 12

Gln Asp Glu Leu
1

<210> SEQ ID NO 13
<211> LENGTH: 4
<212> TYPE: PRT
<213> ORGANISM: Artificial sequence
<220> FEATURE:
<223> OTHER INFORMATION: ER localization signal

<400> SEQUENCE: 13

Gln Glu Glu Leu
1

<210> SEQ ID NO 14
<211> LENGTH: 4
<212> TYPE: PRT
```

```
<213> ORGANISM: Artificial sequence
<220> FEATURE:
<223> OTHER INFORMATION: ER localization signal

<400> SEQUENCE: 14

Arg Asp Glu Leu
1

<210> SEQ ID NO 15
<211> LENGTH: 4
<212> TYPE: PRT
<213> ORGANISM: Artificial sequence
<220> FEATURE:
<223> OTHER INFORMATION: ER localization signal

<400> SEQUENCE: 15

Arg Glu Glu Leu
1

<210> SEQ ID NO 16
<211> LENGTH: 4
<212> TYPE: PRT
<213> ORGANISM: Artificial sequence
<220> FEATURE:
<223> OTHER INFORMATION: ER localization signal

<400> SEQUENCE: 16

Arg Glu Asp Leu
1

<210> SEQ ID NO 17
<211> LENGTH: 4
<212> TYPE: PRT
<213> ORGANISM: Artificial sequence
<220> FEATURE:
<223> OTHER INFORMATION: ER localization signal

<400> SEQUENCE: 17

Arg Asp Asp Leu
1

<210> SEQ ID NO 18
<211> LENGTH: 30
<212> TYPE: PRT
<213> ORGANISM: Rotavirus sp.

<400> SEQUENCE: 18

Gln Asn Tyr Gly Ile Asn Leu Pro Ile Thr Ser Met Asp Thr Ala Tyr
1               5                   10                  15

Ala Asn Ser Thr Gln Glu Glu Thr Phe Leu Thr Ser Thr Leu
            20                  25                  30

<210> SEQ ID NO 19
<211> LENGTH: 5
<212> TYPE: PRT
<213> ORGANISM: Artificial sequence
<220> FEATURE:
<223> OTHER INFORMATION: ER localization signal
<220> FEATURE:
<221> NAME/KEY: MISC_FEATURE
<222> LOCATION: (2)..(2)
<223> OTHER INFORMATION: Xaa can be absent or can be any naturally
      occurring amino acid
<220> FEATURE:
<221> NAME/KEY: misc_feature
<222> LOCATION: (4)..(5)
<223> OTHER INFORMATION: Xaa can be any naturally occurring amino acid
```

```
<400> SEQUENCE: 19

Lys Xaa Lys Xaa Xaa
1               5

<210> SEQ ID NO 20
<211> LENGTH: 5
<212> TYPE: PRT
<213> ORGANISM: Artificial sequence
<220> FEATURE:
<223> OTHER INFORMATION: ER localization signal
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid

<400> SEQUENCE: 20

Arg Xaa Lys Xaa Xaa
1               5

<210> SEQ ID NO 21
<211> LENGTH: 5
<212> TYPE: PRT
<213> ORGANISM: Artificial sequence
<220> FEATURE:
<223> OTHER INFORMATION: ER localization signal
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid

<400> SEQUENCE: 21

Lys Xaa Arg Xaa Xaa
1               5

<210> SEQ ID NO 22
<211> LENGTH: 5
<212> TYPE: PRT
<213> ORGANISM: Artificial sequence
<220> FEATURE:
<223> OTHER INFORMATION: ER localization signal
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid

<400> SEQUENCE: 22

Lys Xaa Lys Xaa Xaa
1               5

<210> SEQ ID NO 23
<211> LENGTH: 5
<212> TYPE: PRT
<213> ORGANISM: Artificial sequence
<220> FEATURE:
<223> OTHER INFORMATION: ER localization signal
<220> FEATURE:
<221> NAME/KEY: misc_feature
<222> LOCATION: (4)..(5)
<223> OTHER INFORMATION: Xaa can be any naturally occurring amino acid
```

```
<400> SEQUENCE: 23

Lys Lys Lys Xaa Xaa
1               5

<210> SEQ ID NO 24
<211> LENGTH: 4
<212> TYPE: PRT
<213> ORGANISM: Artificial sequence
<220> FEATURE:
<223> OTHER INFORMATION: ER localization signal
<220> FEATURE:
<221> NAME/KEY: misc_feature
<222> LOCATION: (3)..(4)
<223> OTHER INFORMATION: Xaa can be any naturally occurring amino acid

<400> SEQUENCE: 24

Arg Lys Xaa Xaa
1

<210> SEQ ID NO 25
<211> LENGTH: 5
<212> TYPE: PRT
<213> ORGANISM: Artificial sequence
<220> FEATURE:
<223> OTHER INFORMATION: ER localization signal
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid

<400> SEQUENCE: 25

Lys Xaa Lys Xaa Xaa
1               5

<210> SEQ ID NO 26
<211> LENGTH: 10
<212> TYPE: PRT
<213> ORGANISM: Artificial sequence
<220> FEATURE:
<223> OTHER INFORMATION: ER localization signal

<400> SEQUENCE: 26

Val Arg Thr Gly Lys Lys Gly Lys Arg Asp
1               5                   10

<210> SEQ ID NO 27
<211> LENGTH: 10
<212> TYPE: PRT
<213> ORGANISM: Human cytomegalovirus

<400> SEQUENCE: 27

Arg Met Ser Gly Asn Phe Thr Glu Lys His
1               5                   10

<210> SEQ ID NO 28
<211> LENGTH: 10
<212> TYPE: PRT
<213> ORGANISM: Artificial sequence
<220> FEATURE:
<223> OTHER INFORMATION: ER localization signal
<220> FEATURE:
<221> NAME/KEY: misc_feature
<222> LOCATION: (1)..(2)
<223> OTHER INFORMATION: Xaa can be any naturally occurring amino acid
```

-continued

```
<220> FEATURE:
<221> NAME/KEY: misc_feature
<222> LOCATION: (4)..(7)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid

<400> SEQUENCE: 28

Xaa Xaa Ser Xaa Xaa Xaa Xaa Glu Lys Xaa
1               5                   10

<210> SEQ ID NO 29
<211> LENGTH: 35
<212> TYPE: PRT
<213> ORGANISM: Rubella virus type I

<400> SEQUENCE: 29

Trp Trp Asn Leu Thr Leu Gly Ala Ile Cys Ala Leu Pro Leu Val Gly
1               5                   10                  15

Leu Leu Ala Cys Cys Ala Lys Cys Leu Tyr Tyr Leu Arg Gly Ala Ile
            20                  25                  30

Ala Pro Arg
        35

<210> SEQ ID NO 30
<211> LENGTH: 24
<212> TYPE: PRT
<213> ORGANISM: Rattus norvegicus

<400> SEQUENCE: 30

Lys Gln Phe Asn Lys Gly Arg Leu Gln Leu Leu Leu Leu Val Cys Leu
1               5                   10                  15

Val Ala Val Ala Ala Val Ile Val
            20

<210> SEQ ID NO 31
<211> LENGTH: 32
<212> TYPE: PRT
<213> ORGANISM: Rattus norvegicus

<400> SEQUENCE: 31

Trp Ser Lys Phe Phe Leu Leu Asn Lys Gly Arg Leu Gln Leu Leu Leu
1               5                   10                  15

Leu Val Cys Leu Val Ala Val Ala Ala Val Ile Val Lys Asp Gln Leu
            20                  25                  30

<210> SEQ ID NO 32
<211> LENGTH: 27
<212> TYPE: PRT
<213> ORGANISM: Rattus norvegicus

<400> SEQUENCE: 32

Trp Ser Lys Phe Phe Leu Leu Lys Gln Arg Leu Gln Leu Leu Leu Leu
1               5                   10                  15

Val Cys Leu Val Ala Val Ala Ala Val Ile Val
            20                  25

<210> SEQ ID NO 33
<211> LENGTH: 20
<212> TYPE: PRT
<213> ORGANISM: Saccharomyces cerevisiae
```

-continued

```
<400> SEQUENCE: 33

Ser Arg Phe Phe Thr Asn Phe Ile Leu Val Leu Leu Ser Tyr Ile Leu
1               5                   10                  15

Gln Phe Ser Leu
            20

<210> SEQ ID NO 34
<211> LENGTH: 12
<212> TYPE: PRT
<213> ORGANISM: Homo sapiens

<400> SEQUENCE: 34

Ala Glu Glu Gln Lys Leu Ile Ser Glu Glu Asp Leu
1               5                   10

<210> SEQ ID NO 35
<211> LENGTH: 20
<212> TYPE: PRT
<213> ORGANISM: Homo sapiens
<220> FEATURE:
<221> NAME/KEY: SIGNAL
<222> LOCATION: (1)..(20)
<223> OTHER INFORMATION: Signal peptide

<400> SEQUENCE: 35

Met Glu Thr Asp Thr Leu Leu Leu Trp Val Leu Leu Leu Trp Val Pro
1               5                   10                  15

Gly Ser Thr Gly
            20

<210> SEQ ID NO 36
<211> LENGTH: 26
<212> TYPE: PRT
<213> ORGANISM: Homo sapiens
<220> FEATURE:
<221> NAME/KEY: SIGNAL
<222> LOCATION: (1)..(26)
<223> OTHER INFORMATION: Signal peptide

<400> SEQUENCE: 36

Met Ala Thr Gly Ser Arg Thr Ser Leu Leu Leu Ala Phe Gly Leu Leu
1               5                   10                  15

Cys Leu Pro Trp Leu Gln Glu Gly Ser Ala
            20                  25

<210> SEQ ID NO 37
<211> LENGTH: 22
<212> TYPE: PRT
<213> ORGANISM: Artificial sequence
<220> FEATURE:
<223> OTHER INFORMATION: His tag

<400> SEQUENCE: 37

Arg Ser Gly Ser Ser Asp Tyr Lys Asp Asp Asp Lys Gly Ser Ser
1               5                   10                  15

His His His His His His
            20

<210> SEQ ID NO 38
<211> LENGTH: 22
<212> TYPE: DNA
<213> ORGANISM: Artificial sequence
<220> FEATURE:
<223> OTHER INFORMATION: Oligonucleotide
```

-continued

```
<400> SEQUENCE: 38
ctagctagcc aggtgcagct gg                                              22

<210> SEQ ID NO 39
<211> LENGTH: 22
<212> TYPE: DNA
<213> ORGANISM: Artificial sequence
<220> FEATURE:
<223> OTHER INFORMATION: Oligonucleotide

<400> SEQUENCE: 39
ctagctagcg aggtgcagct gg                                              22

<210> SEQ ID NO 40
<211> LENGTH: 22
<212> TYPE: DNA
<213> ORGANISM: Artificial sequence
<220> FEATURE:
<223> OTHER INFORMATION: Oligonucleotide

<400> SEQUENCE: 40
ctagctagcc aggtccagct gg                                              22

<210> SEQ ID NO 41
<211> LENGTH: 25
<212> TYPE: DNA
<213> ORGANISM: Artificial sequence
<220> FEATURE:
<223> OTHER INFORMATION: Oligonucleotide

<400> SEQUENCE: 41
ctagctagcg aggtgcagct gttgg                                           25

<210> SEQ ID NO 42
<211> LENGTH: 22
<212> TYPE: DNA
<213> ORGANISM: Artificial sequence
<220> FEATURE:
<223> OTHER INFORMATION: Oligonucleotide

<400> SEQUENCE: 42
ctagctagcc aggtgcagct gc                                              22

<210> SEQ ID NO 43
<211> LENGTH: 19
<212> TYPE: DNA
<213> ORGANISM: Artificial sequence
<220> FEATURE:
<223> OTHER INFORMATION: Oligonucleotide

<400> SEQUENCE: 43
ctagctgctg aggagacgg                                                  19

<210> SEQ ID NO 44
<211> LENGTH: 21
<212> TYPE: DNA
<213> ORGANISM: Artificial sequence
<220> FEATURE:
<223> OTHER INFORMATION: Oligonucleotide

<400> SEQUENCE: 44
ctagctagct gaagagacgg t                                               21

<210> SEQ ID NO 45
<211> LENGTH: 20
```

```
<212> TYPE: DNA
<213> ORGANISM: Artificial sequence
<220> FEATURE:
<223> OTHER INFORMATION: Oligonucleotide

<400> SEQUENCE: 45
ctagctagca ctcgagacgg                                              20

<210> SEQ ID NO 46
<211> LENGTH: 21
<212> TYPE: DNA
<213> ORGANISM: Artificial sequence
<220> FEATURE:
<223> OTHER INFORMATION: Oligonucleotide

<400> SEQUENCE: 46
ctagctagcg aaattgtgtt g                                            21

<210> SEQ ID NO 47
<211> LENGTH: 21
<212> TYPE: DNA
<213> ORGANISM: Artificial sequence
<220> FEATURE:
<223> OTHER INFORMATION: Oligonucleotide

<400> SEQUENCE: 47
ctagctagcc agcctgtgct g                                            21

<210> SEQ ID NO 48
<211> LENGTH: 21
<212> TYPE: DNA
<213> ORGANISM: Artificial sequence
<220> FEATURE:
<223> OTHER INFORMATION: Oligonucleotide

<400> SEQUENCE: 48
ctagctagcc aggctgtgct g                                            21

<210> SEQ ID NO 49
<211> LENGTH: 21
<212> TYPE: DNA
<213> ORGANISM: Artificial sequence
<220> FEATURE:
<223> OTHER INFORMATION: Oligonucleotide

<400> SEQUENCE: 49
ctagctagcc agtctgccct g                                            21

<210> SEQ ID NO 50
<211> LENGTH: 21
<212> TYPE: DNA
<213> ORGANISM: Artificial sequence
<220> FEATURE:
<223> OTHER INFORMATION: Oligonucleotide

<400> SEQUENCE: 50
ctagctagct cttctgagct g                                            21

<210> SEQ ID NO 51
<211> LENGTH: 23
<212> TYPE: DNA
<213> ORGANISM: Artificial sequence
<220> FEATURE:
<223> OTHER INFORMATION: Oligonucleotide

<400> SEQUENCE: 51
```

-continued

```
ctagctagcc agtctgtgct gac                                              23

<210> SEQ ID NO 52
<211> LENGTH: 21
<212> TYPE: DNA
<213> ORGANISM: Artificial sequence
<220> FEATURE:
<223> OTHER INFORMATION: Oligonucleotide

<400> SEQUENCE: 52
ctagctagct cgtctgagct g                                                21

<210> SEQ ID NO 53
<211> LENGTH: 24
<212> TYPE: DNA
<213> ORGANISM: Artificial sequence
<220> FEATURE:
<223> OTHER INFORMATION: Oligonucleotide

<400> SEQUENCE: 53
ctacgtacgt ttaatctcca gtcg                                             24

<210> SEQ ID NO 54
<211> LENGTH: 21
<212> TYPE: DNA
<213> ORGANISM: Artificial sequence
<220> FEATURE:
<223> OTHER INFORMATION: Oligonucleotide

<400> SEQUENCE: 54
ctacgtacgt aaaacggtga g                                                21

<210> SEQ ID NO 55
<211> LENGTH: 21
<212> TYPE: DNA
<213> ORGANISM: Artificial sequence
<220> FEATURE:
<223> OTHER INFORMATION: Oligonucleotide

<400> SEQUENCE: 55
ctacgtacgt aggacagtca g                                                21

<210> SEQ ID NO 56
<211> LENGTH: 21
<212> TYPE: DNA
<213> ORGANISM: Artificial sequence
<220> FEATURE:
<223> OTHER INFORMATION: Oligonucleotide

<400> SEQUENCE: 56
ctacgtacgt aggacggtga c                                                21

<210> SEQ ID NO 57
<211> LENGTH: 21
<212> TYPE: DNA
<213> ORGANISM: Artificial sequence
<220> FEATURE:
<223> OTHER INFORMATION: Oligonucleotide

<400> SEQUENCE: 57
ctacgtacgt aggacggtca g                                                21

<210> SEQ ID NO 58
<211> LENGTH: 6
<212> TYPE: PRT
<213> ORGANISM: Artificial sequence
```

```
<220> FEATURE:
<223> OTHER INFORMATION: ER localization signal

<400> SEQUENCE: 58

Ser Glu Lys Asp Glu Leu
1               5

<210> SEQ ID NO 59
<211> LENGTH: 44
<212> TYPE: DNA
<213> ORGANISM: Artificial sequence
<220> FEATURE:
<223> OTHER INFORMATION: Oligonucleotide

<400> SEQUENCE: 59
cagcagaagc ttctagacca ccatgcgtac tctggctatc cttg                    44

<210> SEQ ID NO 60
<211> LENGTH: 21
<212> TYPE: DNA
<213> ORGANISM: Artificial sequence
<220> FEATURE:
<223> OTHER INFORMATION: Oligonucleotide

<400> SEQUENCE: 60
aagaccgatg ggcccttggt g                                             21

<210> SEQ ID NO 61
<211> LENGTH: 49
<212> TYPE: DNA
<213> ORGANISM: Artificial sequence
<220> FEATURE:
<223> OTHER INFORMATION: Oligonucleotide

<400> SEQUENCE: 61
cagcagaagc ttctagacca ccatgaaaat cctgattctc ggtatcttc               49

<210> SEQ ID NO 62
<211> LENGTH: 34
<212> TYPE: DNA
<213> ORGANISM: Artificial sequence
<220> FEATURE:
<223> OTHER INFORMATION: Oligonucleotide

<400> SEQUENCE: 62
cttgtcgact caacactctc ccctgttgaa gctc                               34

<210> SEQ ID NO 63
<211> LENGTH: 44
<212> TYPE: DNA
<213> ORGANISM: Artificial sequence
<220> FEATURE:
<223> OTHER INFORMATION: Oligonucleotide

<400> SEQUENCE: 63
cagcagaagc ttctagacca ccatgcgtac tctggctatc cttg                    44

<210> SEQ ID NO 64
<211> LENGTH: 28
<212> TYPE: DNA
<213> ORGANISM: Artificial sequence
<220> FEATURE:
<223> OTHER INFORMATION: Oligonucleotide

<400> SEQUENCE: 64
ttatcaggat cctttacccg gagacagg                                      28
```

<210> SEQ ID NO 65
<211> LENGTH: 47
<212> TYPE: DNA
<213> ORGANISM: Artificial sequence
<220> FEATURE:
<223> OTHER INFORMATION: Oligonucleotide

<400> SEQUENCE: 65
cagcagatcg atagaccacc atgaaaatcc tgattctcgg tatcttc                  47

<210> SEQ ID NO 66
<211> LENGTH: 37
<212> TYPE: DNA
<213> ORGANISM: Artificial sequence
<220> FEATURE:
<223> OTHER INFORMATION: Oligonucleotide

<400> SEQUENCE: 66
cttcttctcg agtcaacact ctccctgtt gaagctc                              37

<210> SEQ ID NO 67
<211> LENGTH: 47
<212> TYPE: DNA
<213> ORGANISM: Artificial sequence
<220> FEATURE:
<223> OTHER INFORMATION: Oligonucleotide

<400> SEQUENCE: 67
cagcagatcg atagaccacc atgaaaatcc tgattctcgg tatcttc                  47

<210> SEQ ID NO 68
<211> LENGTH: 37
<212> TYPE: DNA
<213> ORGANISM: Artificial sequence
<220> FEATURE:
<223> OTHER INFORMATION: Oligonucleotide

<400> SEQUENCE: 68
cttcttctcg agtcaacact ctccctgtt gaagctc                              37

<210> SEQ ID NO 69
<211> LENGTH: 47
<212> TYPE: DNA
<213> ORGANISM: Artificial sequence
<220> FEATURE:
<223> OTHER INFORMATION: Oligonucleotide

<400> SEQUENCE: 69
acttaagctt cgtctctagt ccaccatgcg tactctggct atccttg                  47

<210> SEQ ID NO 70
<211> LENGTH: 33
<212> TYPE: DNA
<213> ORGANISM: Artificial sequence
<220> FEATURE:
<223> OTHER INFORMATION: Oligonucleotide

<400> SEQUENCE: 70
accgatgggc ccttggtgct agctgaggag acg                                 33

<210> SEQ ID NO 71
<211> LENGTH: 53
<212> TYPE: DNA
<213> ORGANISM: Artificial sequence
<220> FEATURE:

<223> OTHER INFORMATION: Oligonucleotide

<400> SEQUENCE: 71
cagcagccac ctgattggag accaccatga aatcctgat tctcggtatc ttc     53

<210> SEQ ID NO 72
<211> LENGTH: 43
<212> TYPE: DNA
<213> ORGANISM: Artificial sequence
<220> FEATURE:
<223> OTHER INFORMATION: Oligonucleotide

<400> SEQUENCE: 72
cttcttccag agtcatggtc aacactctcc cctgttgaag ctc     43

<210> SEQ ID NO 73
<211> LENGTH: 245
<212> TYPE: PRT
<213> ORGANISM: Artificial sequence
<220> FEATURE:
<223> OTHER INFORMATION: scFv

<400> SEQUENCE: 73

```
Glu Val Gln Leu Val Gln Ser Gly Gly Lys Val Val Gln Pro Gly Gly
1               5                   10                  15
Ser Leu Arg Leu Ser Cys Val Gly Ser Gly Phe Met Phe Gly Arg Ser
            20                  25                  30
Trp Met Thr Trp Val Arg Gln Ala Pro Gly Lys Gly Leu Glu Trp Val
        35                  40                  45
Ala Asn Ile Lys Gln Asp Gly Ser Glu Lys His Tyr Ala Asp Ser Val
    50                  55                  60
Lys Gly Arg Phe Thr Ile Ser Arg Asp Asn Gly Lys Asp Ser Leu Phe
65                  70                  75                  80
Leu Glu Met Asn Ser Leu Arg Ser Glu Asp Thr Ala Leu Tyr Tyr Cys
                85                  90                  95
Val Arg Glu Lys Gly Tyr His Trp Phe Phe Asp Leu Trp Gly Arg Gly
            100                 105                 110
Thr Leu Val Thr Val Ser Ser Gly Gly Gly Ser Gly Gly Gly Gly
        115                 120                 125
Ser Gly Gly Gly Gly Ser Ala Gln Pro Val Leu Thr Gln Pro Pro Ser
    130                 135                 140
Ala Ser Gly Thr Pro Gly Gln Arg Val Thr Ile Ser Cys Ser Gly Asn
145                 150                 155                 160
Lys Ser Asn Ile Gly Ser Asn Thr Val Asn Trp Tyr Arg Gln Leu Pro
                165                 170                 175
Gly Ser Ala Pro Lys Leu Leu Ile Phe Gly Asp Asp Gln Arg Pro Ser
            180                 185                 190
Gly Val Pro Asp Arg Phe Ser Gly Ser Arg Ser Gly Thr Ser Val Ser
        195                 200                 205
Leu Ala Ile Ser Gly Leu Gln Ser Glu Asp Glu Gly Asp Tyr Phe Cys
    210                 215                 220
Ala Ala Trp Asp Asp Arg Leu Asn Gly Gly Val Phe Gly Gly Gly Thr
225                 230                 235                 240
Lys Val Thr Val Leu
                245
```

METHODS FOR IDENTIFYING FUNCTIONAL ANTIBODIES

This application claims benefit of U.S. Provisional Application Nos. 60/531,714, filed Dec. 22, 2003, and 60/605,902, filed Aug. 31, 2004, both of which are hereby incorporated by reference in their entirety.

FIELD

This invention is a method of screening and/or selecting for proteins, particularly antibodies, that are produced by mammalian cells and that have a chosen biological function.

BACKGROUND

Antibodies continue to be developed as therapeutics for a variety of indications. Current methods of screening groups of antibodies typically focus on selecting for antibodies that bind to known proteins. Such selections can yield a large number of antibodies, few of which have therapeutically useful biological properties. Moreover, such antibodies are typically expressed as Fab or scFv fragments in prokaryotic or yeast systems. Most currently approved antibody therapeutics are, full-length antibodies, often human or humanized antibodies, that are usually expressed in mammalian cells. Therefore, development of therapeutic antibodies from libraries of antibodies typically involves a tedious, one-by-one conversion of selected antibody fragments to full-length antibodies. Subsequent testing of the full-length antibodies does not always yield results that correlate well with results obtained with the antibody fragments. The present invention presents a scheme for subjecting a moderately large group of multimeric, optionally Fc-containing, antibodies expressed by mammalian cells to a screen or a selection to directly identify antibodies that have a desired biological property.

SUMMARY

In the broadest sense, the invention provides methods for directly screening and/or selecting for multimeric antibodies produced by mammalian cells and having at least one biological function. For example, the invention encompasses a method for enriching for nucleic acids encoding multimeric antibodies having a biological function comprising the steps of: (a) transfecting mammalian cells with polynucleotides containing a library of nucleic acids encoding multimeric antibodies and a vector, thereby creating transfectants, wherein the transfectants express at least about 100 different antibodies and wherein the polynucleotides containing the library are isolated from host cells; (b) testing the antibodies produced by the transfectants for the biological function, thereby identifying antibodies or groups of antibodies that have the biological function; and (c) obtaining polynucleotides encoding the identified antibodies from the transfectants or from the polynucleotides containing the library.

In one embodiment, the invention encompasses a method for enriching for mammalian cells expressing recombinant, multimeric antibodies, optionally Fc-containing antibodies, that bind to an antigen comprising the steps of: (a) introducing a library of nucleic acids in a first vector encoding a group of recombinant, multimeric antibodies into mammalian cells, thereby creating a group of recombinant antibodies displayed on the cell surfaces of a group of mammalian cells, wherein most of the mammalian cells each express only recombinant multimeric antibodies with amino acid sequences that are the same as those of other recombinant, multimeric antibodies expressed on the surface of the same cell, and wherein, as a group, the mammalian cells express at least about 10 different recombinant antibodies; (b) providing an antigen; and (c) isolating the mammalian cells that bind to the antigen. The mammalian cells may have been transfected with nucleic acids encoding FLP recombinase and with the library encoding the group of antibodies carried on the first vector, wherein the first vector may comprise an FRT site, and the mammalian cells may each comprise an FRT site. The antigen may have at least one known counterstructure. The method can further comprise combining the mammalian cells displaying the multimeric antibodies with the known counterstructure and the antigen; and isolating the mammalian cells that do not bind to the antigen in the presence of the known counterstructure. The antigen can be fluorescently and/or luminescently labeled or biotinylated. The mammalian cells that bind to the labeled antigen can be isolated by fluorescence-activated cell sorting (FACS) or using magnetic beads coated with streptavidin, among many possible methods. The method can also include (1) recovering nucleic acids from the mammalian cells of (c), (2) amplifying nucleic acids encoding at least one antibody variable region from the nucleic acids, (3) inserting the amplified nucleic acids into a second vector, wherein the second vector with the inserted nucleic acids encodes a secreted, soluble antibody that can be expressed by a mammalian cell, (4) transforming a host cell with the second vector with the inserted nucleic acids, (5) picking host cell colonies and using recombinant DNA obtained therefrom or copies thereof to transfect mammalian cells, and (6) isolating transfectants or groups of transfectants that express secreted soluble antibodies that can bind to the antigen. The antibody can be an scFv-Fc or a full-length antibody.

In another aspect, the invention encompasses a method for enriching for multimeric, optionally Fc-containing, antibodies having a biological function comprising the steps of: (a) contacting phage displaying a group of antibodies, which may be scFv's or Fab fragments, with an antigen; (b) recovering the group of phage expressing antibodies that bind to the antigen; (c) obtaining nucleic acids from the group of phage of (b); (d) inserting a portion of the nucleic acids of (c) or a copy thereof encoding at least an antibody variable region into a vector, wherein the vector comprises nucleic acids encoding a multimerizing domain, such as an Fc region of an antibody, and sequences allowing the expression of the antibody encoded by the vector plus the inserted nucleic acids in a mammalian cell; (e) introducing the vector plus inserted nucleic acids of (d) into a host cell via transformation, thereby creating transformants; (f) isolating recombinant nucleic acids from the transformants; (g) transfecting mammalian cells with the recombinant nucleic acids from the transformants of (f), thereby creating transfectants, wherein the transfectants express at least about 10, optionally at least about $10^2$, $10^3$, $10^4$, $10^5$, or $10^6$, different antibodies; (h) separating the mammalian cells into pools comprising at least one cell either before, after, or during transfection; (i) individually combining the pools, or medium in which the pools have been cultured, with mammalian target cells that can exhibit the biological function; and (j) testing for the biological function, thereby identifying pools expressing antibodies that have the biological function. Most individual transfectants may express antibodies with a single sequence. The host cells for transformation can be *E. coli* cells, and the antigen can be a first kind of mammalian cells or a protein. The method may further comprise contacting the phage displaying the group of antibodies with a second kind of mammalian cells, and recovering the group of phage that do not bind to the second kind of mammalian cells. The vector can comprise nucleic acids encoding a membrane association sequence, and the pools of mammalian transfectants can be combined with the mammalian target cells in step (i). The antibodies produced by the transfectants can be secreted, soluble antibodies, and the medium in which the pools have been cultured can be combined with the mammalian target cells in step (i). Transformants of (e) can be combined into pools of not more than about 1000, 500, 400, 300, 200, 100, 50, or 20 transformants, and nucleic acids from these pools can be used to transfect the mammalian cells in step (g), wherein the mammalian cells are separated into pools before transfection, whereby pools of mammalian transfectants corresponding to the pools of transformants are created. The biological function can include something other than binding to an antigen. The biological function may be proliferation or caspase activity of cancer cells.

In another embodiment, the invention comprises a method for enriching for nucleic acids encoding multimeric antibodies having a biological function comprising the steps of: (a) introducing a library of nucleic acids that encodes a group of multimeric antibodies in a vector into a host cell via transformation, thereby creating transformants; (b) isolating recombinant nucleic acids from the individual transformants and/or progeny thereof or from groups of transformants and/or progeny thereof, thereby producing plural pools of nucleic acids encoding multimeric antibodies; (c) transfecting mammalian cells with the pools of recombinant nucleic acids of (b), thereby creating pools of transfectants, wherein the pools transfectants taken together express at least about 100 different multimeric antibodies; (d) combining the pools of transfectants, or antibodies produced by the pools of transfectants, with mammalian target cells that can exhibit the biological function; and (e) testing for the biological function, thereby identifying pools of transfectants expressing antibodies that have the biological function; and (f) recovering nucleic acids encoding antibodies expressed by the identified pools of transfectants from the pools of nucleic acids of (b). The transfectants may express at least about 1000, 10,000, or 100,000 different antibodies, and individual transfectants may express only multimeric antibodies having identical amino acid sequences. The host cell can be an $E.\ coli$ cell. The antigen can be a first kind of mammalian cells or a protein. The method can further comprise the following steps prior to step (a): contacting phage displaying a group of antibodies with an antigen; recovering a group of phage expressing antibodies that bind to the antigen; obtaining nucleic acids from the group of phage; inserting a portion of the nucleic acids from the group of phage and/or a copy thereof encoding at least an antibody variable region into the vector, wherein the vector comprises nucleic acids encoding a multimerizing domain and sequences allowing the expression of the antibody encoded by the vector plus the inserted nucleic acids in a mammalian cell. The antibodies produced by the transfectants can be secreted, soluble antibodies, cell surface antibodies, or intracellular antibodies, can comprise an Fc region, and can be scFv-Fcs or full length antibodies. Transformants can be combined into pools of not more than about 100 or about 50 transformants, wherein nucleic acids from these pools are used to transfect the mammalian cells in step (c), and wherein the mammalian cells are separated into pools before transfection, whereby pools of mammalian transfectants corresponding to the pools of transformants are created. The biological function can include something other than or in addition to binding to an antigen and may be, for example, caspase activity, apoptosis, and/or inhibition of proliferation of cancer cells.

In still another embodiment the invention includes method for identifying mammalian cells expressing multimeric, optionally Fc-containing, antibodies having a biological function comprising the steps of: (a) contacting phage displaying a group of antibodies with an antigen; (b) recovering the phage that bind to the antigen; (c) obtaining nucleic acids from the recovered phage; (d) inserting a portion of the nucleic acids of (c) or a copy thereof encoding at least an antibody variable region into a vector, wherein the vector comprises nucleic acids encoding a multimerizing domain, optionally an Fc region of an antibody, an intracellular localization sequence and/or a membrane association sequence, and sequences allowing the expression of the multimeric antibody encoded by the vector plus the inserted nucleic acids in a mammalian cell; (e) introducing the vector plus inserted nucleic acids of (d) or a copy thereof into suitable host cells for transformation, thereby creating transformants; (f) isolating recombinant nucleic acids from the transformants; (g) introducing the nucleic acids of (f) or a copy thereof into mammalian cells, thereby creating transfectants, wherein the transfectants express at least 10, optionally at least about $10^2$, $10^3$, $10^4$, $10^5$, or $10^6$, different antibodies; and (h) testing the transfectants and/or progeny thereof and/or medium in which they have been cultured for the biological function, thereby identifying transfectants or groups of transfectants that express antibodies that exhibit the biological function. The host cells for transformation can be $E.\ coli$ cells, and the transformants of step (e) can be combined into pools of not more than about 20, 30, 40, 50, 60, 80, 100, 120, 160, 200, 400, 600, or 1000 transformants. The nucleic acids from these pools can be introduced into the mammalian cells in step (g), wherein the mammalian cells are separated into pools before transfection, whereby pools of mammalian transfectants corresponding to the pools of transformants are created. The antigen can be a first kind of mammalian cells or a protein. The antibodies may be scFv-Fcs or full-length antibodies. The vector can comprise sequences derived from a lentivirus, and the method may further comprise the step of packaging the vector with the inserted sequence of step (d) into viral particles prior to step (g). The biological function tested for can include a property other than antigen binding.

The invention further includes a method for enriching for nucleic acids encoding multimeric antibodies having a biological function comprising the steps of: (a) transfecting mammalian cells with a vector comprising nucleic acids encoding multimeric antibodies, thereby creating transfectants, wherein the transfectants express at least about 50 or 100 different antibodies and wherein the vector comprising nucleic acids encoding multimeric antibodies is isolated from host cells; (b) testing the antibodies produced by the transfectants for the biological function, thereby identifying antibodies or groups of antibodies that have the biological function; and (c) obtaining nucleic acids encoding the identified antibodies from the transfected mammalian cells or from the bacterial nucleic acids used to transfect the mammalian cells. The transfectants may express at least about 1000, 10,000, or 100,000 different antibodies. Most individual transfectants may express one or more molecules of one multimeric antibody. The method can further comprise: contacting phage displaying a group of antibodies with an antigen; recovering a group of phage that is enriched for phage expressing antibodies that bind to the antigen; obtaining nucleic acids from the group of phage; inserting a portion of the nucleic acids and/or a copy thereof encoding at least an antibody variable region into the vector, thereby creating the vector comprising nucleic acids encoding multimeric antibodies; introducing the vector into a bacterial host cell via transformation, thereby creating transformants; and isolating the vector comprising nucleic acids encoding multimeric antibodies from the transformants and/or progeny thereof. The antigen can be a protein or a kind of mammalian cells. The antibodies produced by the transfectants can be secreted, soluble antibodies. The antibodies can comprise an Fc region and may be scFv-Fcs or full-length antibodies. The transformants may be combined into pools of not more than about 100 or about 50 transformants, and nucleic acids from these pools may be used to transfect the mammalian cells. The mammalian cells may be separated into pools before transfection, whereby pools of mammalian transfectants corresponding to the pools of transformants are created. The biological function may be caspase activity, apoptosis, and/or inhibition of proliferation of cancer cells. The biological function may be something other than or in addition to binding to an antigen.

In a further aspect, the invention includes a method for identifying transfectants expressing multimeric antibodies having a biological function comprising the steps of: (a) transfecting mammalian cells with one or more vectors comprising nucleic acids encoding full length antibodies, thereby creating transfectants, wherein the transfectants express at least about 50 or 100 different antibodies, wherein the vector does not comprise vaccinia virus sequence; and (b) testing the antibodies produced by the transfectants for the biological function, thereby identifying transfectants or groups of transfectants expressing antibodies that have the biological function. The biological function may be something other than or in addition to binding to an antigen.

In still another aspect, the invention encompasses a method for identifying mammalian transfectants expressing scFv-Fcs having a biological function comprising: providing a group of at least about 10, 50, 100, 1000, 10,000, 100,000, or 1,000,000 scFv-Fcs expressed on the surface of a group mammalian cells; separating the mammalian cells into pools comprising at least one cell; testing the pools for the biological function; and recovering pools that exhibit the biological function. The biological function tested for can include a property other than antigen binding.

In still another aspect, the invention includes a method for enriching for mammalian cells expressing scFv-Fcs having a biological function comprising: providing a group of mammalian cells that express and secrete a group of at least about 10, 100, 1000, 10,000, 100,000, or 1,000,000 different scFv-Fcs, wherein most individual mammalian cells in the group express scFv-Fcs with a single sequence; separating the mammalian cells into pools comprising at least one cell; testing the medium in which the pools are cultured for the biological function; and recovering pools that express antibodies that exhibit the biological function. The biological function can includes a property other than antigen binding.

The invention also encompasses a method for identifying mammalian transfectants expressing scFv-Fcs having a biological function comprising: transfecting one or more groups of mammalian cells with nucleic acids encoding at least about 10, 50, 100, 1000, 10,000, or 100,000 different scFv-Fcs, thereby creating transfectants or groups of transfectants which, taken together, express at least about 10, 50, 100, 1000, 10,000, or 100,000 different scFv-Fcs; and testing the transfectants for the biological function, thereby identifying transfectants or groups of transfectants expressing scFv-Fcs that exhibit the biological function. The transfectants may be separated into pools comprising plural transfectants, and the biological function tested for may include a property other than or in addition to antigen binding. Most individual transfectants may express only one kind of scFv-Fc on their cell surface.

In still another embodiment, the invention comprises a method for identifying mammalian cells expressing scFv-Fcs having a biological function comprising: separating a group of mammalian cells into pools comprising at least about one cell either before, during, or after transfection with nucleic acids encoding scFv-Fcs, wherein, as a group, after transfection, the mammalian cells express and secrete a group of at least about 10, 50, 100, 1000, 10,000, or 100,000 different scFv-Fcs; and testing the scFv-Fcs for the biological function, thereby identifying pools of cells expressing scFv-Fcs that exhibit the biological function. The mammalian cells may be separated into pools comprising plural cells, and the biological function may include a property other than or in addition to antigen binding.

The invention also provides a method for enriching for variant proteins that bind to a molecule with different affinity than does an original protein that binds to the molecule comprising the steps of: (a) providing a first nucleic acid that encodes the original protein, wherein the original protein can be expressed from the nucleic acid as a cell surface protein; (b) providing a library of nucleic acids that encodes variant proteins, wherein the variant proteins are identical in sequence to the original protein except that they differ in sequence from the original protein at selected sites and wherein the variant proteins can be expressed from the library of nucleic acids as cell surface proteins in mammalian cells; (c) introducing the first nucleic acid and the library of nucleic acids into mammalian cells, thereby enabling the mammalian cells to express the original protein and a library of variant proteins with altered sequences as cell surface proteins; (d) isolating cells that express variant proteins that bind to the molecule with different affinity than do cells expressing the original protein. The isolated cells may have higher or lower binding affinity than do cells expressing the original protein. The mammalian cells can comprise an FRT site, and the nucleic acids of (a) and (b) can comprise an FRT site. The cells of (d) can be isolated using FACS. The isolated cells of (d) can be cultured, and cultured cells expressing variant proteins that bind the molecule with different affinity than do cells expressing the original protein can be isolated from the cultured cells. The protein can comprise an Fc region of an antibody, can be an antibody, and/or can be a full-length antibody or an scFv-Fc.

The invention further comprises group of mammalian cells displaying a group of at least about 100 or 1000 different recombinant human antibodies, which may be scFv-Fcs or full length antibodies, on their cell surfaces, wherein the library of nucleic acids encoding the group of antibodies have been introduced into the cells via transfection using a vector that does not comprise sequences derived from vaccinia virus. The group of cells may display at least about 10, 50, 100, 1000, 10,000, or 100,000 different antibodies. The invention further encompasses a group of mammalian cells displaying a group of at least about 100, 1000, 10,000, or 100,000 different scFv-Fcs on their cell surfaces, wherein the library of nucleic acids encoding the group of scFv-Fcs have been introduced into the cells via transfection.

Finally, the invention provides a homodimeric intrabody, wherein each polypeptide chain of the homodimer comprises an Fc region, an scFv, and an intracellular localization sequence. The intracellular localization sequence may cause the intrabody to be localized to the ER or the Golgi. Optionally, each polypeptide chain comprises not more than one scFv.

BRIEF DESCRIPTION OF THE FIGURES

FIG. 16.

DETAILED DESCRIPTION

Figure 1:
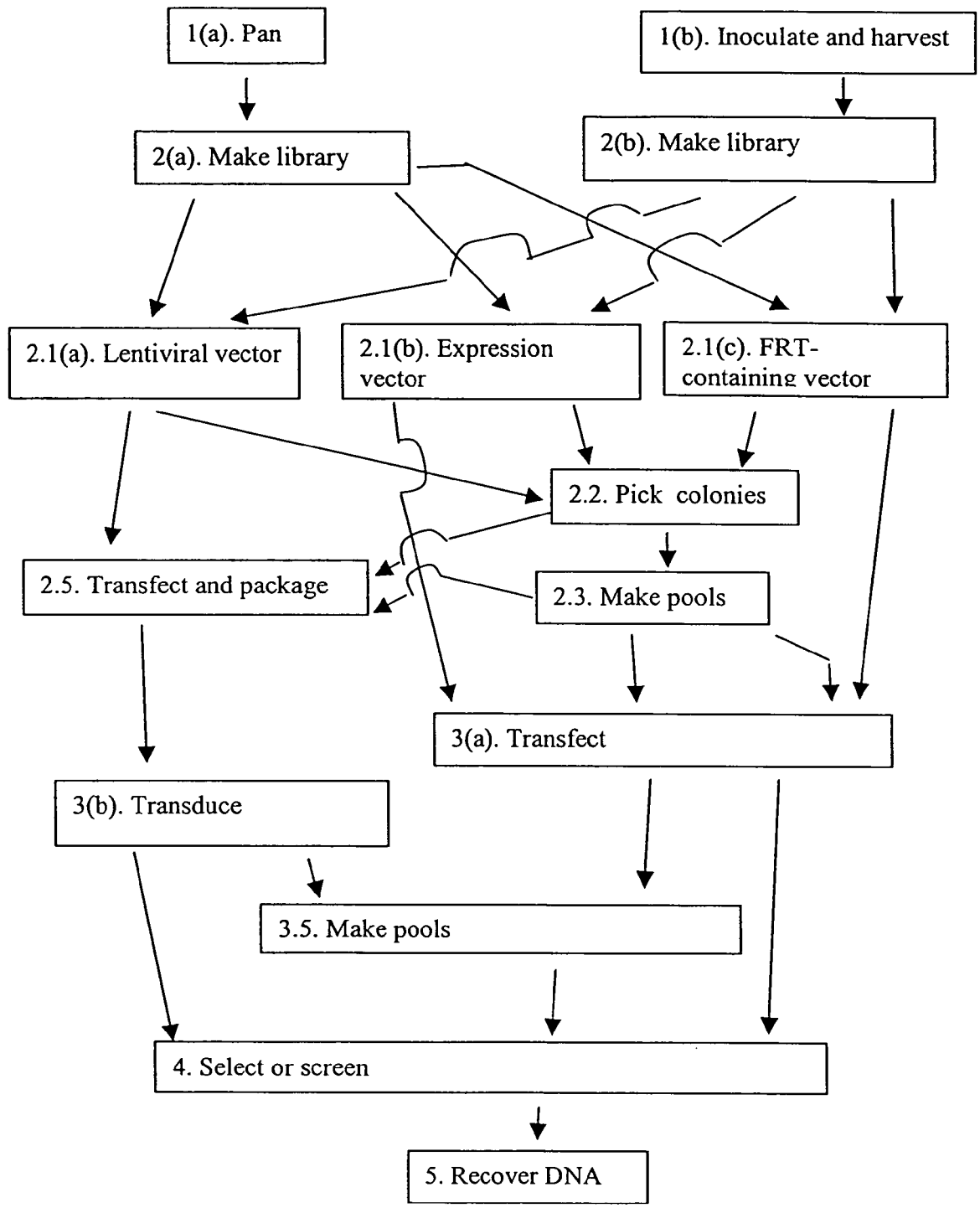
FIG. 1: This is a flow chart showing examples of the methods of the invention. Steps labeled with a number and a letter, for example "1(a)" and "1(b)," are alternative steps. Some steps are optional, and some steps may be repeated multiple times. Step 4 is common to all paths through the process. Additional steps may be added. Step 1(a) includes panning a group of antibodies displayed on, for example, phage, bacteria, or yeast to select phage or cells expressing antibodies that bind to an antigen. Step 1(b) comprises inoculating a mammal with an antigen and harvesting antibody-expressing cells. Step 2(a) comprises obtaining nucleic acids encoding, for example, antibody variable regions or scFv's from the phage or cells and inserting them into a vector such that the variable regions or scFv's can be expressed as part of a multimeric antibody, which can be a soluble, cell surface, or intracellular antibody. Step 2(b) includes obtaining antibody variable regions from cDNA of antibody-expressing cells from an inoculated mammal and inserting them into a vector such that the variable regions can be expressed as part of a multimeric antibody, which can be a soluble, cell surface, or intracellular antibody. Step 2.1 envisions transforming host cells with, for example, a lentiviral vector (2.1(a)), an expression vector (2.1(b)), or an FRT-containing vector (2.1(c)) containing sequences encoding multimeric antibodies. Steps 2.2 and 2.3 include picking and pooling host cell colonies, respectively, where the host cells have transformed with a vector encoding multimeric antibodies. Step 2.5 comprises tranfecting a packaging cell line with the lentiviral nucleic acids from step 2.1(a) and, optionally, a helper plasmid(s) to obtain viral or viral-like particles. Step 3(a) includes the transfection of the nucleic acids from the transformants from step 2.1, 2.2, or 2.3 into mammalian host cells. Step 3(b) comprises transducing the packaged nucleic acids from step 2.5 into mammalian target cells. Step 3.5 comprises sequestering individual transfectants or tranductants or pools of transfectants or transductants. Step 4 includes the selection and/or screening for antibodies that have the biological function of choice. Step 5 includes recovery of nucleic acids that are enriched for sequences encoding the antibodies emerging from the selection or screen of step 4. For example, if colonies have been picked in step 2.2, nucleic acids encoding selected antibodies may be obtained from nucleic acids used for transfection so that antibodies can be retested. If colonies have not been picked, nucleic acids encoding antibodies may be recovered from transfectants and/or transductants for retesting.

The instant invention provides new processes for efficiently screening groups of proteins, particularly antibodies, produced by eukaryotic cells to discover new therapeutic targets and/or new antibodies or proteins with therapeutically useful-properties. One of the potential advantages of therapeutic antibodies, especially those comprising Fc regions, over other therapeutic proteins is that they can have terminal half-lives in patients of up to several weeks, allowing weekly or even less frequent dosing (Presta (2002), *Curr. Pharm. Biotechnol.* 3:237-56.).

The invention encompasses screening and/or selecting for antibodies or proteins with a chosen biological function from a group of proteins or antibodies, optionally multimeric and/or Fc-containing antibodies, expressed by mammalian cells. In some embodiments, the invention includes a method for displaying an antibody comprising an Fc region, optionally a full length antibody or a scFv-Fc, on the surface of a mammalian cell and screening or selecting for antibodies with a desired biological function. Typically, the Fc-containing antibodies contain both a $V_H$ and a $V_L$ region, and the $V_H$ and $V_L$ regions are subjected to selection simultaneously. The biological function can be binding to a known protein or any function that can be tested for using in vitro assays, including in vitro assays utilizing living mammalian cells.

Screening or selecting for multimeric, optionally Fc-containing, antibodies produced by mammalian cells can be advantageous for a number of reasons. First, since the biological properties of antibody fragments do not always correlate with those of full length antibodies, the biological properties of an Fc-containing antibody must usually be ascertained during the development of a therapeutic antibody. Protein folding, glycosylation, and/or modification is likely to differ in proteins produced in prokaryotic versus mammalian cells. Existing phage, bacterial, and yeast systems are not suitable for displaying Fc-containing antibodies. The processes of the invention circumvent tedious individual conversion of scFv's or Fab fragments from phage libraries into full length antibodies for individual testing. Such conversions can be particularly tedious when both the antibody fragment and the multimeric antibody contain more than one polypeptide chain, for example, when converting a Fab fragment into a full length antibody. The methods of the invention allow direct screening or selection for an multimeric antibody, optionally a full length antibody, with the desired biological properties from a group of multimeric antibodies comprising a group of antibody fragments. For example, the methods of the invention can be used to select or screen directly for Fc-containing antibodies produced by mammalian cells that are neutralizing antibodies.

In some embodiments, the process of altering the antibodies to find related antibodies with higher affinity, called affinity maturation, can be streamlined using the methods of the invention. Affinity maturation can be important to the development of a therapeutic antibody. Currently, affinity maturation is carried out by random mutagenesis of portions of the variable regions of the heavy and light chains of the antibody. See e.g. Yang et al. (1995), *J. Mol. Biol.* 254:392-403; Pini et al. (1998), *J. Biol. Chem.* 273:21769-21776; Schier et al. (1996), *J. Mol. Biol.* 263:551-567. A library of mutants, usually expressed as Fab or scFv fragments, is expressed in bacteriophage and subjected to a screen or selection based on affinity to the antigen. Once identified, higher affinity mutants must be converted into full length antibodies and expressed in a mammalian system for testing. However, since affinities of fragments do not always correlate with affinities of full length antibodies containing them, the efficiency of the process can be low. The instant invention provides a method for performing the affinity maturation process directly using full length or other multimeric antibodies produced in a mammalian system. The nucleic acids encoding the variant forms of the original antibody can be made by altering sequences known to be involved in antigen binding, such as the complementarity determining regions (CDRs), using known methods. These altered nucleic acids can be introduced into mammalian cells, optionally after propagation in bacterial host cells. Optionally, an expression system can be used in which most of mammalian cell transfectants have only one plasmid integrated in their genome. Therefore, most of the transfectants express one or more molecules of one antibody. When using "most" in this context, it is meant that at least about 80% or about 90% of the transfectants express nucleic acids encoding only one antibody that was introduced by transfection, and therefore express only one antibody. This can be ascertained as follows. Individual transfectants can be isolated, for example by using a FACS machine. The individual transfectants can be cultured, and expressed sequences can be amplified by reverse transcription plus polymerase chain reaction (PCR) of the RNA of the individual transfectants to isolate expressed sequences encoding antibody variable regions. Primers for this purpose can be designed based on the sequence of the vector and of the nucleic acids encoding the more conserved portions (i.e., the framework regions) of antibody variable regions. See e.g. Kabat et al. (1991), Sequences of Immunological Interest, National Institutes of Health, Bethesda, Md. for a discussion of antibody structure. PCR is described in, e.g., Mullis et al. (1986), Cold Spring Harbor Symposia on Quantitative Biology LI: 263-73. These PCR fragments can be sequenced to determine whether they have a single sequence. Such analysis of at least about 10 independent transfectants is necessary to determine whether the criteria of "most" has been satisfied as meant herein, although analysis of more independent transfectants can give a more accurate determination.

In alternate embodiment, the methods of the invention can be used to select variants of any protein that have different binding affinities to a known molecule. Such a selection is carried out in essentially the same way as affinity maturation of antibodies, except that the protein may or may not be an antibody, and variants with either greater or lesser affinity to the molecule can be selected. Screening for variants of a mammalian protein in mammalian cells can be advantageous since a mammalian protein is more likely to be correctly folded, glycosylated, and modified when it is produced in mammalian cells rather than prokaryotic cells.

There are many uses of antibodies that require the use and/or the expression of the antibody in mammalian cells in order to select or screen for the antibody with the most desirable functional properties, which may include properties other than binding. A few examples of the many possible selections or screens included in the methods of the invention include the following: (1) selection or screening for antibodies that have agonistic effects on cell surface receptors (or making sure that antibodies to cell-surface receptors do not have agonistic function); (2) selection or screening for antibodies that can be expressed within a mammalian cell and prevent the cell-surface expression or secretion of a target antigen; and (3) selection or screening for antibodies that induce or prevent a biological response in a mammalian cell. Microbial expression of antibodies may be inadequate for these purposes for several reasons. First, antibodies may need to be multivalent (i.e., dimeric, trimeric, tetrameric, etc.) to show an effect or to show a more significant effect in some assays. Further, an Fc-mediated immune effector function may be necessary to show effects in some assays. In addition, microbial products may interfere with some biological assays. In some situations, it may be necessary to express the antibody on, or within, a mammalian cell to assess its activity. See e.g. Hwang et al. (2002), *J. Immunol.* 169:633-637. In such cases, the microbially-expressed antibody can be reformatted and expressed in mammalian cells, a time-consuming and tedious process that limits the number of candidate antibodies that can be screened. This invention provides methods by which large numbers of candidate antibodies can be rapidly switched into a variety of mammalian expression formats for screening or selection of antibodies with the desired functional properties. In some embodiments, the screening or selection may not require binding to a particular protein but may require some other biological function. In many cases, binding to a known or unknown antigen may be necessary in performing a biological function. Thus, the methods of the invention provide the possibility of discovering antibodies with particular biological functions that bind to unknown antigens.

Definitions

An "antibody," as meant herein, is a protein, which can bind to an antigen, comprising at least an antibody variable region, preferably a $V_H$ region and optionally also a $V_L$ region. Numerous known antibody sequences are listed, and the conserved structure of antibody variable regions is discussed in Kabat et al. (1991), Sequences of Immunological Interest, National Institutes of Health, Bethesda, Md. A variable region comprises three complementarity determining regions (CDRs) and four framework regions (FRs) arranged in the following order: FR1 CDR1 FR2 CDR2 FR3 CDR3 FR4. FRs are conserved in sequence relative to CDRs. Such regions can be located in an antibody sequence using the guidance of Kabat et al., supra. The structure of variable regions is described in detail in, e.g., Kabat et al., supra. An antibody may or may not also comprise an Fc region, a $C_L$ region, and/or a $C_H1$ region. If an antibody does contain an Fc region, the antibody can be of the IgG, IgA, IgM, IgE, or IgD isotypes. In some embodiments, antibodies can be of the $IgG_1$, $IgG_2$, $IgG_3$, or $IgG_4$ isotype. See e.g., Kuby, *Immunology*, Second Edition, W.H. Freeman and Co., New York (1994), for a discussion of isotypes and the structure of antibodies.

The term "full length antibody" refers to a molecule similar in structure to a naturally-occurring antibody, that is, containing an entire heavy chain and an entire light chain. See e.g. Kabat et al., supra or Kuby, *Immunology*, Second Edition, p. 109-32, W.H. Freeman and Co., New York (1994) for discussion of the structure of naturally-occurring antibodies. Also included among "full length antibodies" are antibodies similar in structure to the naturally-occurring dromedary antibodies that contain only two complete heavy chains (often with an unusually long CDR3 region) and no light chains. Muldermans et al. (2001), *J. Biotechnol.* 74:277-302; Desmyter et al. (2001), *J. Biol. Chem.* 276:26285-26290.

"Antibody fragments" refer to any protein comprising a portion of a full length antibody. Examples of antibody fragments include Fc regions, Fab fragments, single chain antibodies comprising heavy and light chain variable regions (scFv's), F(ab')$_2$ fragments, etc.

A "counterstructure," as meant herein, refers to a protein that binds to another protein in nature, often thereby mediating a biological effect. In general, a receptor or a decoy receptor and a cognate ligand are the "counterstructures" of each other. For example, insulin-like growth factor (IGF) and IGF receptor are the "counterstructures" of each other.

An "intracellular antibody" or "intrabody," as meant herein, is an antibody that locates inside a cell and is not a cell surface or secreted protein. Intracellular antibodies can include "intracellular localization sequences" directing their localization or retention within specific compartments within the cell, such as the nucleus, the mitochondria, the endoplasmic reticulum, or the Golgi. See e.g. Richardson and Marasco (1995), *Tibtech* 13:306-310; Pumphrey and Marasco (1998), *BioDrugs* 9(3):179-185; U.S. Pat. Nos. 6,329,173, 5,851,829, 5,965,371, 6,004,940, 6,072,036, and 6,329,173. An intracellular localization sequence may lead to retention within the cell and degradation of a protein.

An "intracellular localization sequence" is an amino acid sequence that-directs a protein to be retained within a cell that would otherwise not be retained within a cell. Such sequences include, for example, endoplasmic reticulum (ER) localization sequences, Golgi localization sequences, nuclear localization sequences, etc.

Numerous examples of Golgi localization sequences are known in the art, although the commonalities between such sequences are not clear in some cases. A fairly clear example of a Golgi localization sequence is the amino acid sequence YQRL when it is present within a C terminal cytoplasmic tail of a transmembrane protein. Nilsson and Warren (1994), *Curr. Opin. Cell Biol.* 6(4):517-521; Wu et al. (2003), *J. Immunol.* 170:4196-4200; Machamer (1993), *Curr. Opin. Cell Biol.* 5:606. Many known Golgi localization sequences contain a transmembrane domain and, in some cases also a cytoplasmic domain of a Golgi protein. Zerfaoui et al. (2002), *Glycobiology* 12(1):15-24; Teasdale et al. (1992), *J. Biol. Chem.* 267(6):4084-4096; Tang et al. (1992), *J. Biol. Chem.* 267(14):10122-10126; Wong et al. (1992), *J. Biol. Chem.* 117(2):245-258; Gerrard and Nichol (2002), *J. Virol.* 76(23):12200-12210; Nilsson and Warren (1994), *Curr. Opin. Cell Biol.* 6(4):517-521. Other proteins contain other Golgi localization sequences in a C-terminal tail. Machamer (1991), *Trends Cell Biol.* 1(6):141-144; Shanks et al. (2002), *J. Biol. Chem.* 277(43):40967-40972; Corse and Machamer (2002), *J. Virol.* 76(3):1273-1284; and Perez et al. (2002), *J. Cell Biol.* 156(4):631-642. Common features among these diverse sequences do not point to an easily explained consensus sequence for Golgi localization. See e.g. Corse and Machamer, supra.

ER localization sequences are amino acid sequences that are sufficient to cause a protein to be localized in the ER by any mechanism, for example statically (see e.g. Cocquerel et al. (1999), *J. Virol.* 73(4):2641-2649) or by a retrieval mechanism (see e.g. Teasdale and Jackson (1996), *Ann. Rev. Cell Dev. Biol.* 12:27-54). Examples of ER localization sequences that function when attached to a protein whose carboxy terminus is within the lumen of the ER, including soluble proteins and type II and IV transmembrane proteins, include the amino acid sequence KDEL and variants thereof. Examples of such variants include the following: DDEL, DEEL, DKEL, HDEL, KDEI, KNEL, KEDL, KEEL, KDDL, QEDL, QDEL, QEEL, RDEL, REEL, REDL, and RDDL. U.S. Pat. No. 6,329,173; Munro et al. (1987), *Cell* 48:899-907; Hangejorden et al. (1991), *J. Biol. Chem.* 266:6015-6018; Andres et al. (1991), *J. Biol. Chem.* 266(22):14277-14282; Ozawa and Muramatsu (1993), *J. Biol. Chem.* 268(1):699-705. Preferably, such sequences are located at the carboxy terminus of the protein.

Further, the 31 amino terminal amino acids of the mature rotavirus outer capsid glycoprotein VP7, QNYGINLPITSM-DTAYANSTQEETFLTSTL, are sufficient for ER retention of a chimeric soluble protein that also comprises a cleavable signal sequence upstream of the VP7 sequence. Maass and Atkinson (1994), *J. Virol.* 68(1):366-378. Thus, this sequence is an ER localization sequence as meant herein.

In addition, a soluble or membrane-spanning protein may be localized in the ER by virtue of its association with another protein that is localized in the ER. In such a case, the sequences in the protein responsible for the binding of the protein to the other protein are "ER localization sequences" as meant herein. In some cases, such sequences are located in membrane spanning regions. Nilsson and Warren (1994), *Curr. Opin. Cell Biol.* 6(4):517-521. Further, at least one soluble protein localized to the lumen of the ER appears to be retained there because of weak electrostatic interactions with the membrane of the ER. Kellokumpu et al. (1994), *J. Biol. Chem.* 269(48):30524-30529. Amino acid sequences capable of such an interaction are "ER localization sequences" as meant herein.

Di-lysine sequences located near a carboxy-terminus, including K(X)KXX (where X is any amino acid, and an amino acid in parenthesis may or may not be present) and variants thereof, can serve as ER localization sequences for transmembrane proteins in which the carboxy terminus is cytoplasmic, such as type I and III transmembrane proteins. von Heijne in Membrane Protein Structure: Experimental Approaches, White, ed., pp. 27-40, Oxford University Press, Oxford & London (1994). Examples of variants of K(X)KXX that can function as ER localization sequences include RXKXX, KKX, KXRXX, KXKXX, KKKXX, RKXX, KXKXX, and VRTGKKGKRD (where X is any amino acid). Teasdale and Jackson (1996), *Ann. Rev. Cell Dev. Biol.* 12:27-54; Shin et al. (1991), *Proc. Natl. Acad. Sci.* 88:1918-22; Nilsson et al. (1989), *Cell* 58:707-718; Nilsson and Warren (1994), *Curr. Opin. Cell Biol.* 6(4):517-521.

The transmembrane protein US3 of human cytomegalovirus (CMV) has a cytoplasmic carboxy terminus and a luminal amino terminus, which contains the amino acid sequences sufficient for US3's localization in the ER. The sequence RM SGNFTEKH is necessary and sufficient for the retention of US3 in the ER, and the underlined residues are known to be required portions of this sequence. Lee et al. (2003), *J. Virol.* 77(3):2147-2156. Therefore, RMSGNFTEKH and variants having the sequence XXSXXXXEKX that are sufficient for ER retention are ER localization sequences as meant herein. Further, the transmembrane and cytoplasmic domains of the human CMV protein UL16 are sufficient to cause intracellular localization and are therefore intracellular localization sequences as meant herein. Dunn et al. (2003), *J. Exp. Med.* 197(11):1427-1439.

Similarly, in transmembrane proteins in which the amino terminus is cytoplasmic, such as type II or IV transmembrane proteins, a diarginine sequence (RR) within the first five amino terminal amino acids can be sufficient to confer ER localization. Nilsson and Warren (1994), *Curr. Opin. Cell Biol.* 6(4):517-521; Schutze et al. (1994), *EMBO J.* 13:1696-1705; Jackson et al. (1993), *J. Cell Biol.* 121:317-333. Such sequences are therefore ER localization sequences as meant herein.

Still other ER-localized transmembrane proteins require their transmembrane domain and, in some cases, also their cytoplasmic carboxy terminal tails for retention in the ER. For example, the rubella virus type I transmembrane protein E1 requires both its transmembrane domain and its C terminal tail for ER retention. This sequence, which is WWNLTLGA-ICALPLVGLLACCAKCLYYLRGAIAPR, is therefore an ER localization sequence as meant herein. The E1 and E2 envelope glycoprotein of hepatitis C virus have a C terminal transmembrane domains of 31 and 29 amino acids, respectively, each of which is sufficient to direct localization of a chimeric protein to the ER. Cocquerel et al. (1998), *J. Virol.* 72(3):2183-2191; Cocquerel et al. (1999), *J. Virol.* 73(4): 2641-2649. Such transmembrane domains are therefore an ER localization sequences as meant herein. Similarly, the carboxy terminal 35 amino acids of rat microsomal aldehyde dehydrogenase, including a transmembrane domain flanked by regions charged amino acids, is sufficient to direct localization to the ER. Masaki et al. (1994), *J. Cell Biol.* 126(6): 1407-1420. Further dissection of this area revealed that the transmembrane domain and either one of the charged flanking regions is sufficient to direct ER localization. Therefore, sequences such as KQFNKGRLQLLLLVCLVAVAAVIV, WSKFFLLNKGRLQLLLLVCLVAVAAVIVKDQL, WSKFFLLKQRLQLLLLVCLVAVAAVIV, and other sequences reported to direct ER localization by Masaki et al. (supra) are ER localization sequences as meant herein. Similarly, the transmembrane domain of an antibody of the IgM class is also sufficient to direct ER localization and is therefore an ER localization sequence as meant herein. Williams et al. (1990), *J. Exp. Med.* 171:947-952.

The yeast Sec12p is a type II transmembrane protein that localizes to the ER. The transmembrane domain of Sec12p (SRFFTNFILVLLSYILQFSL) is sufficient for ER localization and is therefore an ER localization sequence as meant herein. Sato et al. (1996), *J. Cell Biol.* 134(2):279-293. Further, the N-terminal, cytoplasmic domain of Sec12p is also sufficient to direct localization to the ER. Therefore it is also an ER localization sequence as meant herein. Sato et al., supra.

To determine whether a particular amino acid sequence is an intracellular localization sequence, the following experiments can be performed. First, a test protein that is normally secreted into the culture medium in detectable quantities when produced by cultured mammalian cells can be identified. An amino acid tag that allows for affinity purification of the protein from the medium, such as a Myc tag (such as the C-terminal epitope of human c-myc, AEEQKLISEEDL) or a polyhistidine tag, can be added to the protein if necessary. Nucleic acid constructs encoding versions of the protein (optionally, plus a tag) with and without the putative intracellular localization sequence can be made and used to transfect mammalian cells. The cells can be metabolically labeled with at least one radioactive amino acid. Culture medium can be collected and the protein can be prepurified by affinity chromatography or by precipitation with an antibody. For example, if the protein includes a polyhistidine tag, it can be prepurified on a nickel column; or if the protein includes a Myc tag, it can be prepurified by immune precipitation with a polyclonal anti-Myc antibody. Alternatively, a protein without a tag can be prepurified by immune precipitation with a polyclonal antibody that binds to it. The prepurified fraction can be subjected to gel electrophoresis, and the intensity of the band(s) representing the protein with and without the putative intracellular localization sequence can be compared. If the putative intracellular localization sequence is functioning as such, the intensity of the band(s) representing the protein should be much less in samples in which the transfected construct included nucleic acids encoding the putative intracellular localization sequence. Such a test is used by, for example, Maass and Atkinson ((1994), *J. Virol.* 68(1):366-378).

To determine whether an intracellular localization sequence targets a protein to the ER or the Golgi, colocalization experiments employing confocal microscopy can be performed. Briefly, a Golgi or an ER marker can be selected, preferably one for which an antibody is available, in some cases a commercially available antibody. Golgi markers include mannosidase I, galactosyl transferase, and human golgin-97, among many other possible markers. ER markers include the murine endoplasmic reticulum protein 72 and protein disulfide isomerase (PDI), among many others. A test protein that is normally secreted into the culture medium can be identified, and nucleic acid constructs encoding versions of the protein (optionally, plus a tag) with and without the putative ER or Golgi localization sequence can be made and used to transfect mammalian cells. Transfected cells, fixed appropriately for microscopy, can be combined with two primary antibodies, one that binds to the test protein (or a tag included in the test protein) and one that binds to the selected Golgi or ER marker. The two primary antibodies can be visualized by the addition of two secondary antibodies, each of which binds to one of the primary antibodies, labeled with different colored dyes, such as, for example, green dyes, including FITC or Alexa Fluor® 488 (Molecular Probes, Eugene, Oreg.), and red dyes including rhodamine or Alexa Fluor® 453 (Molecular Probes, Eugene, Oreg.). Confocal microscopy of the stained cells can determine whether the test protein colocalizes with the ER or Golgi marker. Such studies are performed, for example, in the following references: Masaki et al. (1994), *J. Cell Biol.* 126(6):1407-1420; Lee et al. (2003), *J. Virol.* 77(3):2147-2156; Hobman et al. (1997), *J. Virol.* 71(10):7670-7680. One of skill in the art will realize that a protein produced as a result of the introduction of an exogenous gene or regulatory sequence into a cell can be produced at high levels and that an overproduced protein can mislocalize. Thus, when a test protein localizes predominantly to the ER or Golgi, although some lesser amount of it may be detected in other cellular compartments or extracellularly, it can be considered to localize to the ER or Golgi, as meant herein.

A "kind of mammalian cells," as used herein, refers to an established cell line or a group of cells isolated from tissue from a known source such as lung, liver, colon tumor, etc.

Cells or cell lines that are "kinds of mammalian cells," as meant herein include primary cell cultures, for example human umbilical vein endothelial cells (HUVEC), gingival fibroblasts, dermal fibroblasts, human foreskin fibroblasts, or any other culture derived from tissue, and established cell lines, such as Colo205, HeLa, CHO, 293T, Cos, CV1, BHK, among many, many cells or cell lines, which may be cancer cells.

Further, it is understood in the art that a group of mammalian cells cultured over a period of time can proliferate and that cells in a culture at a later time can be the result of the division of cells present at an earlier time. Hence they are not actually the same cells. Rather, the cells present at a later time are predominately the progeny of the cells present at an earlier time. Nonetheless, when mammalian cells are referred to herein over a span of time as having been in a certain condition at an earlier time, it is to be understood that it is the parental cells or cells that have not since divided which were in the condition at the earlier time, not necessarily the identical cells that are present at a later time. For example, when it is said that cells have been transfected, it is meant that the cells themselves or cells that are parents to the cells have been transfected.

A "labeled" protein is conjugated to a molecule that makes it possible to isolate cells expressing another protein on their surface to which the labeled protein can bind. A "labeled" protein can be, for example, fluorescently labeled (in which case the cells can be isolated by FACS) or conjugated to biotin (in which case the cells can be isolated using streptavidin-coated magnetic beads). Other kinds of labeling are also possible. A labeled protein can comprise a "tag," such as a myc tag, that can be bound, and therefore detected by a known antibody.

The term "mammalian host cells" refers to mammalian cells that are viable in culture and into which DNA can be introduced by transfection, which includes introduction by transduction. Examples of mammalian host cells include, for example, Cos1 cells, 293 cells, and CHO cells, among many others. In some embodiments, this term refers to cells that can be transfected at a high frequency.

The term "host cells" used without "mammalian" refers to cells in which nucleic acids introduced into the cells can be recovered in sufficient amount and in a sufficiently pure form to enable the transfection of mammalian cells. Examples of host cells include *Escherichia coli* and cells of the species *Bacillus* and fungal cells, such as *Saccharomyces cerevisiae* and *Schizosaccharomyces pombe*, among others.

The term "mammalian target cells" refers to mammalian cells that can be tested in vitro for a desired biological function. In some embodiments, such cells may be primary cells, optionally human cells. In some embodiments, mammalian host cells and target cells may be the same cells. In some cases, such cells may also serve as mammalian host cells. For example, the Colo205 cancer cells of Examples 4 and 5 are mammalian target cells as meant herein.

A "Fab fragment" is an antibody fragment comprising a light chain comprising a $V_L$ and $C_L$ region and a portion of a heavy chain comprising a $V_H$ and a $C_H1$ region. A Fab fragment does not comprise a $C_H2$ or $C_H3$ region. See e.g., Kuby, *Immunology*, Second Edition, pp. 110-11 W.H. Freeman and Co., New York (1994) for a discussion of what Fab fragments are.

An "scFv" is a single chain antibody comprising a heavy chain variable region ($V_H$) and a light chain variable region ($V_L$) and not comprising a constant region of an antibody. In some embodiments scFv's can also comprise a linker of variable length between the heavy and light chain variable regions. Although an scFv can be fused to other amino acid sequences, the portion of a protein referred to as an scFv preferably does not comprise any substantial amount of amino acid sequence other than a $V_H$ region, a $V_L$ region, and, optionally, a linker joining these sequences.

An "Fc region" of an antibody is a heavy chain fragment comprising a $C_H2$ and a $C_H3$ domain and a hinge region or a variant of such a fragment, and not comprising a $C_H1$ domain or a $V_H$ domain. See e.g. Kuby, *Immunology*, Second Edition, p. 110-11, W.H. Freeman and Co., New York (1994). An Fc fragment can be of the IgA, IgD, IgE, IgG, or IgA isotype, including IgG1, IgG2, IgG3, IgG4 or other subtypes. Variants of Fc regions, as meant herein, may comprise from 1 to about 30 insertions, deletions, or substitutions of a single amino acid relative to a naturally-occurring Fc region.

An "Fc-containing" antibody comprises an Fc region. Examples of Fc-containing antibodies include, for example, full length antibodies, scFv-Fcs, and antibodies consisting of an Fc region and a heavy chain variable region, among other possibilities.

An "scFv-Fc," as used herein, is a recombinant protein that is a fusion of an scFv with an Fc region. See Li et al. (2000), *Cancer Immunol. Immunother.* 49:243-252; Powers et al. (2001), *J. Immunol. Methods* 251:123-135; Gilliland et al. (1996), *Tissue Antigens* 47:1-20.

A "membrane association sequence," as used herein, refers to transmembrane domains or glycophosphatidylinositol (GPI) anchor sequences. GPI anchor sequences can be recognized as described in Udenfriend and Kodukula (1995), *Methods Enzymol.* 250:571-582. Transmembrane domains can be predicted as described by Sonnhamer et al. (1998), *Proc. of ISMB* 6:175-182. Transmembrane domains and GPI anchor sequences that can be recognized as described above are membrane association sequences as meant herein. A protein comprising a membrane association sequence may, in many cases, be associated with the cell surface, particularly if the protein also comprises a signal sequence in its precursor form (see discussion of "signal sequence" below). A protein comprising both a membrane association sequence and an intracellular localization sequence may, instead, be localized intracellularly. Association of a protein with a cell surface can be determined by fluorescence activated cell sorting (FACS) analysis using non-permeabilized cells that express the protein. FACS is described in, e.g., Current Protocols in Cytometry, Robinson et al., eds., John Wiley & Sons (2004); Edidin (1989), Methods in Cell Biology 29:87-102.

As used herein, a "multimeric" antibody or protein is one comprising more than one polypeptide chain. For example, a full length antibody comprising four polypeptide chains, two heavy chains and two light chains, is a "multimeric" antibody, as is a scFv-Fc, which comprises two polypeptide chains, each comprising an Fc region and an scFv. In contrast, an scFv comprising a single polypeptide chain that does not form multimers is not "multimeric," although a Fab fragment is "multimeric," since it is a dimer. Different polypeptide chains in a multimeric antibody can be linked by disulfide bridges. Multimers can be dimers, trimers, or tetramers or may comprise 5, 6, 7, 8, 9, or from 10 to 20 polypeptide chains.

A "multimerization domain," as meant herein, mediates the formation of a multimer. Numerous multimerization domains are known in the art. These include Fc regions of antibodies, leucine zippers (Landschulz et al. (1988), *Science* 240:1759), and any other domain capable of mediating multimerization.

A "recombinant" protein or antibody is one resulting from the process of genetic engineering. The term "genetic engineering" refers to a recombinant DNA or RNA method used to create a cell that expresses a gene at elevated levels or at lowered levels, or expresses a mutant form of the gene. In other words, the cell has been transfected, transformed or transduced with a recombinant polynucleotide molecule, and thereby altered so as to cause the cell to alter expression of a desired polypeptide. Methods and vectors for genetically engineering cells and/or cell lines to express a polypeptide of interest are well known to those skilled in the art. Genetic engineering techniques include but are not limited to expression vectors, targeted homologous recombination, gene activation (see, for example, U.S. Pat. No. 5,272,071 to Chappel), and trans activation by engineered transcription factors (see e.g., Segal et al. (1999), *Proc. Natl. Acad. Sci. USA* 96(6): 2758-2763). Optionally, the polypeptides are expressed under the control of a heterologous control element such as, for example, a promoter that does not in nature direct the production of that polypeptide. For example, the promoter can be a strong viral promoter (e.g., CMV, SV40) or a promoter from a highly transcribed mammalian gene such as actin that directs the expression of a mammalian polypeptide. A vector comprising vaccinia virus sequences may or may not be used. The cell may or may not normally produce the polypeptide. For example, the cell can be a CHO cell that has been genetically engineered to produce a human polypeptide, meaning that nucleic acid encoding the human polypeptide has been introduced into the CHO cell. Alternatively, the cell can be a human cell that has been genetically engineered to produce increased levels of a human polypeptide normally present only at very low levels (e.g., by replacing the endogenous promoter with a strong viral promoter).

Soluble secreted proteins generally comprise an N-terminal "signal sequence," which is a hydrophobic sequence that mediates insertion of the protein through the membrane bounding the ER. Type I transmembrane proteins also comprise signal sequences. "Signal sequences," as meant herein are amino-terminal hydrophobic sequences which are usually enzymatically removed following the insertion of part or all of the protein through the ER membrane into the lumen of the ER. Thus, it is known in the art that a signal precursor form of a sequence can be present as part of a precursor form of a protein, but will generally be absent from the mature form of the protein. When a protein is said to comprise a signal sequence, it is to be understood that, although a precursor form of the protein does contain the signal sequence, a mature form of the protein will likely not contain the signal sequence. Signal sequences contain a residue adjacent to and immediately upstream from the cleavage site (position-1) and another residue at position-3, which are important for this enzymatic cleavage. Nielsen et al. (1997), *Protein Eng.* 10(1):1-6; von Heijne (1983), *Eur. J. Biochem.* 133:17-21; von Heijne (1985), *J. Mol. Biol.* 184:99-105. Signal sequences can be identified as described by Neilsen et al. (supra). Examples of signal peptides or sequences that are functional in mammalian host cells include the following: the signal sequence for interleukin-7 (IL-7) described in U.S. Pat. No. 4,965,195; the signal sequence for interleukin-2 receptor described in Cosman et al. ((1984), *Nature* 312:768); the interleukin-4 receptor signal peptide described in EP Patent No. 0 367 566; the type I interleukin-1 receptor signal sequence described in U.S. Pat. No. 4,968,607; the type II interleukin-1 receptor signal peptide described in EP Patent No. 0 460 846; the signal sequence of human IgK (which is METDTLLLWV-LLLWVPGSTG); and the signal sequence of human growth hormone (MATGSRTSLLLAFGLLCLPWLQEGSA). Many other signal sequences are known in the art.

"Transduction," as used herein, refers to the introduction of nucleic acids into a eukaryotic cell by means of a virus or a virus-like particle, which can be a fully functional virus or a defective virus incapable of reproducing itself without additional genetic information.

"Transfection," as used herein, refers generally to the introduction of nucleic acids into a mammalian cell. The nucleic acid can be introduced by any method, including such well known methods as calcium phosphate coprecipitation, electroporation, biolistic particle delivery, microinjection, lipofection using a cationic lipid formulation, complex formation with DEAE dextran, or transfection using novel reagent such as GENEJUICE™ (Novagen, Madison, Wis.), among many possible methods. This term fully encompasses the term "transduction," which refers to a particular method of introducing nucleic acids into a eukaryotic cell. When it is said that mammalian cells have been transfected or transduced at some time in the past, it is meant that the cells at hand or cells that gave rise to the cells at hand via cell division have been transfected or transduced.

"Transformation" refers to the introduction of nucleic acids into "host cells" in which the nucleic acids and/or copies thereof can be replicated and can be recovered in a reasonably pure form. In some embodiments, one molecule of the nucleic acids is introduced into most transformed cells such that a single species is replicated within most transformed cells. "Host cells," as meant herein, can be, for example, bacterial cells, such as *Escherichia coli* or cells of the species *Bacillus*, fungal cells, such as *Saccharomyces cerevisiae* or *Schizosaccharomyces pombe*, or any other cells in which the transforming nucleic acids can be propagated and recovered in sufficient abundance and in a sufficiently pure form to enable the transfection of mammalian cells. In some embodiments, transformation conditions may need to be adjusted to limit the number of molecules of nucleic acids introduced into each host cell. When nucleic acids are introduced into either prokaryotic or eukaryotic cells, it is meant that the nucleic acids or a copies of them made in vitro or in vivo are introduced into the cells.

DESCRIPTION OF THE PROCESS

The process comprises a series of steps with various options at almost every step. In the methods of the invention, a group of proteins, optionally multimeric and/or Fc-containing antibodies, produced by mammalian cells is subjected to a selection or screen based on functional properties. The group of antibodies can be of moderate size, for example, at least about $10^1$, $10^2$, $10^3$, $10^4$, $10^5$, $10^6$, $10^7$, or $10^8$. A simplified flow chart illustrating the process with some of its many options is shown in FIG. 1. What option is appropriate at each step can depend on factors such as, for example, the number of antibodies to be screened, the format in which the starting group of antibodies is expressed, and the nature of the biological function to be used as a screening tool. Other steps in addition to those shown in FIG. 1 may be added.

In an optional first step (step 1(a) of FIG. 1), a group of antibodies or proteins is subjected to at least one selection step to enrich for antibodies that bind to a particular cell type or a particular molecule, optionally a protein. The group of antibodies or proteins can be, for example, a group of scFv's or Fab fragments expressed in bacteriophage or on the surface of, for example, bacteria or yeast cells. If selecting for antibodies that bind to a particular molecule, the molecule may be attached to a solid support as described in Example 1, and those phage or cells expressing antibodies that bind to the solid support can be isolated. In other embodiments antibodies that bind to a particular cell type can be selected. Such selections are described in e.g., Huls et al. (2001), *Cancer Immunol. Immunother.* 50:163-171. The cells can be fixed, which affords easier handling, or unfixed, which may offer an opportunity to select antibodies that bind to cell surface antigens that are altered by fixation. A particular kind of cells can be selected with reference to the biological function to be screened/selected for in a subsequent step of the process. An appropriate cell type would be one that antibodies with the desired biological function would be expected to bind to. For example, if antibodies capable of inhibiting the proliferation of cancer cells were to be screened for in a subsequent step, it would be expected that such antibodies could bind to cancer cells. Thus, it would be appropriate to initially select for antibodies that can bind to cancer cells. To select for antibodies that bind to cells, the antibodies (which can be displayed, for example, on phage) can be mixed with the cells under conditions conducive to binding. The cells (along with the phage that bind to them) can then be separated from the solution by, for example, filtration or centrifugation or by washing cells that adhere to a solid surface. If the antibodies are expressed on cells rather than phage, other means can be used. For example, a biotin-conjugated antibody that binds to the cells used for panning, but not to the cells expressing the antibodies, can be bound to streptavidin-coated magnetic beads, which can bind to the cells. The antibody-expressing cells can be combined with the immobilized cells, and those that bind to the magnetic beads can be isolated. Selection for antibodies that bind to cells, rather than specific, known antigens, has the advantage that there is a possibility of selecting for antibodies that bind to previously unknown antigens displayed on a cell surface that have a biological function that can be selected/screened for. Such an antigen need not be a protein and may comprise more than one cell surface molecule. A selection step for binding to a chosen kind of cells or a particular molecule can be repeated once or multiple times, for example, at least about 2, 3, 4, 5, 6, or 7 times. If desired, two or more different pre-selection steps can be performed either simultaneously or in sucession. For example, antibodies that bind to two different kinds of cancer cells can be selected. Alternatively, phage-displayed antibodies that bind to a given protein may be isolated by at least two different panning steps that use different methods for separating the phage that bind from those that don't.

Optionally, further refinement of such a first step (not shown in FIG. 1) can be achieved by one or more negative selection steps, which can be performed either before or after the positive selection step described above. For example, if selecting for phage-displayed antibodies that bind to cancer cells, the phage-displayed antibodies can be mixed with non-cancerous cells, and antibodies that do not bind to these cells can be retained for further testing. Such a negative selection can eliminate at least some of the antibodies that bind non-specifically to any kind of cells, thereby enriching for antibodies that bind specifically to cancer cells. Similarly, if selecting for phage-displayed antibodies that bind to a particular protein, the phage-displayed antibodies can be mixed with an unrelated protein or proteins affixed to a solid support or with only the solid support, and antibodies that do not bind can be retained for further testing. This selection can eliminate at least some of the antibodies that bind nonspecifically to the solid support or to any protein.

In some embodiments, a first preselection step may be unnecessary or may be performed in vivo as in step 1(b) of FIG. 1. If downstream steps include a positive selection for mammalian cells expressing an antibody or protein with the desired function, a pre-enrichment step may be less necessary. In addition, if the starting pool of antibodies or proteins is less than about $10^6$ or $10^7$ in number, a pre-enrichment step may be unnecessary. To perform an in vivo pre-enrichment step as suggested in step 1(b), a mammal, for example a mouse, can be inoculated with an antigen, optionally a protein, a kind of cells, or fragments of a kind of cells, known to be related to the biological function to be screened for in a later step. Thereafter (step 2(b), FIG. 1), cells expressing antibodies can be isolated from, for example, a spleen, a lymph node, or peripheral blood of the mammal. B cells can be purified from the tissue or from peripheral blood mononuclear cells. Nucleic acids encoding antibody variable regions can be amplified from, for example, B cells by reverse transcription plus PCR (RT-PCR) and inserted into a vector (such as those shown in FIGS. 2 and 3) in which the variable regions can be expressed in a mammalian cell as part of an multimeric antibody, such as a scFv-Fc or a full length antibody, which may be a secreted soluble antibody, a cell surface antibody, or an intrabody. See e.g. Chang et al. (1989), *J. Immunol.* 143(1):315-321 for a description of how to perform RT-PCR.

In a second step (step 2(a), 2(b), or 2(c) of FIG. 1), nucleic acids encoding, for example, a group of variable regions, which may be scFv's, that are pre-enriched (or not), as described above, can be introduced into a vector, optionally after amplification, in which the nucleic acids can be expressed in both mammalian cells and in cells that can be transformed for the purpose of producing nucleic acids of adequate purity and quantity for a mammalian transfection. These cells can be, for example, bacterial cells, such as *Escherichia coli* or *Bacillus subtilus*, or fungal cells. In some embodiments, the antibodies in the first selection step are expressed as, for example, Fab fragments or scFv fragments. In this second step, the antibodies can be converted into a multimeric form, comprising, for example, an Fc region, such as a scFv-Fc or a full length antibody, which comprises two heavy and two light chains. In some embodiments (step 1(b) of FIG. 1), the pre-enriched group of antibodies may be full length antibodies. In this case, a portion of the antibodies, including at least a variable region, can be amplified by PCR for cloning. It is most convenient to convert scFv's to scFv-Fcs and Fab fragments to full length antibodies, although it is also possible to convert scFv-Fcs to full length antibodies and Fab fragments to scFv-Fcs. In the methods of the invention, the multimeric, optionally Fc-containing, antibodies, such as scFv-Fcs or full length antibodies, can be expressed by mammalian cells as secreted, soluble molecules, cell surface molecules, or intracellular antibodies. ScFv-Fcs and full length antibodies made in mammalian cells can have several advantages over scFv's or Fab fragments including their multimeric nature and their longer in vivo half life, higher affinity for antigen, and lesser tendency to form aggregates. Moreover, an antibody made in mammalian cells is more likely to be properly folded and glycosylated than one made in prokaryotic cells.

Transformation of nucleic acids encoding the proteins or multimeric antibodies into host cells, such as *E. coli* cells, serves multiple purposes. First, it provides enough pure DNA to successfully transfect mammalian cells and puts the antibody or protein gene(s) in a context in which it (they) can be expressed in mammalian cells. Second it can convert the antibody or protein to a multimeric form, optionally one that comprises an Fc region. Finally, depending on the cells and methods used for transformation, each transformant may contain only one kind of protein- or antibody-encoding nucleic acid. If so, transformation provides a way to isolate single species of proteins or antibodies that can, optionally, be screened individually or in pools. In some embodiments, *E. coli* colonies may be picked robotically. Pools of from 1 to about 400 colonies can be made. Such pools can contain, for example, not more than about 50, 75, 100, 150, 200, 300, 400, or 500 colonies and/or at least about 10, 20, 30, 40, 50, 75, or 100 colonies. In some embodiments, a Petri dish of colonies might be pooled. *E. coli* plasmid DNA can also be prepared robotically. In some embodiments, recombinant DNA from other suitable host cells for transformation might also be prepared robotically. In other embodiments, a pool of plasmid DNA from all or a large number of the transformants (such as at least about $10^3$, $10^4$, $10^5$, $10^6$, $10^7$, $10^8$, $10^9$, or $10^{10}$) can be used to transfect mammalian cells. In such embodiments, other strategies can be used to isolate the desired antibody genes as long as the biological assay (used in step 4, FIG. 1) can be read out at a single cell level. Examples of such assays include (1) induction of production of a reporter, a cytokine, or a receptor, (2) intracellular translocation of a molecule, (3) cell death, (4) resistance to cell death, (5) proliferation or viability in a set of conditions where most of the cells will not remain viable or proliferate, or (6) staining with a labeled antigen.

Figure 2:
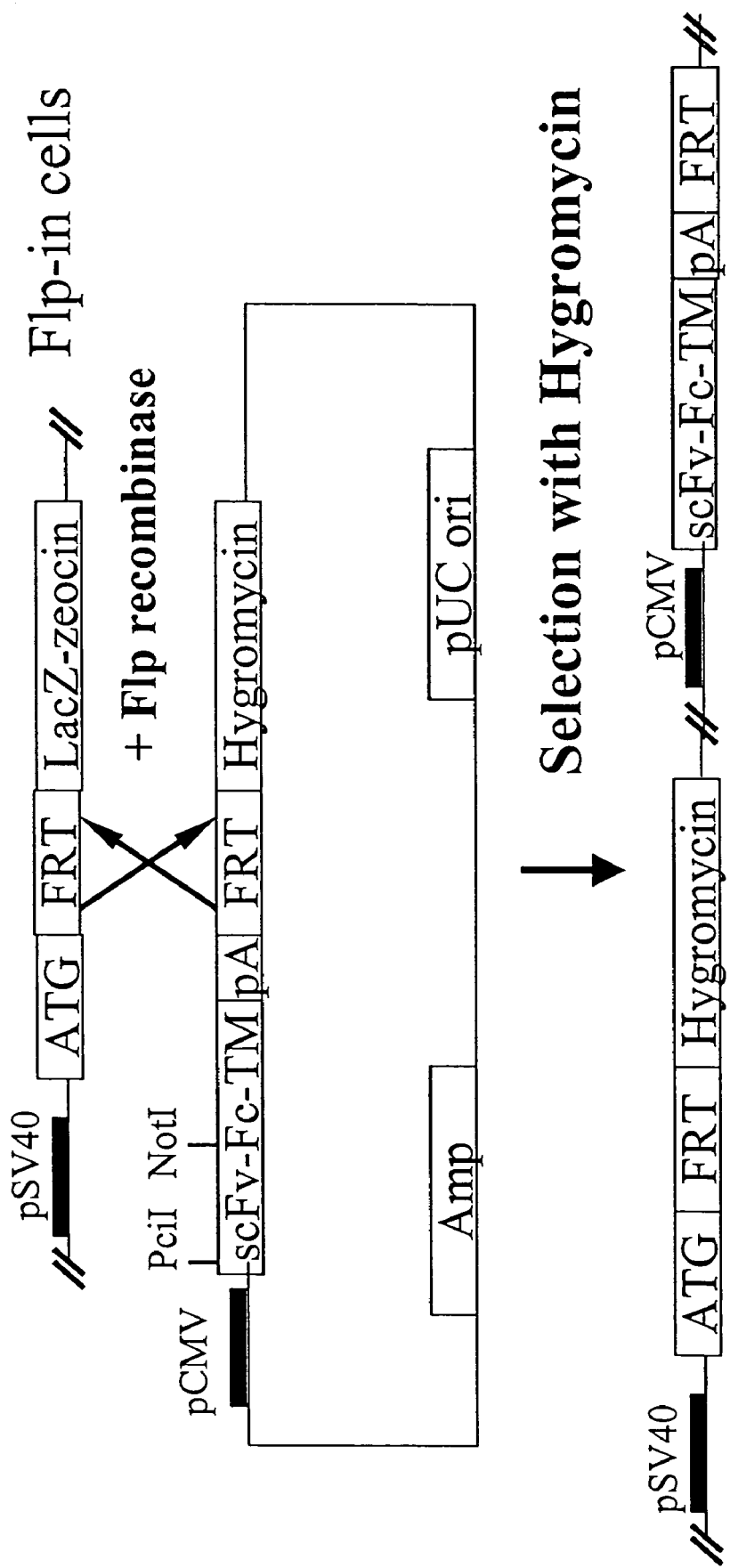
FIG. 2: This figure diagrams a FLP-IN™-type system designed to produce mammalian transfectant cells that contain a chromosomally integrated copy of the nucleic acid used for transfection. Such a system is described in, e.g. U.S. Pat. Nos. 5,654,182, 5,677,177, and 5,885,836 and in O'Gorman et al. (1991), Science 251: 1351-55. The top line diagrams the host chromosomal integration site that has been genetically engineered to contain a FLP recombination target (FRT) site between the ATG start codon and the remainder of the LacZ gene, which is fused to a gene encoding a protein conferring resistance to zeocin (LacZ-zeocin), a glycopeptide antibiotic of the bleomycin family. The plasmid, diagramed below the top line, includes a cytomegalovirus promoter (pCMV), a region that encodes a cell surface scFv-Fc (scFv-Fc-TM, showing the PciI and NotI sites used to clone the scFv fragment into the vector in Example 5), a polyadenine addition site (pA), an FRT site (FRT), a gene encoding a protein that confers hygromycin resistance (hygromycin), a bacterial origin of replication (pUCori), and a gene conferring ampicillin resistance (Amp). This vector may also include regions encoding an intracellular localization sequence and/or a membrane localization sequence. As diagrammed in the bottom line, transfectants containing a chromosomally integrated copy of the plasmid are expected to be hygromycin resistant and zeocin sensitive and to transcribe RNA encoding the scFv-Fc from the pCMV promoter.
Figure 3:
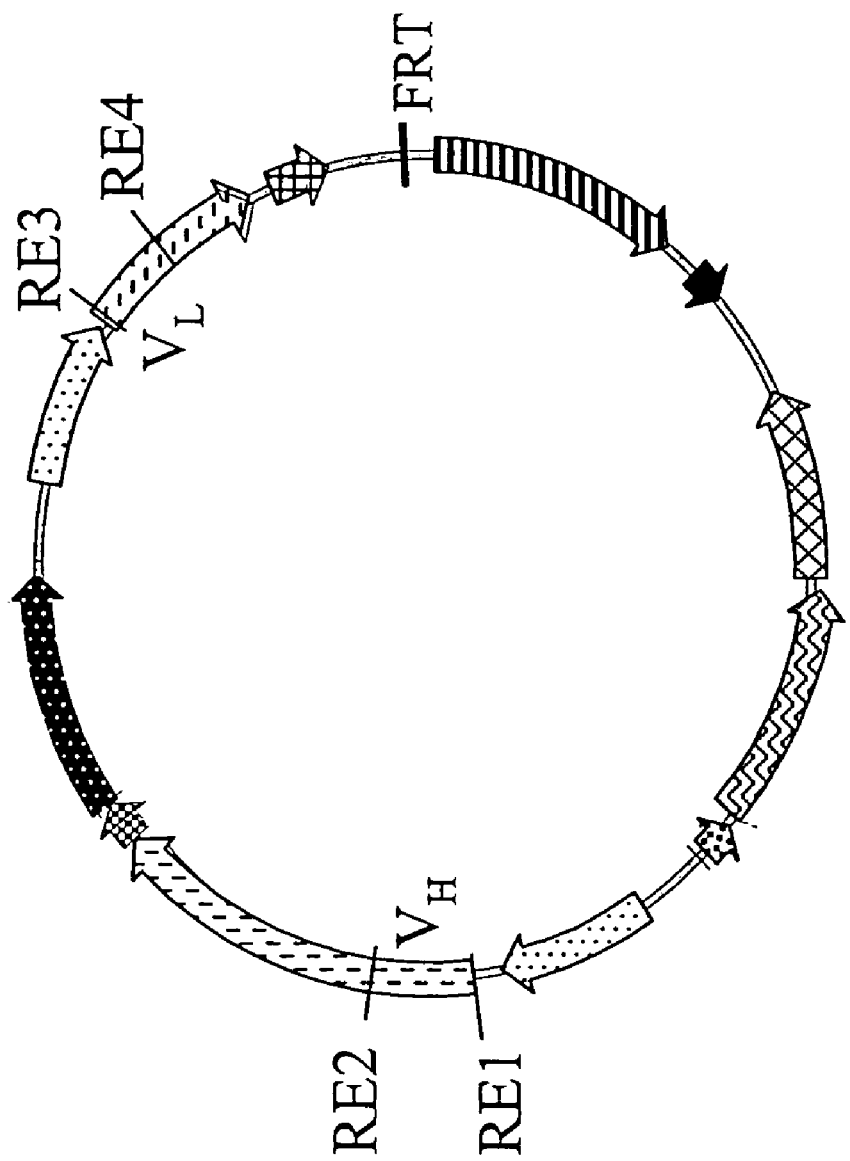
FIG. 3: This is a diagram of a plasmid that can be used to convert sequences encoding heavy and light chain variable regions into sequences encoding full-length antibodies, which, in this embodiment, can be displayed on the cell surface. The plasmid contains four unique restriction sites (RE1, RE2, RE3, and RE4) for insertion of the heavy and light chain variable regions. The plasmid is shown with heavy and light chain variable regions inserted. Other portions of the plasmid are designated as follows: IgG heavy chain, ▭; transmembrane domain, ▬; a polyadenylation site, ■; promoter, ▭; antibody light chain, ▭; polyadenylation site, ▦; FRT site, ▬▬▬; hygromycin resistance gene, ▬; polyadenylation site, ■; bacterial origin of replication, ▨; ampicillin resistance gene, ▩; and bacterial promoter, ▩.

Various kinds of vectors can be used in this second step (steps 2(a), (b), and (c) of FIG. 1), some of which are illustrated in FIGS. 2 and 3. In embodiments where a soluble secreted antibody or a cell surface antibody is subjected to selection or screening, the antibody can be expressed on a vector similar to a FLP-IN™ vector (Invitrogen), as illustrated in FIGS. 2 and 3, and transfected into cells that contain an appropriate site for site-specific chromosomal integration. As explained in U.S. Pat. Nos. 5,654,182, 5,677,177, and 5,885,836, US Patent Application No. 2002/0166138, and O'Gorman et al. (1991), *Science* 251:1351-1355, such vectors can integrate into a specific site in the genome of a mammalian cell line that has been genetically engineered to contain a FLP recombination target (FRT) site (see FIGS. 2 and 3) using the FLP recombinase of *Saccharomyces cerevisiae*. As shown in Example 6, it is likely that most of the cells transfected using this system integrate a single antibody-encoding sequence into their genome. In many embodiments, FRT site-containing vectors cannot direct the production of virus or virus-like particles.

Any other vector system in which most mammalian transfectants integrate a single copy of the transfecting DNA into a targeted chromosomal location would be appropriate to use with the methods of the invention. For example, another such system is the Cre-LoxP system described by Trinh and Morrison. Trinh and Morrison (2000), *J. Immunol. Methods* 244: 185-193. This system requires the introduction of the Cre recombinase, which can catalyze recombination between two LoxP sites. In some embodiments, two LoxP sites with slightly different sequences (such that recombination between the two different sites cannot be catalyzed by the Cre recombinase) may be present in a mammalian cell that is transfected with multimeric antibody-encoding sequences that are flanked by the same two different LoxP sites. In this situation, an antibody-encoding sequence can be inserted between the two different LoxP sites without the possibility of also being excised by Cre recombinase. In other embodiments, the LoxP sites may be identical. In another aspect, the expression or activity of Cre recombinase may be conditionally controllable. It may also be possible to positively select for the antibody insertion, as with the vector shown in FIG. 2, so that cells containing an appropriate insertion can be selected for. In such a situation, it may be less necessary to control expression or activity of Cre or to ensure that non-identical LoxP sites flank the insertion.

When using a FLP-IN™-type system or a similar system, it may be advantageous to transfect the mammalian host cells with a large pool of transformant DNA, rather than to use DNA from individual transformants or pools of transformants. Since most of the mammalian transfectants are likely to contain a single expressed antibody gene, it is feasible to recover DNA encoding the selected antibodies from the mammalian transfectants, thereby avoiding the need to pick transformant colonies. FIG. 2 shows a vector suitable for converting an scFv to a scFv-Fc. FIG. 3 shows a vector suitable for converting heavy and light chain variable regions from a Fab fragment or an scFv into a full length antibody. In addition to the regions shown in FIGS. 2 and 3, the vectors may encode a membrane association sequence and/or an intracellular localization sequence linked to the antibody sequences. Both of these vectors can integrate at a chromosomal site in an appropriately engineered mammalian host cell.

Alternatively, a vector suitable for practicing the invention may lack sequences that can direct it to integrate into a specific chromosomal site and have sequences directing the expression of the antibody, optionally at high levels, in a mammalian cell. Such expression vectors cannot typically direct the production of virus or virus-like particles.

Alternatively, a vector capable of directing the production of a virus or virus-like particle may, or may not, be used. Such vectors may or may not include all sequences necessary for virus generation. Examples of such vectors are vectors comprising sequences from a lentivirus or a vaccinia virus. As meant herein, a vector comprises viral sequence, for example vaccinia virus sequence, when it comprises a stretch of at least about 50 nucleotides that is at least about 90%, optionally at least about 95%, identical to a viral nucleotide sequence. Conversely, a vector does not comprise viral sequence if it does not comprise such a sequence. Percent identity can be determined using the Genetics Computer Group (GCG; Madison, Wis., USA) package version 10.0 program, GAP (Devereux et al. (1984), *Nucleic Acids Res.* 12:387-395). The preferred default parameters for the 'GAP' program includes: (1) The GCG implementation of a unary comparison matrix (containing a value of 1 for identities and 0 for non-identities) for nucleotides; or other comparable comparison matrices; (2) a penalty of 50 for each gap and an additional penalty of 3 for each symbol in each gap for nucleotide sequences; (3) no penalty for end gaps; and (4) no maximum penalty for long gaps.

An expression vector will typically comprise a promoter that can direct transcription in a mammalian cell operably linked to the nucleic acids encoding an antibody. Often the promoters will be capable of a high level of transcription. Expression vectors may be advantageous in comparison with FLP-IN™-type vectors in situations where a high level of expression is required to detect the biological function being screened for. Examples of such promoters include the CMV and SV40 viral promoters, mammalian actin promoters, the promoter contained within the 3' long terminal repeat of Rous Sarcoma virus, the herpes thymidine kinase promoter, or the promoter of the metallothionine gene. Promoters from other highly expressed mammalian genes could also be used. An expression vector also typically comprises a bacterial origin of DNA replication, sequences encoding a gene product that can be positively selected for in bacteria, a polyadenylation site, a ribosome binding site, and, optionally, sequences encoding a gene product that can be positively selected for in mammalian cells, such as a sequences conferring resistance to hygromycin, neomycin, or G418. An example of an expression vector is pDC302. Mosley et al. (1989), *Cell* 59:335-348.

Other examples of expression vectors include commercially available vectors such as pTriE™-4 Ek/LIC vector (Novagen, Wis., USA) or the pGEN vectors (Promega, Wis., USA), among many others.

The regulatory sequences used in vectors are typically derived from mammalian, microbial, viral, and/or insect genes. Examples of regulatory sequences include transcriptional promoters, operators, and enhancers, a ribosomal binding site (see e.g. Kozak (1991), *J. Biol. Chem.* 266:19867-19870), an internal ribosome entry site, appropriate sequences to control transcriptional and translational initiation and termination, polyadenylation signals (see e.g. McLauchlan et al. (1988), *Nucleic Acids Res.* 16:5323-5333), and matrix and scaffold attachment sites (see Phi-Van et al. (1988), *Mol. Cell. Biol.* 10:2302-2307; Stief et al. (1989), *Nature* 341:342-335; Bonifer et al. (1990), *EMBO J.* 9:2843-2848). Nucleotide sequences are operably linked when the regulatory sequence functionally relates to the polypeptide coding sequence. Thus, a promoter nucleotide sequence is operably linked to a polypeptide coding sequence if the promoter nucleotide sequence controls the transcription of the coding sequence. A gene encoding a selectable marker, such as, for example, hygromycin resistance, is generally incorporated into the expression vector to facilitate the identification of recombinant cells.

Transcriptional and translational control sequences for mammalian host cell expression vectors can be excised from viral genomes. Commonly used promoter and enhancer sequences are derived from polyoma virus, adenovirus 2, simian virus 40 (SV40), and human cytomegalovirus (CMV). For example, the human CMV promoter/enhancer of immediate early gene 1 may be used. See e.g. Patterson et al. (1994), *Applied Microbiol. Biotechnol.* 40:691-698. DNA sequences derived from the SV40 viral genome, for example, SV40 origin, early and late promoter, enhancer, splice, and polyadenylation sites can be used to provide other genetic elements for expression of a structural gene sequence in a mammalian host cell. Viral early and late promoters are particularly useful because both are easily obtained from a viral genome as a fragment, which can also contain a viral origin of replication (Fiers et al. (1978), *Nature* 273:113; Kaufman (1990), *Meth. in Enzymol.* 185:487-511). Smaller or larger SV40 fragments can also be used, provided the approximately 250 bp sequence extending from the Hind III site toward the Bgl I site located in the SV40 viral origin of replication site is included.

A variety of antibody-encoding sequences can be created by inserting variable regions, Fab fragments, or scFv's into appropriately designed vectors, which can be expression vectors or FLP-IN™-type vectors comprising an FRT. These include full length antibodies or scFv-Fcs that are secreted, soluble antibodies, intrabodies, or cell surface antibodies comprising a membrane association sequence. All of these embodiments can comprise a signal sequence in their immature form. A soluble, secreted antibody or cell surface antibody can be expressed in almost any mammalian expression vector, optionally in one that provides for high level expression. Vectors can include promoter sequences such as the CMV or SV40 promoters commonly used in mammalian vectors. In vectors other FLP-IN™-type vectors, since multiple copies of such vectors comprising different antibodies may be contained in a single transfected mammalian cell, the mammalian cells can be transfected with plasmid DNA from a single transformant or from a pool of transformants. The vector can also comprise a signal sequence operably linked to the sequence encoding the antibody. The vector may also comprise a membrane association sequence, which may be a GPI anchor sequence or a transmembrane domain.

In some embodiments, more than one cloning step may be necessary to create plasmids encoding Fc-containing antibodies, particularly full length antibodies. For example, to clone a heavy and a light chain variable region into the vector shown in FIG. 3, each variable region can be inserted into the vector in a separate cloning step. In contrast, an scFv can be inserted into the vector shown in FIG. 2 in a single cloning step.

In other embodiments, the vector is constructed so as to encode an intracellular antibody, for example either an intracellular scFv-Fc or an intracellular full length antibody. The vector can encode a signal sequence. The vector can also encode an intracellular localization sequence, of which many examples are recited above. In some embodiments, the intracellular localization sequence causes the antibody to be retained in the Golgi or the endoplasmic reticulum. An intracellular antibody can inhibit the expression of a cell surface or secreted protein. See e.g. Dauvillier et al. (2002), *J. Immunol.* 169:2274-2283; Steinberger et al. (2000), *Proc. Natl. Acad. Sci.* 97(2):805-810. The intracellular antibodies of the invention can comprise a multimerization domain such as an Fc region. As shown in Example 3, intrabodies comprising an Fc region can inhibit expression more effectively than intracellular antibodies lacking one. One of skill in the art will realize that an intracellular antibody is analogous to a genetic knockout or an antisense strategy, where the expression of a particular gene is inhibited. Therefore, the intracellular antibody must be introduced directly into a cell in which the biological property of choice can be measured (a "target cell"). In many cases, this may be a cell type that is not readily transfected. Thus, the vector in which an intracellular antibody is introduced into a suitable mammalian host cell for transformation may be a lentiviral vector that can be packaged into viral-like particles that can be used to transduce dividing or non-dividing mammalian cells. Such a lentiviral system (VIRAPOWER™) is available from Invitrogen and includes a lentiviral vector pLenti, a packaging mix containing three "packaging plasmids," which encode the Vesicular Stomatitis Virus G protein, HIV-1 reverse transcriptase, and the HIV-1 gag/pol sequences, and a packaging cell line, 293FT. This system is based on the work of Dull et al. (1998), *J. Virol.* 72:8463-8471.

Optionally, transfectants can be sequestered as individual cells or as pools of cells of a limited size prior to screening or selecting for transfectants that produce antibodies with the desired biological properties. The pools can include, for example, not more than about 20, 50, 75, 100, 200, 400, or 500 transfectants and/or at least about 5, 10, 20, 30, 40, 50, 75, or 100 transfectants. These pools or individual cells can be allowed to proliferate prior to selection or screening. If secreted, soluble antibodies are produced by the transfectants, one of skill in the art will realize that it may be advantageous to sequester the transfectants as individual cells or pools of cells. If individual transformant colonies or pools of colonies have been sequestered at an earlier step (steps 2.2 and 2.3 or FIG. 1), plasmid DNA from each of these colonies or pools of colonies can be used to separately transfect a group of mammalian cells, thus creating a number of pools of mammalian transfectants that correspond to the transformant colonies or pools of transformant colonies or nucleic acids.

Besides an initial pre-enrichment step (such as steps 1(a) or 1(b) of FIG. 1), a later enrichment step to enrich for mammalian transfectants that express Fc-containing and/or antigen-binding antibodies on their surface may be done. A pre-enrichment step can enrich for antibody variable regions that bind to an antigen, which can be a protein or a chosen kind of cell. Nucleic acids encoding such variable regions can be inserted into a vector-that allows their expression as cell surface, multimeric, optionally Fc-containing, antibodies in mammalian cells and their propagation in a suitable host cell for transformation, such as, for example, *E. coli*. Mammalian cells expressing Fc-containing antibodies that bind to the antigen can be isolated, for example, with a labeled antigen using FACS or a strategy employing magnetic beads. For example, a fluorescently-labeled protein or cells expressing green fluorescent protein can be used to isolate cells that bind that bind to either of these fluorescent antigens by FACS. Alternatively, an antigen can be biotinylated, and cells expressing antibodies that bind to the antigen can be isolated using streptavidin-coated beads. Alternatively, the transfectants can be combined with a fluorescently-labeled antibody against an Fc region and sorted by FACS to isolate transfectants that express Fc-containing antibodies. Such a purification strategy can be repeated once or multiple times, for example, 2, 3, 4, 5, 6, or 7 times. Between purification steps, cells can be allowed to proliferate.

In any of the embodiments described above, a fourth step (step 4, FIG. 1) comprises a screen or selection of the proteins, optionally the multimeric antibodies, produced by mammalian cells for a biological property, optionally, one that is relevant to a therapeutic application and includes a biological function other than binding to antigen. For example, cell surface and/or secreted scFv-Fcs or full length antibodies may be tested for the ability to inhibit proliferation, affect viability or metabolic activity of cells (for example with a stain such as allamar blue or by monitoring luminescence due to luciferase expressed by the cells), or cause apoptosis of cancer cells, which are biological functions that include properties other than binding to antigen. Assays for apoptosis and proliferation are well known in the art and described below. In this embodiment, it can be appropriate to pre-select or pre-enrich in a first step for antibodies that bind to cancer cells. Alternatively, the proteins or multimeric antibodies may be screened or selected for binding to an antigen.

In a variation on this theme, an antibody that causes cell killing, apoptosis, or lack of proliferation of a cancer cell in combination with another molecule can be screened for. For example, many cancer cells are susceptible to cell killing via signaling through TRAIL receptor 2 (TRAILR2), which can be effected through, for example, an interaction between TRAILR2 and TRAIL or between TRAILR2 and an antibody that binds to it. See e.g., Griffith et al. (1999), *J. Immunol.* 162:2597-2605. However, not all cancer cells that express TRAILR2 are susceptible to such killing. Some such cells (called herein "insensitive cells") can be induced to be sensitive to TRAILR2-mediated cell killing by a variety agents. In some embodiments of the invention, antibodies can be screened using TRAILR2-expressing insensitive cells to find antibodies that can kill such cells or cause apoptosis in the presence of the antibody plus a known TRAILR2 antibody that induces TRAILR2-mediated killing in sensitive cells.

Numerous other biological functional tests and pre-selection steps can be part of the methods of the invention. For example, a pre-selection for phage-expressed antibodies that bind to activated T cells and a screen for scFv-Fcs that block cell contact-dependent T cell-mediated macrophage activation may identify antibodies that block activation of immune response, which can be useful in treating an autoimmune or inflammatory disease. As is known in the art, activated T cells can be isolated by, for example, using one of the many kits for isolation of specific kinds of cells sold by Miltenyi Biotec (Bergisch Gladbach, Germany; Auburn, Calif., USA). Such kits allow the isolation of specific kinds of cells by (1) contacting a mixture of cells comprising the desired cells with magnetic beads on which are displayed ligands to which the desired cells bind and subsequently separating the beads from the cell mixture and eluting the desired cells from the beads, thereby enriching for the desired cells, and/or (2) contacting the mixture of cells to magnetic beads displaying ligands to which unwanted cells in the mixture bind and subsequently removing the magnetic beads from the mixture, thereby depleting the cell mixture of unwanted kinds of cells and enriching for the desired kind of cells. T cell mediated macrophage activation can be measured by, for example, combining activated T cells, macrophages, and a candidate antibody (either a soluble antibody or an antibody displayed on a cell surface) and performing an ELISA assay measuring the production of inflammatory cytokines such as tumor necrosis factor, interleukin 1, or interleukin 6, among others. Antibodies that either promote or inhibit the production of such inflammatory cytokines could be selected. Alternatively, a preliminary step can enrich for antibodies that bind to, for example, regulatory T cells, Th1 cells, or Th2 cells, and a later step can screen for antibodies that can stimulate or inhibit the activity of the regulatory T cells, thereby causing suppression or stimulation of immune response. Activity of regulatory T cells can be measured by inhibition of $^3$H incorporation by cocultured Th1 or Th2 cells in response to antigen stimulation. See e.g. Cosmi et al. (2004), *Blood* 103(8):3117-3121 and references cited therein. Since Th1 and Th2 cells play an important role in immune response, such antibodies can be useful in treating allergic, inflammatory, and/or autoimmune diseases or in enhancing an immune response, which may be desirable, for example, in treating an infection or administering a vaccine.

In other embodiments, a pre-enrichment for phage-expressed antibodies that bind to any chosen kind of cells, for example, dendritic cells, T cells or tumor cells, can be followed by a screening assay to determine whether the selected antibodies can inhibit cell migration or adhesion. Screening assays for cell migration or adhesion can be performed, for example, as described by Gao et al. (2003), *J. Immunol. Methods* 274:185-197. Alternatively, phage-expressed antibodies that bind to, for example, dendritic cells can be isolated in a pre-enrichment step, and a subsequent screening step can be done to enrich for antibodies that inhibit nuclear translocation of NF-κB as described below in Example 1. Briefly, NF-κB nuclear translocation assays can be performed essentially as described by Ding et al. (1998), *J. Biol. Chem.* 273:28897-28905 using 384-well microtiter plates. Dendritic cells can be exposed to an appropriate stimulus such as, for example, bacterial lipopolysaccharide or tumor necrosis factor, and NF-κB translocation can be detected with, for example, an NF-κB Activation HitKit (Cellomics Inc., Pittsburgh, Pa.). Further, a pre-enrichment step could include isolation of antibodies that bind to any chosen cell type, and a subsequent screening step could involve mixing the cells of the chosen type with the antibodies and screening for antibodies that cause a change in cell shape or morphology. Such antibodies might, for example, have an effect on cell migration or adhesion. By choosing functional assays closely related to a disease, the methods of the invention make it possible to identify potentially therapeutic antibodies that bind to known or unknown target molecules. It is thus possible to identify new target molecules and/or to directly identify potentially therapeutic antibodies using the methods of the invention.

When screening secreted soluble antibodies, various strategies may be employed. For example, medium containing the antibodies can be directly screened for the biological activity. Alternatively, the antibodies can be bound to beads coated with Protein A or Protein G (both of which bind the Fc regions of antibodies) or to microtiter plates coated with Protein A or Protein G prior to screening for biological activity. As a further alternative, the antibodies can be crosslinked to each other, for example, using an IgM (pentameric) antibody that binds to the Fc regions of the antibodies, before being screened. Such strategies may increase local concentrations of the antibodies leading to clearer results.

In some embodiments, the screening or selection of step 4 may be repeated multiple times and/or two or more different (but possibly related) screening or selection steps can be done. For instance, cells expressing multimeric antibodies may be screened for caspase activity and for the ability to inhibit proliferation of cancer cells. See Example 5.

Should proteins or antibodies with the desired properties be identified in the preceding steps, nucleic acids encoding them can be isolated and retested to ensure that they do encode antibodies with the desired biological properties. If individual transformants or pools of transformants have been isolated, recombinant nucleic acids can be obtained from these for retesting. For example, if individual transformants have been isolated, plasmid DNA can be purified and used to re-transfect mammalian cells, which can then be retested to determine whether they express antibodies with the desired function. If pools of transformants have been isolated, plasmid DNA from pools testing positive can be used to transform cells to generate individual transformants expressing one kind of antibodies. Plasmid DNA from these individual transformants can be used to transfect mammalian cells, which can then be tested for function, thereby identifying proteins or antibodies having the desired function. If individual transformants or pools of transformants have not been isolated, nucleic acids encoding the protein or at least the antibody variable regions can be obtained from the transfectants or pools of transfectants that have tested positive, for example, by amplifying the expressed antibody variable region-encoding sequences by reverse transcription plus PCR. When it is said that nucleic acids are obtained from a transfectant or a mammalian cell, it is meant that the nucleic acids or copies thereof are obtained from cellular nucleic acids rather than from viral particles produced by the cells. These sequences, which may be amplified by PCR, can then be re-inserted into a suitable vector and used to generate individual transformants. Recombinant DNA from these transformants can be used to transfect mammalian cells in order to retest for function.

The proteins or antibodies identified by the methods of the invention can be used to augment an immune response (for example, when administering a vaccine or treating an infectious disease) or to treat a host of diseases, such as various cancers, autoimmune and inflammatory diseases, and infectious diseases. Cancers that may be treated using antibodies isolated by the methods of the invention include cancers arising in any tissue, including the head and neck, brain, eyes, lung, esophagus, mediastinum, stomach, pancreas, liver, biliary passages, gallbladder, small intestine, colon, rectum, anal region, kidney, ureter, bladder, prostate, breast, urethra, penis, testis, vulva, vagina, cervix, endometrium, uterus, fallopian tubes, endocrine system, soft tissues, bone, skin, peritoneum, larynx, hypopharynx, central nervous system, blood, bone marrow, lymphatic system, spleen, and cancers of unknown tissue origin. The cancers may be carcinomas, sarcomas, leukemias, seminoma, teratoma, fibrosarcoma, or any histologic type of cancer. Autoimmune and inflammatory diseases that may be treated using antibodies isolated using the methods of the invention include all conditions in which the patient's own tissues are subject to deleterious effects caused by the patient's immune system. Such effects can be mediated by autoantibodies and/or by the activation of immune effector cells, among other possibilities. Autoimmune and inflammatory diseases include, for example, Addison's disease, insulin-dependent diabetes mellitus (type I diabetes mellitus), asthma, polyglandular endocrinopathy syndromes, systemic lupus erythematosus, chronic active hepatitis, primary biliary cirrhosis, primary sclerosing cholangitis, various forms of thyroiditis (including Hashimoto's thyroiditis, transient thyroiditis syndromes, and Grave's disease), lymphocytic adenohypophysitis, premature ovarian failure, idiopathic hypoparathyroidism, pernicious anemia, glomerulonephritis, autoimmune neutropenia, Goodpasture's syndrome, multiple sclerosis, vitiligo, myasthenia gravis, rheumatoid arthritis, juvenile rheumatoid arthritis, scleroderma, primary Sjogren's syndrome, polymyositis, autoimmune hemolytic anemia, inflammatory bowel disease (including Crohn's disease and ulcerative colitis), psoriasis, psoriatic arthritis, dermatitis, autoimmune thrombocytopenic purpura, pemphigus (including pemphigus vulgaris, pemphigus foliaceus, and paraneoplastic pemphigus), spondyloarthropathies (including ankylosing spondylitis and Reiter syndrome), ocular inflammatory diseases, acute rheumatic fever, mixed essential cryoglobulinemia, and warm autoimmune hemolytic anemia, among many others. Infectious diseases treatable with antibodies isolated using the methods of the invention include viral diseases (including Acquired Immunodeficiency Syndrome, hepatitis, and herpes, among others), bacterial diseases (including infections by gram positive, gram negative, aerobic, and anaerobic bacteria and infections by mycoplasma, rickettsia, and chlamydia), fungal diseases, and diseases caused by infections by protozoans (e.g. amoeba, plasmodium, trypanosoma, etc.), helminths, ectoparasites, or unknown agents.

Treatment of disease encompasses alleviation of at least one symptom of the disorder, a reduction in the severity of the disease, or the delay or prevention of progression to a more serious disease that occurs with some frequency following the treated condition. Treatment need not mean that the disease is totally cured. A useful therapeutic agent needs only to reduce the severity of a disease, reduce the severity of symptom(s) associated with the disease or its treatment, or delay the onset of a more serious disease that can occur with some frequency following the treated condition. For example, if the disease is a cancer, a therapeutic agent may reduce the tumor burden, that is, reduce the number of viable cancer cells, the number of tumor sites, and/or the size of one or more tumors. Alternatively, a cancer treatment may prevent an increase in tumor burden, thus delaying the progression of the cancer. A patient's tumor burden may be assessed by any of a number of conventional techniques. Suitable procedures vary according to the type of cancer, but include various tumor imaging techniques, or procedures for determining the amount of a given tumor-associated antigen or protein in a patient's blood or urine. Treatment of an autoimmune or inflammatory disease may reduce inflammation and/or tissue destruction, for example, by reducing the number or size of swollen joints in a patient afflicted with rheumatoid arthritis. Treatment of an infectious disease may, for example, enhance an immune response to a pathogen such as a virus, a bacterium, or a eukaryotic pathogen.

Figure 4:
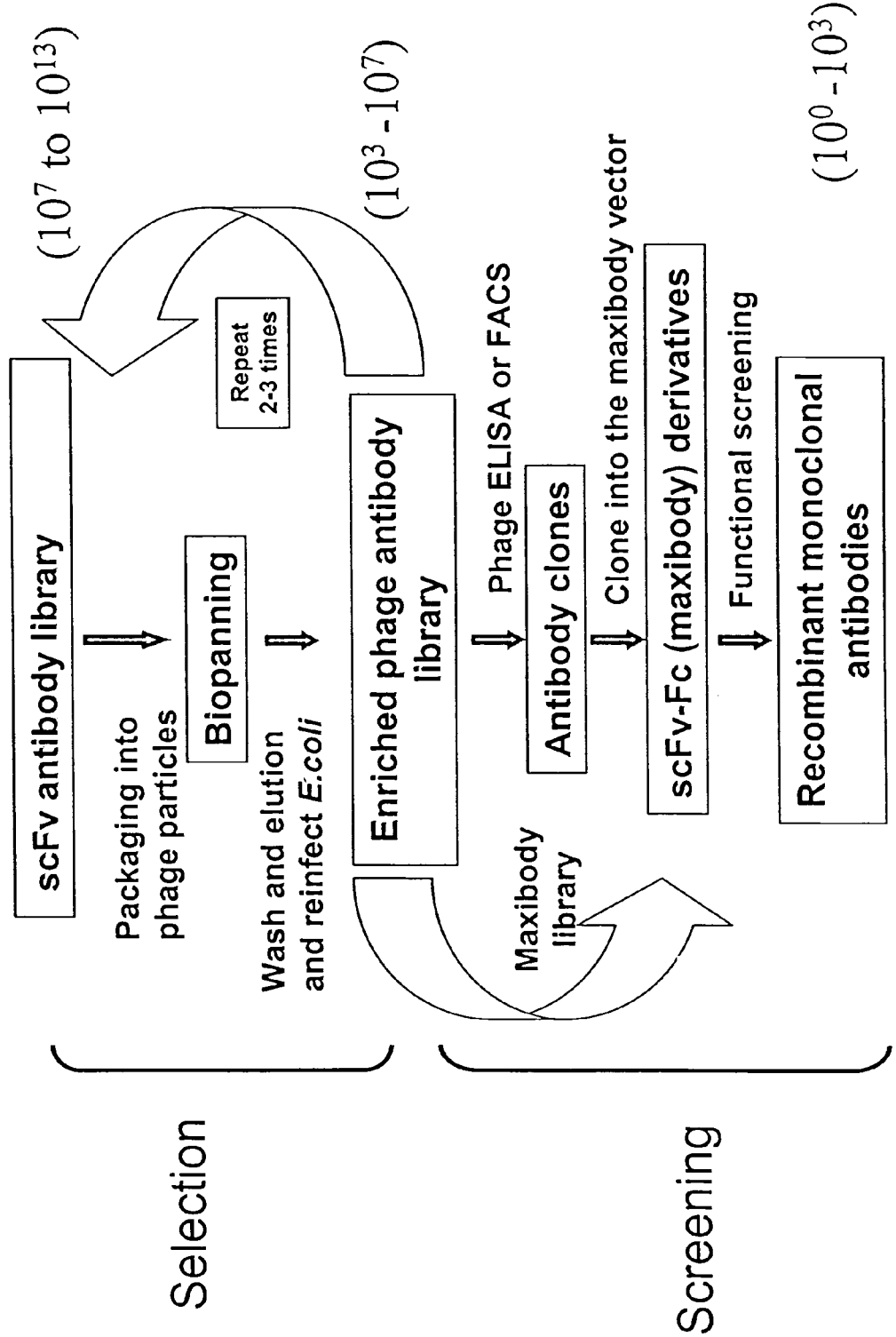
FIG. 4: This is a flow chart diagramming the steps of one general way to practice a method of the invention. The numbers at right indicate approximate numbers of antibodies that can remain at selected points in the process.

FIG. 4 illustrates one possible route through some of the steps of the invention that emphasizes the numbers of different antibodies handled at each step. Starting with at least about $10^7$, $10^8$, $10^9$, $10^{10}$, $10^{11}$, $10^{12}$, or $10^{13}$ different scFv antibodies displayed on bacteriophage, the scFv's are subjected to a selection for binding to a particular antigen ("biopanning" step), which may be a known protein or a kind of cells, and subsequent amplification by using the phage to infect bacteria, thereby producing more phage. This selection and amplification can be repeated at least once or at least two to three times to produce a group of antibodies enriched for those that bind to a particular cell type or protein. The phage that bind to the antigen may be captured, for example, by combining the phage with a biotinylated antigen and streptavidin- or avidin-coated magnetic beads. The beads can be isolated using a magnet. Methods for biotinylating proteins, nucleic acids, and cell surfaces are known in the art. See e.g. Hirsch et al. (2002), *Anal. Biochem.* 308:343-357; Marmorstein et al. in Cell Biology: A Laboratory Handbook, $2^{nd}$ Ed., vol. 4, Celis, ed., pp. 341-350 (1998); Heitzman and Richards (1974), *Proc. Natl. Acad. Sci.* 71:3537-3541. Streptavidin-coated beads are commercially available, for example from Dynal Biotech, Oslo, Norway. Alternatively, phage that bind to the antigen can be captured by mixing the phage with the antigen, which is attached to a solid support. After selection for phage that bind to an antigen, there may be from about $10^3$ to about $10^7$ scFv's remaining. The phage that bind to the antigen can be further purified by FACS sorting or phage ELISA. Gao et al. (1997), *Proc. Natl. Acad. Sci.* 98:11777-11782. Nucleic acids encoding the selected scFv fragments can then be amplified by PCR from the phage nucleic acid and inserted into a vector such as, for example, that shown in FIG. 2. The vector may encode a scFv-Fc or a full length antibody, which can then be subjected to further testing to further enrich for antibodies having a desired functional property.

If, for example, a vector that can integrate at a specific site in the genome of the mammalian host cell is used (such as those illustrated in FIGS. 2 and 3), recombinant DNA from the transformants can be used to transfect the appropriate mammalian host cells (which contain a chromosomal FRT site), along with a vector encoding the FLP recombinase, which mediates the integration. After drug selection in which the cells that do not contain the correctly integrated vector are largely killed, the resulting transfectants can be sorted by FACS using an anti-Fc antibody to stain the cells to enrich for transfectants that express an Fc on their surface. The sorted transfectants can then be distributed in microtiter plates such that a limited number of cells, for example at most about 1, 2, 3, 4, 5, 10, 20, 30, 50, 70, 100, 150, or 200 are in each well. After at least some cell growth in the microtiter plate, optionally, when the cells reach confluence, the cells can be subjected to a screen or selection to determine whether they have the desired function. The function may involve binding to an antigen or activity in an in vitro assay using living mammalian cells.

In some embodiments, functional screening is preceded by a series of steps that utilize automated methods for handling bacterial and mammalian cells. When, for example, a vector encoding an scFv-Fc is introduced into bacteria by transformation, the bacteria can be plated out under selection and colonies can be picked automatically, for example, by a Qbot (available from Genetix, Beaverton, Oreg., USA). The vector may be a FLP-IN™-type vector, as described above, but can also be an expression vector, such as pDC409, which is described in Giri et al. ((1994), *EMBO J.* 13:2822-2830), Dower et al. ((1989), *J. Immunol.* 142(12):4314-4320), and Sims et al. ((1988), *Science* 241:585-589). Expression vectors have the advantage that the inserted sequences are generally highly expressed, thereby increasing the likelihood of detecting a signal in an in vitro biological assay using mammalian cells. The picked colonies can also be cultured automatically, for example, in a HiGro machine made by GeneMachines of San Carlos, Calif., USA. Colonies may or may not be pooled either before or after culturing. Cultures or colonies can be pooled (for example into pools of about 2 to 500 colonies, optionally from about 4 to about 200, about 4 to about 100, or about 4 to about 50 colonies per pool), for example, using a MultiMe™ 96 available from the Beckman Coulter Co. Alternatively, the pools can include not m6re than about 50, 75, 100, 200, 300, 400, or 500 colonies. Recombinant DNA from the pools of transformants can also be prepared automatically, for example by a Qiagen robot such as the Biorobot 3000, available from Qiagen, Valencia, Calif., USA. Subsequently, the recombinant transformant DNA can be used to transfect mammalian host cells, which can be done automatically using, for example, an Evolution P3 machine from PerkinElmer of Boston, Mass., USA. Thereafter, mammalian transfectants expressing an antibody on their cell surface or intracellularly or culture medium containing soluble antibodies secreted by transfectants can be used to perform in vitro assays or selections utilizing living mammalian cells. Such assays or selections can also be automated, for example using the Victor2 machine produced by PerkinElmer, Boston, Mass., USA. Other automated means for handling these steps other than those specifically mentioned here might also be used. Using this system, at least about 10,000, 25,000, 35,000, 54,000, 75,000, 100,000, 200,000, or 500,000 different antibodies can be screened in a week.

In other embodiments, mammalian cells containing a chromosomal FRT site can be transfected with a large pool of recombinant DNA from transformants containing a vector comprising an FRT site, along with sequences encoding the FLP recombinase. Alternatively, a different vector system (such as a vector system using the Cre recombinase and LoxP sites) could be used as long as most transfectants express a single sequence from the DNA used for transfection. The vector can be designed to express a cell surface protein, such as a full length antibody or a scFv-Fc, and transfectants can be sorted using FACS after staining with a fluorescently-labeled antibody that binds to a portion of the protein or to an Fc region. These transfectants expressing proteins or Fc-containing antibodies on their surface can be distributed in microtiter plates such that a chosen approximate number of transfectants is deposited in each well. The target number of transfectants might be from 1 to about 400, optionally from about 1 to about 200, from about 1 to about 100, from about 1 to about 50, or from about 1 to about 10 cells per well. Since the FLP-IN™-type vector and cells are used, most transfected cells are expected to express a single kind of antibody or protein on their surface. See Example 6. Using this system, when positive wells are identified by functional screening or binding to a molecule, the antibodies or proteins can be amplified from the genome of the mammalian transfectant cells using PCR for subsequent retesting. Alternative schemes for sorting out cells expressing proteins or antibodies can also be employed. For example, an antibody that binds to an Fc region can be conjugated with biotin. Cells expressing Fc-containing antibodies can then be pulled out using streptavidin-coated magnetic beads. Cells can be appropriately diluted to distribute an approximate number of transfectants in each well of a microtiter plate.

If the mammalian cells produce secreted, soluble antibodies or proteins, one of skill in the art will realize that cells producing the antibodies or proteins may advantageously be sequestered as individuals or pools at some stage in the process. For example, transformant colonies encoding the antibodies or proteins can be picked and, optionally, combined into pools. Then, plasmid DNA from these groups of cells and their progeny can be used to separately transfect mammalian cells. If the transformants are not subdivided, then the mammalian transfectants can be subdivided into pools. For example, transfectants expressing an Fc-containing antibody on their cell surface can be detected and deposited into the wells of a microtiter plate using a FACS machine. One or more cells, for example groups of about 1 to 10, about 10 to 20, about 20 to 30, about 30 to 50, about 50 to 100, or about 100 to 200 cells can be placed in each well. Since secreted, soluble antibodies or proteins are not physically attached to the cells that produce them, it is necessary to return to the DNA contained in such pools of transfectants or transformants in order to obtain nucleic acids encoding antibodies that give a positive signal in the functional assay used.

In other embodiments, different and/or additional steps can be performed. For example, a Fab library displayed in phage can be panned for an antigen. Heavy and light chain variable regions from phage nucleic acids can be amplified and inserted into a vector such as that shown in FIG. 3. Alternatively, nucleic acids encoding heavy and light chain variable regions can be inserted into two different vectors, which could encode complete heavy or light chains when the appropriate variable region-encoding sequences are inserted. Recombinant, transformant DNA, not subdivided into DNA from individual colonies or pools, can be used to transfect mammalian cells. As shown in Example 6, the vector of FIG. 3 is probably integrated in a single copy into the mammalian host chromosomes in the majority of transfectants. Thus, most transfectants will express a single kind of antibody. Following transfection, the transfected cells can be sorted by FACS, and gates can be set such that cells expressing antibodies that bind to, for example, an anti-kappa chain antibody and the antigen will be separated out as a group. Such a sorting procedure can be repeated multiple times, for example, twice, thrice, four times, five times, six times, seven times, eight times, nine times, or 10 times. Between each sorting step, cells can be grown for at least about 1, 2, 3, 4, 5, 6, 7, 8, 9, or 10 days. The fold purification at each step can be at least about 50 fold, 100 fold, 200 fold, 400 fold, 600 fold, 800 fold, 1000 fold, 1200 fold or 1400 fold. The fold purification can be determined as follows. If, for example, transfected cells that bind to both the antigen and the anti-kappa antibody initially make up about 0.5% of the total cells (as determined by FACS), and, upon a second FACS sorting, such cells comprise 99.5% of the total cells, then the cells have been purified by 99.5/0.5=199 fold. Such purification can be repeated multiple times.

In still another embodiment, a protein or antibody with different binding properties or different levels of expression from an original protein or antibody can be selected. Alternatively, the methods of the invention can be used to select a humanized antibody with binding properties comparable to or better than those of an original antibody. The selected protein or antibody may bind a molecule, optionally a protein, with higher or lower affinity than does the original protein or antibody. Starting with nucleic acids encoding the original protein or antibody, sequence variants having randomized sequence at selected sites can be produced, optionally using PCR. The selected sites may include nucleotides within sequences encoding the CDR1, CDR2, and/or CDR3 regions of the heavy and/or light chain variable regions. The nucleic acids encoding the randomized sequence variants are referred to as a library of sequence variants. This library can be inserted into a vector, optionally a FLP-IN™-type vector, and used to transfect mammalian cells. The transfectants can express the library of nucleic acids as either secreted, soluble proteins or as cell surface proteins. These expressed proteins can then be screened for binding affinity to the molecule. Optionally, transfectants expressing the variant proteins or antibodies on their cell surface can be screened by FACS to identify cells expressing variant proteins or antibodies that bind to the molecule with affinities higher or lower than or similar to that of cells expressing the original protein or antibody. When selecting humanized antibodies with comparable binding properties to an original antibody, framework regions of the original antibody can be altered using PCR, and variants that have binding properties comparable to the original antibody can be selected. A protein or antibody may have desirable binding characteristics but may be poorly expressed in mammalian cells. Cells expressing sequence variants of such proteins or antibodies that are more highly expressed can also be selected using FACS. In some embodiments, the protein selected in this manner may be a fusion protein comprising an Fc region of an antibody and a binding region selected in vitro, such as those described in US Patent Application No. 2004/0087778.

The invention having been described, the following examples are offered by way of illustration, and not limitation. All references cited herein are incorporated by reference in their entirety.

EXAMPLE 1

Identification of Antibodies that Antagonize to IL-1R

In the following example, antibodies that bind to interleukin 1 receptor type I (IL-1$R_I$) are isolated in two different formats, full length antibodies and scFv-Fc fusions and the biological activity of the antibodies in the two different formats is assessed. IL-1$R_I$ antibodies may potentially be useful as a treatment for autoimmune diseases, including rheumatoid arthritis (RA), since IL-1ra (a naturally-occurring IL-1R antagonist) has proven to be an effective treatment of RA. Bresnihan (2002), *Ann. Rheum. Dis.* 61, ii74-ii77; St. Clair (2002), *J. Rheumatol.* 29:22-26.

Materials and Methods

Materials

All proteins used in Example 1 are human unless otherwise noted. Recombinant proteins were generated at immunex, now part of Amgen. Receptor ectodomains were also genetically fused to human IgG$_1$ Fc to facilitate their expression and purification. Cynomolgus IL-1$R_I$ ectodomain was cloned from an activated T-cell cDNA library from cynomolgus monkeys (B. Renshaw, Genbank Accession Number AY497008) and then expressed both as an Fc fusion protein and as a monovalent receptor containing C terminal FLAG epitope and His$_6$-tag (RSGSSDYKDDDDKGSSHHH-HHH). K299 (KARPAS-299) cells, used in FACS analysis studies, are a human non-Hodgkin's T cell lymphoma cell line (DSMZ, Braunschweig, Germany) that constitutively expresses IL-1$R_I$. Stable CHO cells expressing murine IL-1$R_I$ were generated by M. Kubin (Amgen) and used in NF-κB assays. Neutralizing and weakly neutralizing mouse and rat anti-human IL-1$R_I$ mAb, M1 and M8 respectively, have previously been described (McMahan et al. (1991) *EMBO J.* 10:2821-2832.).

Biotinylated human IL-1$R_I$ was generated using vendor protocols (Pierce Biotechnology, Rockford, Ill.) with some modifications. Briefly, biotinylation was performed at 25° C. for 30 min followed by 15 min on ice using a 1:2 molar ratio of receptor to biotinylation reagent (EZ-Link Sulfo-NHS-SS-Biotin, Pierce). Receptors were biotinylated to a stoichiometry approaching 2 mol biotin/mol receptor, as estimated by HABA titration (Bayer and Wilchek (1990), *Methods Enzymol.* 184:138-160.). Biotinylation of the receptor was not found to be detrimental to the IL-1 binding site as surface plasmon resonance (SPR) studies determined IL-1α to have the same binding affinity to biotinylated receptor (1 nM $K_D$, data not shown) as unmodified receptor.

Europium (Eu) labeling of lysine residues on anti-M13 bacteriophage mAb (Amersham Biosciences, Piscataway, N.J.), IL-1α and IL-1β was performed by PerkinElmer Life Sciences (Akron, Ohio) using Eu-N1-ITC. Anti-M13 mAb and receptor ligands were labeled to a stoichiometry of approximately 6.0 and 2.3 Eu residues/molecule, respectively.

Affinity Selection of IL-1$R_I$-binding scFv Clones

A panel of human IL-1$R_I$-specific scFv clones was isolated by panning 3 different human scFv antibody libraries against biotinylated soluble human IL-1$R_I$ ectodomain. These scFv libraries (from Cambridge Antibody Technology, Cambridge, U.K.) were constructed from the V-gene segments of non-immunized human donors with a total diversity of ~1×10$^{10}$ scFv fragments (Vaughan et al. (1996), *Nat. Biotechnol.* 14:309-314). Prior to panning, scFv-phage particles and streptavidin M-280 magnetic beads (Dynal Biotech, Oslo, Norway), preblocked in buffer A (PBS containing 0.1% (v/v) Tween 20 and 3% (w/v) dry nonfat milk), were incubated together to deplete streptavidin-binding phage from each library. "Precleared" libraries were then mixed with 100 nM biotinylated IL-1$R_I$ and allowed to bind for 1 h. The first round of selection was performed under low stringency conditions (100 nM IL-1$R_I$) to recover as many different IL-1$R_I$ binding candidates as possible. The phage library-antigen complex mixture was added to streptavidin beads and gently mixed for 15 min. Complex-bound beads were collected and washed several times with buffer B (PBS containing 0.1% (v/v) Tween 20). IL-1$R_I$ specific-scFv-phage molecules were eluted from the beads using 50 mM dithiothreitol. *Escherichia coli* TG1 cells (Carter et al. (1985), *Nucl. Acids Res.* 13:4431-4443.) were infected with the eluted phage (Harrison et al. (1996), *Methods Enzymol.* 267:83-109), plated onto 2YTG/Carb (2YT broth containing 4% (w/v) glucose and 100 μg/ml carbenicillin) and incubated at 30° C. overnight. Selected scFv phage clones were amplified by superinfecting TG1 cells with M13 K07 helper phage and collected and concentrated by PEG precipitation (Harrison et al., supra). In an effort to enrich for higher affinity clones, this selection process was repeated for rounds 2 and 3 with increased selection stringency (5 nM and 0.1 nM receptor, respectively) using phage isolated from the previous round. After three rounds of panning, individual clones were randomly selected from each library for further analysis.

Phage Binding and Inhibition Assays

ScFv-displaying phage binding specifically to IL-1$R_I$ were identified by plate binding assays. Briefly, 1 pmol biotinylated IL-1$R_I$ was immobilized to pre-blocked streptavidin-coated 96-well plates. Plates containing streptavidin alone were used as controls to allow identification and subsequent elimination of phage that bound nonspecifically to streptavidin or plastic. To prepare phage supernatants (Harrison et al., supra), TG1 cells in 2YTG/Carb were inoculated with individual phage clones, grown at 37° C. to OD$_{600}$ off ~0.6 then superinfected with helper phage at multiplicity of infection of 10. Cells were pelleted by centrifugation (1,900× g, 10 min at 4° C.), resuspended in 2YT media containing 50 μg/ml kanamycin and grown at 30° C. for ≧5 h. The cells were then pelleted again by centrifugation and phage-containing supernatants were diluted 2-4 fold into buffer A and incubated with immobilized receptor for 1 h at 25° C. Unbound phage and ligand were removed by washing with buffer B. Europium-labeled anti-M13 mAb was then added and allowed to bind remaining phage for 1 h. Plates were washed again and incubated with DELFIA enhancement solution for 10 min. The fluorescence signal was read at 615 nm using a VICTOR$^2$ plate reader (PerkinElmer Life Sciences).

Phage clones were also examined at 25° C. for inhibition of binding to receptor in the presence of IL-1α or IL-1β prebound to plate-immobilized receptor. In this assay, approximately 1 pmol biotinylated IL-1$R_I$ was immobilized on a streptavidin-coated plate and 30-fold excess IL-1α or IL-1β ligand was added and allowed to bind the receptor for 30 min. Phage supernatants were freshly prepared and diluted 2-fold into buffer A containing 30-fold excess ligand. This phage/ligand mixture was added to ligand-bound IL-1$R_I$ and allowed to bind for 1 h. Unbound phage were washed away with buffer B and phage bound to IL-1$R_I$ were detected by time resolved fluorescence using Eu-labeled anti-M13 mAb as described above. Phage clones were considered to be receptor-specific if they yielded signals of ≧20-fold above the streptavidin controls. Phage were defined as potential ligand blockers if the specific signal was reduced by ≧25% in the presence of excess IL-1α or IL-1β.

DNA Sequencing of Clones

ScFv-phage that bound to IL-1$R_I$ but were blocked from binding receptor in the presence of IL-1α and IL-1β were PCR amplified and sequenced across the scFv-encoding region (V$_H$, linker and V$_L$) using fdtetseq and pUC19 reverse primers (Vaughan et al. (1996), *Nat. Biotechnol.* 14:309-314). Sequences were aligned using an in-house MiniPileup program to display the clonal diversity. Each V$_H$ and V$_L$ gene was assigned to a germline V gene segment using VBASE, a publicly-available internet database sponsored by the Centre for Protein Engineering, Medical Research Council, University of Cambridge.

Dissociation Rate Ranking and Affinity Measurements

Surface plasmon resonance analysis was used to rank scFv clones based on their dissociation rates (k$_{off}$ values) and to determine equilibrium binding constants (K$_D$ values) of purified scFv-Fc and IgG proteins. All SPR experiments were performed at 25° C. in binding buffer (10 mM Hepes, 150 mM NaCl, 3 mM EDTA, 0.005% (v/v) Nonidet P-20, pH 7.4) using a Biacore 3000 instrument (Biacore, Uppsala, Sweden). Data were analyzed using BiaEvaluation software version 3.02 (Biacore).

To rank the 39 unique scFv phage clones based on dissociation rates, k$_{off}$ values were determined using ~250 resonance units (RU) of biotinylated human IL-1$R_I$ captured on one flow cell of a streptavidin-coated chip. The signal from a reference flow cell (lacking IL-1$R_I$) was subtracted from the IL-1$R_I$ flow cell signal. ScFv-phage supernatants were prepared by filtering and then diluted 2-fold into binding buffer. Phage supernatants (100 μl at 1.9×10$^{12}$ to 1.8×10$^{14}$ cfu/ml) were coinjected as analytes at 50 μl/min followed immediately by 250 μl of binding buffer containing 4 μM unlabeled IL-1$R_I$. Excess receptor was added as a competitor to minimize reassociation of phage once dissociated from the chip. Data from the first 100 s of the dissociation phase was fit using a 1:1 Langmuir binding model. The chip surface was regenerated between cycles with a 30 s injection of 10 mM glycine, pH 2.5.

Kinetic experiments were performed to determine the binding affinity (K$_D$) of human IL-1$R_I$ (monomeric) for immobilized scFv-Fc or IgG$_4$ molecules. These experiments were performed in this way to estimate monomeric binding affinities. For most scFv-Fc molecules, ~6,000 RU protein A (Amersham Biosciences) was coupled to two flow cells on a CM5 chip by amine coupling according to the vendor (Biacore). ScFv-Fc 17, 18 and 26 were alternatively captured using ~6,000 RU goat anti-human Fc (Jackson ImmunoResearch, West Grove, Pa.) because these scFv-Fc molecules contain $V_H$ regions that can also bind to protein A. The first flow cell contained a captured scFv-Fc that did not recognize IL-1$R_I$ and was used as a reference surface for scFv-Fc captured on other flow cells. For each scFv-Fc a mean of 60 RU was captured on the flow cell surface. At least six different concentrations of monomeric IL-1$R_I$ ectodomain (analyte) were then flowed over the chip surface at 50 µl/min using binding buffer containing 100 µg/ml BSA. Chips were regenerated between cycles with 10 mM glycine, pH 1.5. Data were fit using a Langmuir single-site model with double referencing. Analysis of IgG$_4$ was performed in a similar manner except a goat anti-human Fc was immobilized on the flow cells and used to capture a mean of 100 RU IgG$_4$. The control flow cell used was coated with capture antibody only.

Production of scFv-Fc and IgG$_4$ Proteins

ScFv-Fc expression constructs (H. Zhou and Z-H. Hu, unpublished data) were made by ligating Nco I/Not I restriction fragments of each scFv clone into a similarly digested modified form of the mammalian expression vector pDC409 (Giri et al. (1994), *EMBO J.* 13:2822-2830) called pDC409a-huG1Fc (Immunex/Amgen). This modified vector also contains cloned VH5 leader and IgG$_I$ Fc regions. For IgG expression constructs, DNA encoding $V_H$ and $V_L$ domains of individual scFv fragments were generated by PCR amplification of the scFv-Fc pDC409a-huG1Fc plasmids using appropriate primers listed below in a 5' to 3' direction. Heavy chain forward (VHF) and reverse (VHR) direction PCR primers were customized for specific clones:

VHF1 CTAGCTAGCCAGGTGCAGCTGG for C7, C11 and C13;
VHF2 CTAGCTAGCGAGGTGCAGCTGG for C6, C9, C10, C14 and C16;
VHF3 CTAGCTAGCCAGGTCCAGCTGG for C17 and C18;
VHF4 CTAGCTAGCGAGGTGCAGCTGTIGG for C15, C23, C26, C27;
VHF5 CTAGCTAGCCAGGTGCAGCTGC for C4;
VHR1 CTAGCTGCTGAGGAGACGG for C18;
VHR2 CTAGCTAGCTGAAGAGACGGT for C 16, and
VHR3 CTAGCTAGCACTCGAGACGG for all other clones that were reformatted. $V_H$ PCR fragments were restriction digested with Nhe I and cloned into similarly cleaved mammalian expression vector, pDC414N-HC (Immunex/Amgen), a modified form of the pDC409 vector containing a minimal Epstein-Barr replication origin (Shirakata and Hirai (1998), *J. Biochem.* 123:175-181), human IgG$_4$ constant domains (Ellison and Hood (1982), *Proc. Natl. Acad. Sci.* 79:1984-1988; Brusco et al. (1998), *Eur. J. Immunol.* 25:349-355) and a modified VH5a leader sequence.

Light chain forward (VLF) and reverse (VLR) direction PCR primers were also customized for specific clones: VLF1 CTAGCTAGCGAAATTGTGTTG for C27;
VLF2 CTAGCTAGCCAGCCTGTGCTG for C6 and C14;
VLF3 CTAGCTAGCCAGGCTGTGCTG for C13 and C23;
VLF4 CTAGCTAGCCAGTCTGCCCTG for C9, C10 and C11;
VLF5 CTAGCTAGCTCTTCTGAGCTG for C4 and C15;
VLF6 CTAGCTAGCCAGTCTGTGCTGAC for C7, C17, C18 and C26;
VLF7 CTAGCTAGCTCGTCTGAGCTG for C16;
VLR1 CTACGTACGTTTAATCTCCAGTCG for C27;
VLR2 CTACGTACGTAAAACGGTGAG for C6;
VLR3 CTACGTACGTAGGACAGTCAG for C23;
VLR4 CTACGTACGTAGGACGGTGAC for C4, C7, C9, C10, C13-15 and C26; and
VLR5 CTACGTACGTAGGACGGTCAG for C11 and C16-18.

$V_L$ PCR fragments were restriction digested with Nhe I and Bsi WI and cloned into similarly cleaved mammalian expression vector, pDC414N-LCKL (Immunex/Amgen), a modified version of the pDC409 vector containing the human K light chain constant region and a modified A27 leader sequence.

ScFv-Fc and IgG$_4$ proteins were expressed in COS-1 or PKB E5 cells and purified using protein A affinity chromatography. Briefly, antibodies were passed over a POROS20 A column (Perspective Biosystems, Foster City, Calif.) in PBS buffer, pH 7.4, bound antibodies were eluted as 1 ml fractions using 0.1 M glycine, pH 2.7 containing 0.3 M NaCl and immediately neutralized using 1.0 M Tris, pH 8.0. Peak fractions were pooled and dialyzed into PBS, pH 7.4. Purified scFv-Fc and IgG$_4$ proteins were flash frozen and stored long term at −80° C. and short-term at 4° C. Repeated freeze/thaw cycles were avoided.

Ligand Competition Assay

Competitive binding assays were used to rank putative IL-1$R_I$ antagonist candidates in scFv-Fc and IgG$_4$ formats based on their relative biochemical potency as IL-1 blockers. Assays were performed at 25° C. in streptavidin-coated 96 well microtiter plates (Greiner Bio-One Inc, Longwood, Fla.) blocked with buffer B containing 3% (w/v) BSA. To begin, 5 pmol biotinylated soluble human IL-1$R_I$ in PBS was added to each well and allowed to bind for 45 min. Unbound receptor was removed by washing with buffer B and the remaining bound receptors were then blocked for 30 min with buffer A. Plates were washed again and 50 µl of serial dilutions of competitor (scFv-Fc or IgG$_4$ in buffer A) containing 2 pmol Eu-labeled IL-1α or IL-1β were added to wells and allowed to bind receptor for 1 h. The amount of Eu IL-1 used was approximately 80% of the maximal IL-1β binding signal when bound to immobilized IL-1$R_I$. Unbound material was removed by washing. Enhancement solution was added to each well and fluorescence signals were read at 615 nm as previously described. Data were processed using GraphPad Prism version 3.03 (GraphPad Software, San Diego, Calif.) and was fit by nonlinear regression to a one-site competition binding equation. Plotted data points are the mean of quadruplicate measurements.

Flow Cytometry

FACS was used to assess the ability of scFv-Fc and IgG$_4$ proteins to recognize IL-1$R_I$ expressed on the cell surface. K299 cells were used to assess binding to human IL-1$R_I$. A stable CHO cell line expressing murine IL-1$R_I$ (produced at Immunex/Amgen) was used to assess binding to murine IL-1$R_I$. Both CV-1 and HEK293 cells transiently expressing cynomolgus IL-1$R_I$ were used to assess binding to cynomolgus IL-1$R_I$. Cells were incubated with 10 µg/ml scFv-Fc or IgG$_4$ for 1 h at 4° C. Bound scFv-Fc or IgG$_4$ was detected using phycoerythrin-conjugated goat anti-human IgG F(ab')$_2$ (Jackson ImmunoResearch). Cells were analyzed using a FACSCalibur flow cytometer (Becton Dickinson, Mountain View, Calif.). Those scFv-Fc and IgG proteins that caused a significant shift in cell fluorescence were considered receptor binders.

NF-κB Nuclear Translocation Assay

When IL-1 binds to the IL-1R$_I$ receptor complex a signaling cascade is initiated that involves the activation of cytoplasmic NF-κB and translocation to the nucleus. To access biologic activity of our putative antagonist clones, NF-κB nuclear translocation assays (Ding et al. (1998), *J. Biol. Chem.* 273:28897-28905.) were performed in 384-well microtiter plates using HeLa cells endogenously expressing human IL-1R$_I$ and a NF-κB Activation HitKit (Cellomics Inc., Pittsburgh, Pa.). Cells were seeded at a density of 2,000 cells/well and incubated overnight at 37° C. The cells were then stimulated for 40 min at 37° C. with 12 pM human IL-1α or IL-1β in the presence of various concentrations of scFv-Fc or IgG$_4$ clones. Ligand concentrations were experimentally determined based on dose titration experiments using HeLa cells. Concentrations selected were approximately 75% of maximal IL-1α or IL-1β stimulation. After ligand and clone exposure, cells were immediately washed and fixed with 3.5% (v/v) formaldehyde in PBS for 10 min at 20° C. followed by permeabilization. NF-κB and the cell nuclei were then stained according to the Cellomics protocol. Finally, cells were imaged and fluorescence measured with the Array-Scan II cytometer (Cellomics) optimizing the vendor protocol for the cells used. After subtraction of the mean cytoplasmic from mean nuclear fluorescence, data were fit using a nonlinear regression variable slope dose response using GraphPad software. Data points are the mean of quadruplicate measurements.

Results

Isolation of IL-1R$_I$ Antagonists from scFv Libraries

After three rounds of affinity selection using human IL-1R$_I$ ectodomain, individual scFv-phage candidates were randomly chosen for screening from rounds 2 and 3 of selection. Approximately 33% of the 1,152 scFv-phage screened bound specifically to IL-1R$_I$ as judged by a time-resolved fluorescence receptor-binding assay. IL-1R$_I$-binding candidates were next screened for their ability to bind to the same receptor binding sites as IL-1 using phage inhibition assays. These assays were used to identify phage candidates as potential antagonists worthy of further analysis rather than to rank them by their potency as receptor antagonists (see Discussion). Initially all candidates were tested for the ability to bind IL-1R$_I$ prebound with IL-1α. Phage candidates that were significantly inhibited (>25% inhibition) from binding to receptor in the presence of IL-1α were then tested for inhibition of receptor binding in the presence of IL-1β. Phage candidates that were inhibited from binding in the presence of both IL-1β and IL-1α were selected for further analysis. Complete inhibition of both IL-1β and IL-1α binding is desired because only very few IL-1 molecules are required to induce a strong IL-1R$_I$ response (Arend, 2002). Eighty-one (21%) of the 382 IL-1R$_I$-binding phage were significantly and reproducibly inhibited from binding in the presence of both IL-1β and IL-1α. Diversity analysis of these 81 putative antagonist clones by nucleotide sequencing revealed 39 unique sequences (data not shown).

We hypothesize that high affinity receptor binding (low K$_D$) is a desirable property of ligand-blocking clones that will likely contribute to their potency as antagonists. Purified phage representing each of the 39 putative antagonist clones were analyzed by SPR using a Biacore 3000. Estimation of dissociation rate constants was used as a surrogate for K$_D$ (k$_{off}$/k$_{on}$) for the following reasons. Firstly, k$_{off}$ values for antibody-antigen interactions typically vary over a much wider range than do association rate constants (k$_{on}$ values) (Lowman and Wells (1993) *J. Mol. Biol.* 234:564-578; Yang et al (1995), *J. Mol. Biol.* 254:392-403); consequently a low k$_{off}$ value is a common hallmark of high affinity clones (low K$_D$ values). Secondly, k$_{off}$ measurements are concentration independent and can be measured readily with scFv-phage preparations. Thirdly, k$_{on}$ determinations require estimates of functional scFv concentration that cannot be readily determined in phage format. Of the 39 putative antagonist clones analyzed by Biacore, 30 gave a robust signal (ΔRU≧60-1,300) upon binding to immobilized human IL-1R$_I$ ectodomain. These clones dissociate with rate constants (k$_{off}$) of 1.2×10$^{-3}$ to 3.6×10$^{-2}$ s$^{-1}$. The 15 clones with the slowest dissociation rates (lowest k$_{off}$ values) that were also inhibited from binding IL-1R$_I$ by ≧50% in the presence of IL-1 were selected for further analysis (Table I).

TABLE I

Properties of the lead anti-IL-1R$_I$ scFv-phage clones
The 15 scFv-phage clones with the slowest dissociation rates (lowest k$_{off}$ values) that were also inhibited from binding IL-1R$_I$ by ≧50% in the presence of IL-1 are listed.

| Clone | Library/ Round [a] | V domain family/V gene segment [b] | | k$_{off}$ [c] |
|---|---|---|---|---|
| | | V$_H$ | V$_L$ | 10$^{-3}$ s$^{-1}$ |
| C23 | D3 | V$_H$3, DP47 | V$_λ$1, DPL8 | 1.2 |
| C10 | S2 | V$_H$3, DP38 | V$_λ$2, DPL11 | 1.5 |
| C7 | S2 | V$_H$1, DP10 | V$_λ$3, DPL23 | 1.7 |
| C6 | S2 | V$_H$1, DP7 | V$_λ$3, DPL23 | 3.3 |
| C11 | S3 | V$_H$3, DP38 | V$_λ$2, DPL11 | 4.2 |
| C13 | S2 | V$_H$3, DP47 | V$_λ$1, DPL3 | 5.6 |
| C27 | D2 | V$_H$3, DP47 | V$_κ$1, DPK9 | 6.4 |
| C4 | S2 | V$_H$3, DP49 | V$_λ$3, DPL16 | 8.7 |
| C18 | B2 | V$_H$3, DP46 | V$_λ$2, DPL11 | 9.3 |
| C26 | D2 | V$_H$3, DP47 | V$_λ$1, DPL3 | 9.7 |
| C9 | S2 | V$_H$3, DP38 | V$_λ$2, DPL11 | 11.0 |
| C17 | B2 | V$_H$3, DP46 | V$_λ$2, DPL11 | 11.0 |
| C15 | D3 | V$_H$3, DP47 | V$_λ$3, DPL16 | 11.0 |
| C16 | B2 | V$_H$3, DP31 | V$_λ$3, DPL16 | 12.0 |
| C14 | S2 | V$_H$3, DP54 | V$_λ$1, DPL2 | 13.0 |

[a] ScFv-displaying phage libraries are denoted by S, D or B for spleen, DP47 or bone marrow libraries, respectively, whereas the numbers 2 or 3 indicate that clones were found in rounds 2 or 3 of panning, respectively.
[b] V domain family and V gene segment assignments from VBASE.
[c] Off-rate ranking of purified scFv-phage clones was performed using Biacore. Clones are listed in order of increasing k$_{off}$ values.

Figure 5:
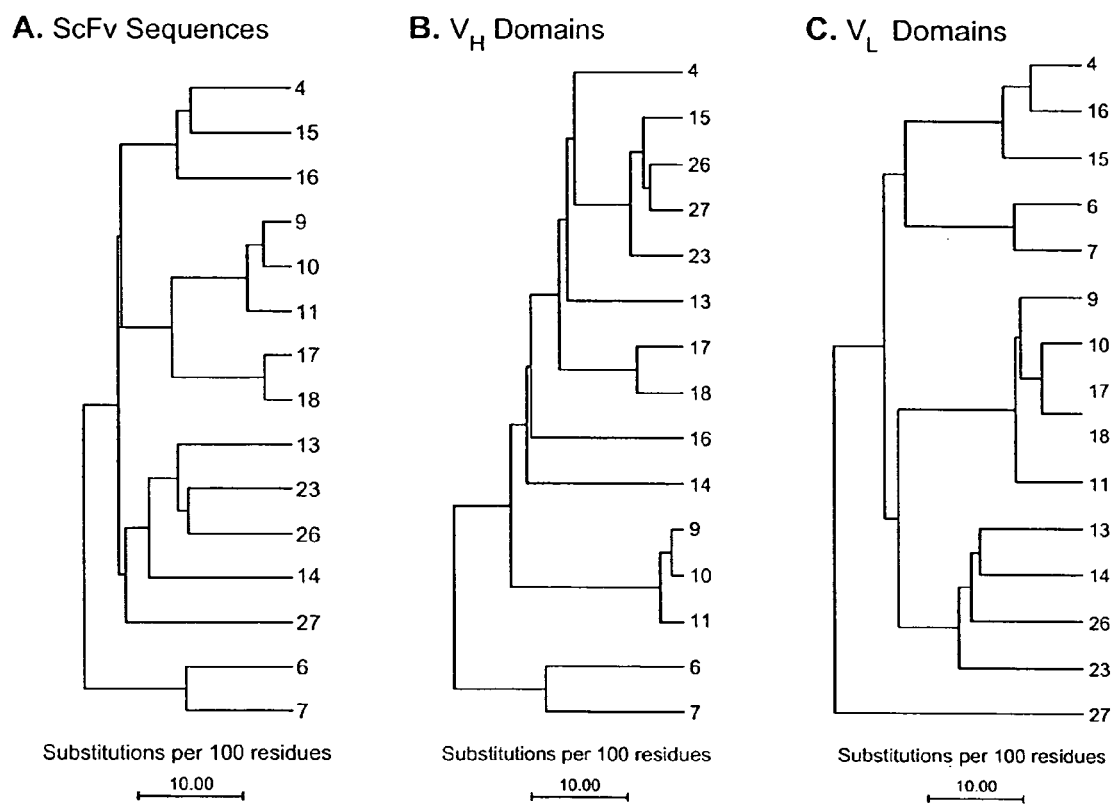
FIG. 5: This is an amino acid sequence comparison of 15 anti-IL-1$R_I$ scFv-phage clones. (A) This represents 15 unique scFv sequences (putative IL-1$R_I$ antagonists) with the slowest $k_{off}$ rates and their component $V_H$ (B) and $V_L$ (C) domains. Amino acid sequence comparison are represented as phylogram trees produced using an in-house MiniPileup program. Clone numbers are listed along the right side of the plots.

Table I lists the related V domain families and gene segments and corresponding sequences of the 15 selected clones. The heavy chains are highly diverse (FIG. 5B) with 8 different V$_H$ genes represented (Table I) out of a possible 54 (Tomlinson et al. (1995), *EMBO J.* 14:4628-4638.). The V$_H$3 family predominates (13/15) amongst these V$_H$ sequences. Strikingly, the light chains are virtually all of the λ (14/15) rather than κ (1/15) isotype. Sequence analysis of 100 individual clones from each unselected library revealed a significant bias in favor of λ over κ in the starting libraries, which may account for the preponderance of λ clones in our selected clones. Comparison of the sequences of the V$_H$ and V$_L$ regions of these clones revealed that many of the clones are closely related (FIG. 5). For example, clones C9, C10, and C11 utilize the same germline gene segments for heavy and light chain (V$_H$ DP38 and V$_L$ DPL11), as do C13 and C26 (V$_H$ DP47 and V$_L$ DPL3) (Table I). Nevertheless even clones with the most similar sequences (C9 and C10) differ from each other by at least 13 amino acid replacements.

Conversion of scFv-Phage Clones to scFv-Fc and IgG$_4$ Formats

More detailed characterization of the 15 selected scFv clones necessitated the expression and purification of antibody protein. We elected to reclone the 15 scFv clones listed in Table I into both scFv-Fc and IgG$_4$ formats, each being dimeric and bivalent antibody structures. Recoveries of IgG$_4$ proteins ranged from 0.4 to 7.0 mg/l as estimated by the absorbance at 280 nm and theoretical extinction coefficients calculated from the amino acid sequence of individual clones (data not shown). Recovery of those same clones in scFv-Fc format was 2-14 fold greater, ranging from 0.8 to 32.6 mg/l (data not shown).

Figure 6:
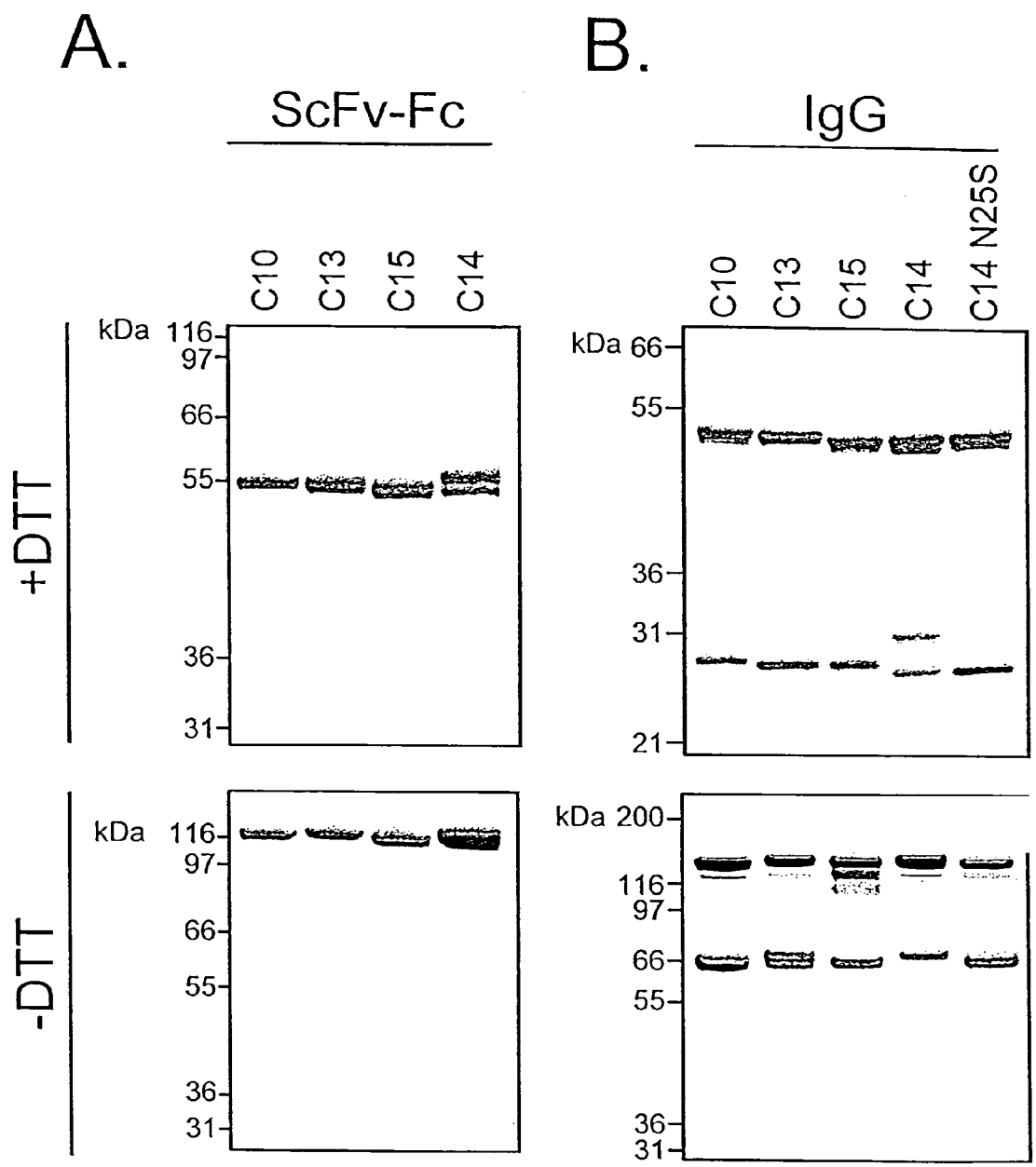
FIG. 6: This is SDS-PAGE analysis of purified scFv-Fcs and full-length antibodies (IgG proteins). Reduced (+DTT) and non-reduced (−DTT) acrylamide gels were used to resolve the purity of the most potent IL-1$R_I$ antagonist antibodies C10, C13, C14, and C15. Both (A) scFv-Fc and (B) IgG formats are shown for each of these clones. Molecular weight markers are indicated along the left side of the gels. The C14 glycosylation site mutant, C14 N25S, was only produced as an IgG$_4$. (C) The scFv sequence of clone C14 is shown with heavy chains (sequence before boldface type), light chains (sequence after boldface type), CDRs (underlined), the linker region (boldface type), and a potential N-linked glycosylation site (boxed).

Analysis of purified proteins on reduced and non-reduced PAGE revealed that scFv-Fc and IgG$_4$ molecules were ≧90% pure (FIG. 6A and 6B). Under reducing and non-reducing conditions, with the exception of C14, scFv-Fc molecules gave rise to a single major band of apparent molecular weight of 55 kDa and 120 kDa, respectively (FIG. 6A), as anticipated for these reducible disulfide-linked dimers. In contrast, IgG$_4$ preparations, with the exception of C14, migrated with 2 major bands of apparent molecular weight ~150 kDa and ~75 kDa under non-reducing conditions (FIG. 6B). This finding is consistent with the observation that intra-heavy chain disulfide bond formation competes with inter-heavy chain disulfide bond formation for IgG$_4$ molecules. Consequently IgG$_4$ preparations typically contain a variable mixture of covalent and non-covalent tetramers (Bloom et al., 1997; Angal et al., 1993; Schuurman et al., 2001). For clone C10, size exclusion chromatography was used to verify that the preparation behaved as a ~150 kDa molecule in solution, consistent with the presence of covalent and non-covalent tetramers. Under reducing conditions IgG$_4$ molecules give rise to bands of approximately 50 kDa and 28 kDa apparent molecular weight as expected for light and heavy chains (FIG. 6B).

C14 IgG$_4$ is notable in that two light chain bands were observed following SDS-PAGE under reducing conditions, as judged by N-terminal sequence analysis (FIG. 6B). The sequence of clone C14 is unusual in that it contains a potential N-linked glycosylation site (N25K26S27) beginning at position 25 of V$_L$ within the first complementarity determining region (CDR) (FIG. 6C). To investigate whether this site is glycosylated in the C14 IgG$_4$ molecule, an N25S variant of clone C14 (C14 N25S) was constructed in which the putative glycosylation site was removed. Under reducing conditions C14 N25S gives rise to a single light chain band (FIG. 6B). These data from C14 and C14 N25S in toto support the notion that ~50% of C14 light chains are glycosylated at the NKS site within the V$_L$ domain.

Functional Characterization of scFv-Fc and IgG$_4$ Proteins

The 15 scFv-clones converted to scFv-Fc and IgG$_4$ formats were assayed to identify the most potent IL-1R$_I$ antagonists and to assess the degree of functional correspondence between these antibody formats. First these clones were assessed for binding to cell-surface receptors by flow cytometry using K299 cells expressing human IL-1R$_I$. In scFv-Fc format, all clones except for C4, C9, C11, C16, C17, and C26 displayed significant binding to cell-surface human IL-1R$_I$. Likewise in the IgG$_4$ format, the same clones bound to cell-surface IL-1R$_I$. Based on these flow cytometry data, six clones (C4, C9, C11, C16, C17 and C26) were eliminated from further analysis.

Figure 7:
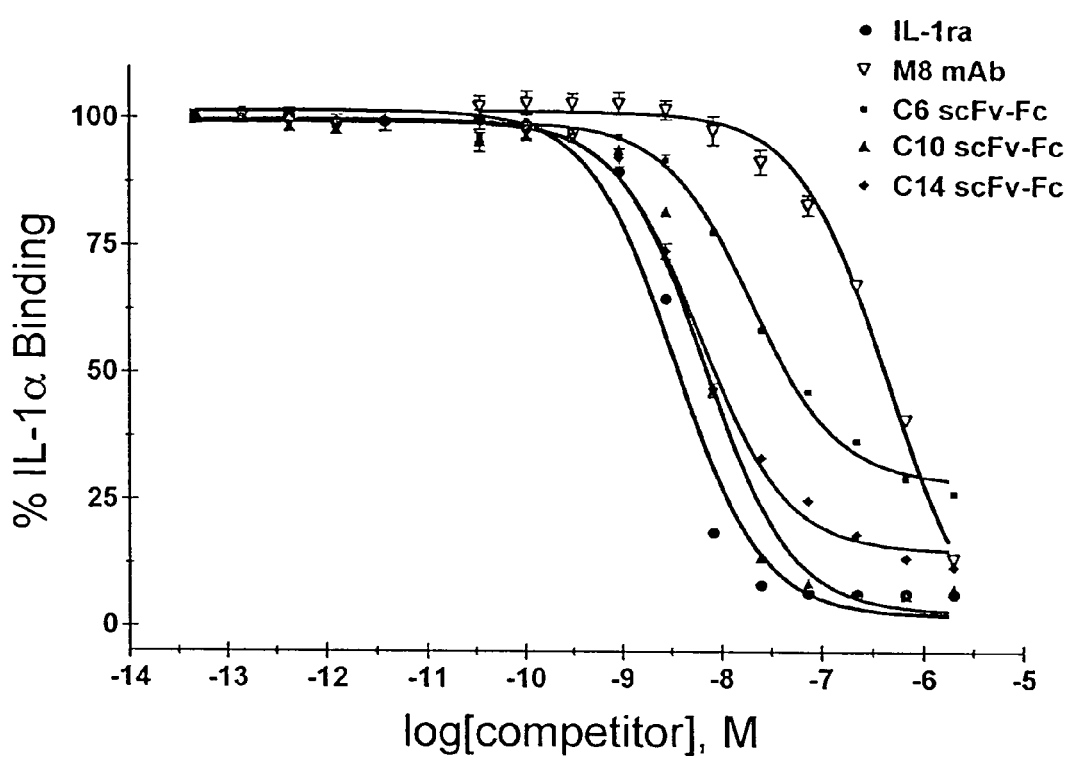
FIG. 7: This shows inhibition of IL-1 binding to IL-1$R_I$ by IL-1$R_I$ antibodies. Representative plots of competition-binding assays using Eu-labeled IL-1α and various competing molecules. All lead scFv clones were examined in this assay for the ability to compete with IL-1α and IL-1β for binding to immobilized IL-1$R_I$. IL-1α competition curves for the anti-IL-1$R_I$ antibody clones C6 (squares), C10 (upright triangles), C14 (diamonds), M8 mAb (inverted triangles), and IL-1ra (circles) competitors are shown in both the (A) scFv and (B) IgG$_4$ formats. Relative IC$_{50}$ values for each of the lead clones were calculated from these curves.
Figure 7:
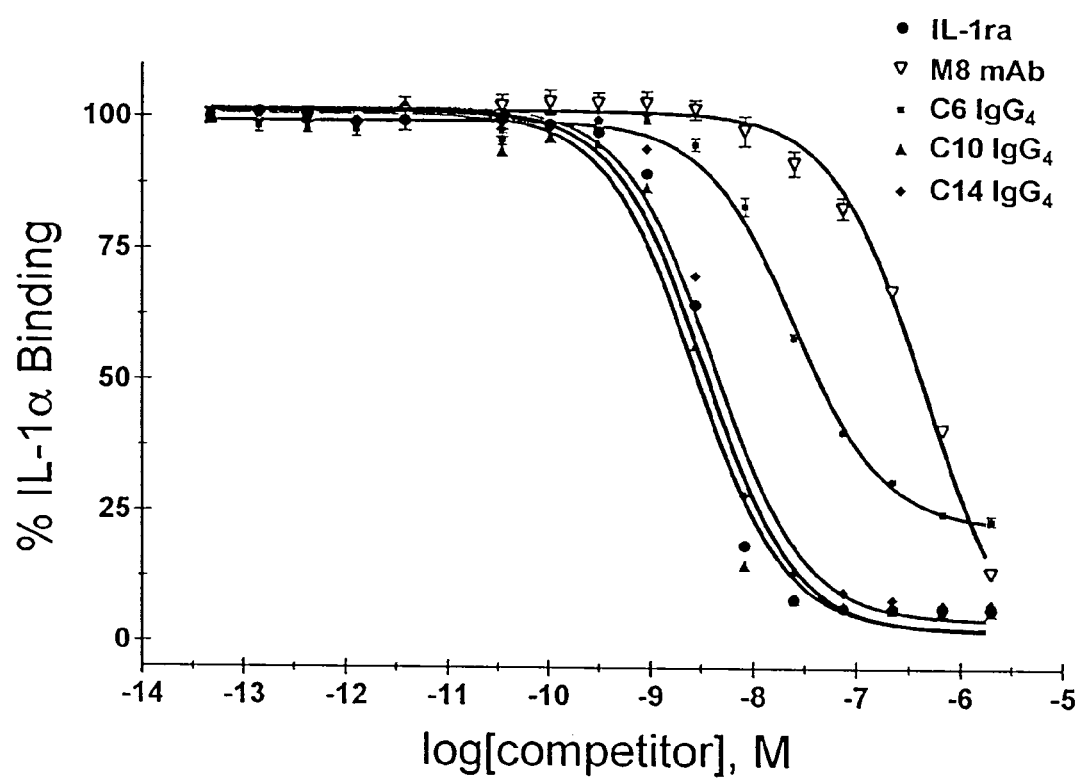

The remaining nine scFv-Fc and IgG$_4$ molecules (C6, C7, C10, C13, C14, C15, C18, C23 and C27) were next compared in competition binding assays for their ability to inhibit Eu-labeled IL-1α and IL-1β binding to IL-1R$_I$ ectodomain. Europium labeling of IL-1β slightly impairs its binding to human IL-1R$_I$ as judged by a 3-fold increase in K$_D$ to 3 nM estimated by Biacore (data not shown). With this in mind the IC$_{50}$ values reported here are interpreted as relative rather than absolute estimates of binding inhibition. In scFv-Fc format, clones C10, C13, C14, C15, C18 and C27 were the most potent inhibitors of IL-1α and IL-1α binding. Similar results were seen with these six clones in IgG$_4$ format. These six clones represent the lead clones and their relative IC$_{50}$ values are listed in Table II. Corresponding IC$_{50}$ values for clones as scFv-Fc and IgG$_4$ were within 3-fold of each other. Moreover, the most potent clones in scFv-Fc format were also the most potent in IgG$_4$ format and yielded IC$_{50}$ values similar to those obtained using IL-1ra as a competitor (Table II). The remaining three clones (C6, C7 and C23) showed significantly lower or no inhibition in this assay. FIG. 7 shows binding curves from two of the most potent clones (C10 and C14) in both scFv-Fc and IgG formats along side of one of the less potent clones (C6) and the weakly neutralizing M8 mAb.

TABLE II

Potency of lead anti-IL-1R$_I$ antibodies

| Format/ Clone | Protein yields[a] mg/l | Species cross reactivity[b] Human | Murine | Cyno | Ligand competition[c,d] IL-1α nM | IL-1β nM | NF-κB nuclear translocation[c,e] IL-1α nM | IL-1β nM | Binding affinity[f] K$_D$ nM |
|---|---|---|---|---|---|---|---|---|---|
| ScFv-Fc | | | | | | | | | |
| C10 | 10.2 | + | − | + | 1.6 | 1.8 | 380 | 440 | 60 |
| C13 | 7.8 | + | − | + | 1.4 | 1.8 | 600 | 900 | 430 |
| C14 | 8.8 | + | + | − | 6.4 | 3.0 | 620 | 310 | 470 |
| C15 | 32.6 | + | − | + | 2.0 | 1.6 | 780 | 480 | >5000 |
| C18 | 20.0 | + | + | + | 20.1 | 8.7 | NI | NI | 2900 |
| C27 | 7.6 | + | − | − | 35.5 | 12.4 | NI | NI | 2200 |
| IgG$_4$ | | | | | | | | | |
| C10 | 2.4 | + | − | − | 4.5 | 2.6 | 26 | 18 | 64 |
| C13 | 1.1 | + | − | + | 2.9 | 1.8 | 81 | 40 | 540 |
| C14 | 2.3 | + | + | − | 3.3 | 2.9 | 215 | 101 | 560 |
| C14N25S | 3.4 | + | + | − | 4.3 | 2.3 | 247 | 129 | 1280 |
| C15 | 4.7 | + | − | + | 3.2 | 2.8 | 113 | 103 | —[g] |
| C18 | 7.0 | + | + | + | >50 | >50 | NI | NI | >5000 |

TABLE II-continued

Potency of lead anti-IL-1R$_I$ antibodies

| Format/ Clone | Protein yields[a] mg/l | Species cross reactivity[b] | | | Ligand competition[c,d] | | NF-κB nuclear translocation[c,e] | | Binding affinity[f] K$_D$ |
|---|---|---|---|---|---|---|---|---|---|
| | | Human | Murine | Cyno | IL-1α nM | IL-1β nM | IL-1α nM | IL-1β nM | nM |
| C27 | 2.2 | + | − | + | 14.0 | 7.9 | NI | NI | >5000 |
| IL-1ra | n.d. | n.d. | n.d. | n.d. | 3.1 | 2.5 | 0.4 | 0.2 | 0.039[h] |

[a] Protein yields estimated from A$_{280}$ and corresponding theoretical extinction coefficient estimated using the predicted amino acid sequence of clones. n.d., not determined.
[b] Strong (+), weak or insignificant (−) binding of antibodies to IL-1R$_I$ from different species was observed by flow cytometry using K299 cells (human IL-1R$_I$), transfected CHO (murine IL-1R$_I$) or transfected COS-1 (cynomolgus IL-1R$_I$) cells.
[c] Relative IC$_{50}$ values estimated from a non-linear least squares four-parameter fit.
[d] Experiments were performed using biotinylated human IL-1R$_I$ ectodomain immobilized on streptavidin-coated microtiter plates.
[e] Experiments were undertaken using human ligands and HeLa cells expressing human IL-1R$_I$. NI, not inhibited.
[f] k$_{off}$/k$_{on}$ as determined by SPR. Experiments were conducted with scFv-Fc or IgG$_4$ captured on a goat anti-human Fc antibody-coupled CM5 chip to measure monovalent interactions between the IL-1 receptor (analyte) and each antagonist candidate (ligand).
[g] Does not fit to a 1:1 Ligand binding model
[h] Binding affinity of soluble IL-1ra to receptor was determined by SPR using IL-1R$_I$-Fc captured on a goat anti-human Fc antibody-coupled CM5 chip (D. Friend).

Figure 8:
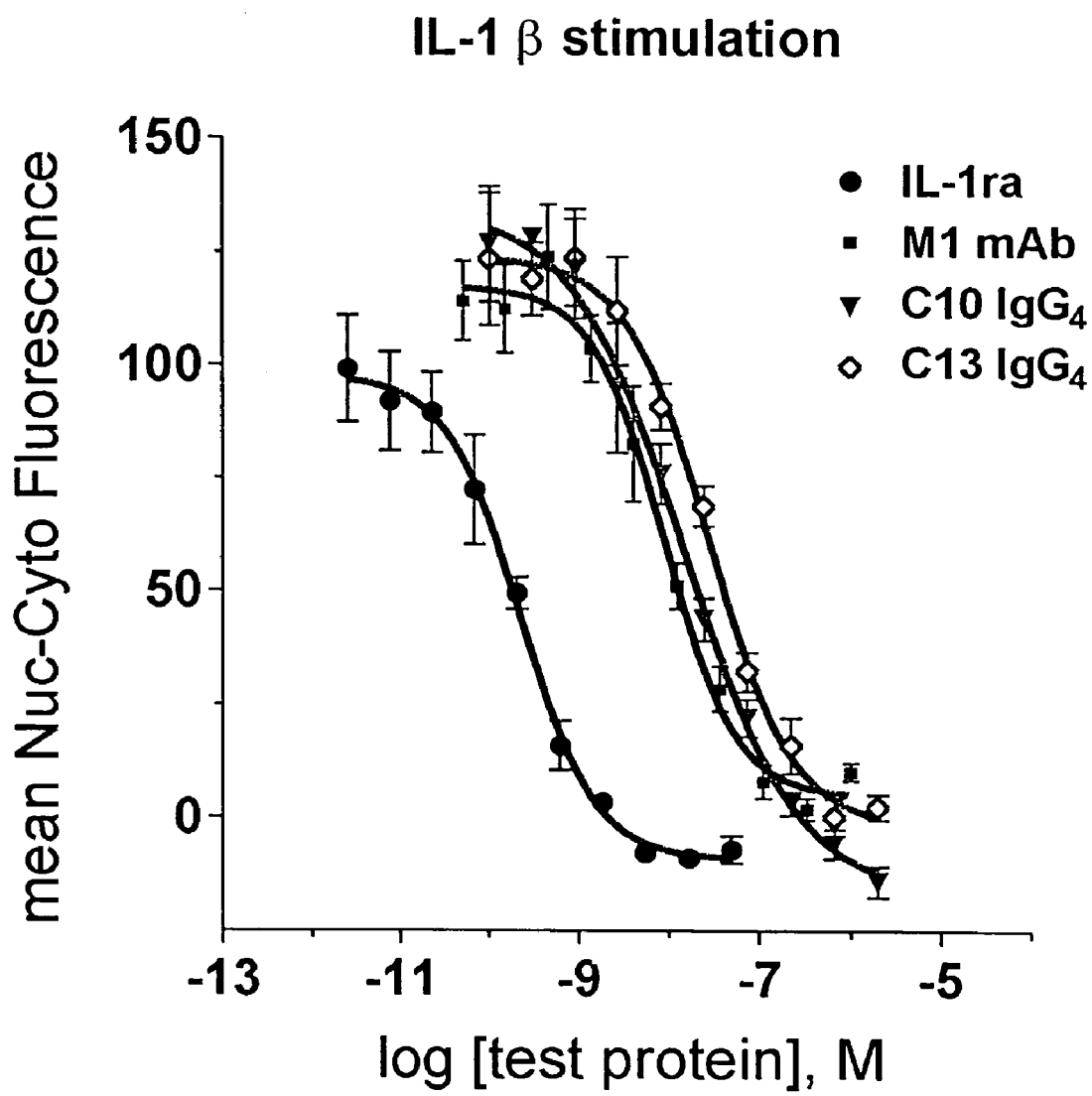
FIG. 8: This shows inhibition of NF-κB nuclear translocation in HeLa cells by anti-IL-1$R_I$ IgG$_4$ proteins. HeLa cells expressing hu IL-1$R_I$ were stimulated with 12 pM hu IL-1α or IL-1β (40 minutes, 37° C.) in the presence of various concentrations of anti-IL-1$R_I$ antibodies. After stimulation, NF-κB and cell nuclei were visualized using fluorescence stain, and fluorescence was measured within the cell nucleus and cytoplasm. Data are expressed as the difference between the mean nuclear and mean cytoplasmic fluorescence. Representative plots show the ability of C10 IgG$_4$ (triangles), C13 IgG$_4$ (diamonds), M1 mAb (squares), and IL-1ra (circles) competitors to inhibit IL-1β activity.

The biologic potency of the six lead clones as receptor antagonists was assessed by measuring their impact on IL-1α and IL-1β induced NF-κB nuclear translocation within HeLa cells. In both scFv-Fc and IgG$_4$ formats, four clones (C10, C13, C14, C15) were identified that significantly inhibited both IL-1α and IL-1β induction of NF-κB translocation. In scFv-Fc format these clones yielded IC$_{50}$ values from 310 to 900 nM (Table II). These same clones in IgG$_4$ format were 3 to 24-fold more potent (reduction in IC$_{50}$ values) than scFv-Fc molecules at blocking ligand-dependent signaling (Table II). There is good agreement between IL-1α and IL-1β IC$_{50}$ values and none of the clones examined inhibited binding of one ligand but not the other (Table II). In this bioassay, C10 IgG$_4$ is the most potent antagonist of IL-1α (26 nM IC$_{50}$) and IL-1β (18 nM IC$_{50}$; Table II). FIG. 8 shows the binding curves for two of the lead clones that inhibit NF-kB translocation compared to the M1 neutralizing Ab and IL-1ra. Although four of the lead clones are potent antagonists of IL-1R activity in this assay, IL-1ra is significantly more potent (FIG. 8 and Table II).

To determine whether glycosylation of the light chain of C14 impacts its ability to function as an antagonist, C14 IgG$_4$ and its N25S variant were directly compared in both the ligand competition and NF-κB nuclear translocation assays. Results of the ligand competition assay indicate that C14 and C14 N25S behave similarly when competing for IL-1R$_I$ binding with IL-1α and IL-1β. In fact C14 and C14 N25S yielded nearly identical IC$_{50}$ values in this assay (Table II). In the NF-κB assay, C14 and C14 N25S were equipotent at inhibiting IL-1 induced translocation of NF-κB (Table II). These findings indicate that glycosylation of the light chain does not impact the function of C14 IgG$_4$.

SPR experiments were performed on the lead antagonistic clones to determine their binding affinity for soluble IL-1R$_I$ and to examine whether the potency of the IgG$_4$ molecules in the NF-κB assay relates to binding affinity. Examination of the results of these affinity measurements revealed broadly similar K$_D$ values for these clones in both IgG4 and scFv-Fc formats (Table II). C10 was found to be the highest affinity clone in both formats having a K$_D$ of approximately 60 nM in each case. All other clones showed significantly lower binding affinities to human IL-1R$_I$ compared to C10 (Table II). These data appear consistent with the NF-κB assay in which C10 was also the most potent clone. Based on the results of these measurements, binding affinity does not offer a plausible explanation for the superior potency of IgG$_4$ molecules over scFv-Fc for these clones in the NF-κB assay (see Discussion; Table II).

Binding to cell surface IL-1R$_I$ from rodents and primates are highly desirable properties of IL-1R$_I$ antagonist antibodies intended for preclinical development. These properties may allow efficacy and/or toxicology studies to be potentially undertaken with the same antibody clone selected for clinical development. For this reason, we used FACS analysis to screen our six lead clones for cross-reactivity with IL-1R$_I$ from cynomolgus monkey and mouse. As IgG molecules, four of six lead clones (C13, C15, C18 and C27) bound significantly to cynomolgus IL-1R$_I$ expressed on the surface of transiently transfected CV-1 and HEK 293 cells (Table II). The ability to bind cynomolgus receptor was similar for the lead clones in both antibody platforms with the exceptions of C10 and C27. C10 bound to receptor as an scFv-Fc, but did not significantly bind cynomolgus IL-1R$_I$ in IgG format (Table II). Likewise C27 bound to cynomolgus receptor as an IgG, but not as an scFv-Fc. This high frequency of antibodies that cross-react with human and cynomolgus IL-1R$_I$ likely reflects the close identity between these receptor ectodomains (~94% sequence identity). In addition to the four clones that were observed to bind cynomolgus IL-1R$_I$, two of the six antagonist clones in IgG$_4$ format (C14 and C18) bound murine IL-1R$_I$ expressed on the surface of CHO cells (Table II). This lower frequency of antibody cross-reactivity between human and murine IL-1R$_I$ ectodomains appears consistent with these receptor sequences being more distantly related (~64% identity). Interestingly, C14 bound to cell surface expressed murine and human, but not cynomolgus IL-1R$_I$.

Discussion

Initial identification of 39 unique scFv-phage clones whose binding to IL-1R$_I$ was impaired by prebound IL-1 was accomplished using a modified binding inhibition assay format. This assay approach was used in place of a traditional binding competition assay because scFv concentrations on phage molecules are too low and variable to compete effectively for IL-1 binding to receptor. A priori, scFv-phage clones that are weakly inhibited from binding receptor in the presence of ligand might include highly potent clones that compete effectively with ligand as well as clones whose receptor binding is minimally impaired by ligand. Two steps were taken to reduce the risk of discarding the most potent clones in this initial screening assay. First, plates were preblocked with ligand to reduce the risk of scFv-phage out-competing ligand. Second, we adopted a low threshold of inhibition (>25% inhibition) to consider clones for further analysis.

In addition to selecting lead IL-1R$_I$ antagonist antibodies, one of the objectives of our study was to determine if scFv-Fc molecules could be predictive of IgG properties. Each of the 15 scFv-phage clones listed in Table I was converted to scFv-Fc and IgG formats to allow direct comparison of these two formats. ScFv-Fc molecules shown to be equipotent to their corresponding IgG molecules could be used as a rapid screening tool to eliminate low potent clones from further characterization, thus reducing the number of putative antagonist clones needed to be converted to IgG format. ScFv-Fc molecules are well suited as initial screening tools for two important reasons. First, scFv-Fc molecules require much less time to produce than IgG molecules for reasons already mentioned. Second, an scFv-Fc gives rise to higher protein yields than its corresponding IgG (up to 14 fold greater; Table II). Furthermore, current methods for high-throughput IgG production do not consistently yield sufficient protein for functional characterization studies.

Direct comparison of the 15 scFv clones expressed as both scFv-Fc and IgG molecules revealed striking similarities between these two antibody formats. First, flow cytometry studies identified the same nine clones in both formats as binders to cell-surface human IL-1R$_I$ (data not shown). Second, ligand competition binding assays performed on these nine clones yielded similar IC$_{50}$ values for both formats with C10, C13, C14, C15, C18 and C27 being most potent (Table II). Third, the same clones (C10, C13, C14 and C15) in both scFv-Fc and IgG$_4$ formats were the most potent inhibitors of NF-κB nuclear translocation (Table II). Moreover, our most potent clone, C10, demonstrated the greatest relative inhibition in both formats (Table II). Fourth, all of our most potent antibody clones have similar monovalent binding affinities in both formats (Table II). Finally, four of the six lead clones bound to either murine or cynomolgus IL-1R$_I$ in FACS studies both as an scFv-Fc and an IgG$_4$ (Table II).

The most striking difference between the two antibody platforms is apparent upon quantitative examination of the NF-κB translocation assay results. Although C10, C13, C14 and C15 were observed to inhibit NF-κB translocation in both formats, these clones are significantly more potent inhibitors in IgG format (Table II). This finding is unexpected considering that these same clones have similar binding affinities (to monomeric receptor) in both scFv-Fc and IgG formats (Table II). Despite differences in functional potency in the cell based assay, the correspondence between anti-IL-1R$_I$ scFv-Fc and IgG properties is sufficiently robust to warrant further exploration of the scFv-Fc format as a screening tool given the greater ease with which scFv-Fc molecules can be produced. Further engineering of the scFv-Fc format may further improve the similarities between scFv-Fc and IgG properties. For example, addition of linker regions or additional domains between the Fc and scFv portions of an scFv-Fc that more closely match the conformation of an IgG may permit bivalent interactions to IL-1R$_I$ and increase antagonist potency.

During this study we have focused on the in vitro identification of anti-IL-1R$_I$ antibodies with potent antagonist activities, strong binding affinities and species cross reactivity as these characteristics are likely to be of paramount importance in developing a therapeutic antibody. Results from the NF-κB assay identified IgG$_4$ C10 as the most potent IL-1R$_I$ antagonist despite relatively modest monovalent receptor binding affinity (K$_D$~60 nM) compared to IL-1ra (K$_D$~0.04 nM). Comparison of IL-1ra and IgG$_4$ C10 receptor affinity and antagonist potency suggest that relatively high affinity is not an absolute prerequisite for the functional potency of these clones (Table II). It is important to consider that the optimal affinity for a therapeutic antibody is not known, and, significantly, high affinity binders are not always needed to achieve the best antibody potency (Adams et al. (2001), *Cancer Res.* 61:4750-4755). Additionally, the superior in vitro potency of IL-1ra in our assays does not indicate that IL-1ra will outperform a high affinity antagonist IL-1R$_I$ antibody in vivo. As discussed earlier, the greatest potential advantage of using an anti-IL-1R$_I$ antibody over IL-1ra (anakinra) as a therapeutic is the substantial increase in terminal half-life. Moreover it is desirable and common practice to increase the binding affinity of therapeutic antibody candidates prior to clinical development using affinity maturation. This process involves introducing mutations into antibody complementarity determining regions and screening resultant antibodies for improved binding affinity and/or biological potency. Affinity maturation has been successfully used to significantly improve the binding affinity of numerous antibodies. Yang et al. (1995), *J. Mol. Biol.* 254:392-403; Pini et al. (1998), *J. Biol. Chem.* 273:21769-21776; Schier et al. (1996), *J. Mol. Biol.* 263:551-567.

EXAMPLE 2

Selection of Intrabodies that Bind to Interleukin-1 Receptor (IL-1R$_I$)

The following experiment was aimed at determining whether a phage antibody library that had been panned to increase the proportion of antibodies that bind to IL-1R$_I$ could be further enriched for such antibodies by performing a positive functional selection in IL-1β-sensitive mammalian cells transduced with an intrabody expression library. The selection was based on the observation that A375 cells (ATCC CRL-1619), which are a melanoma cell line that expresses IL-1R$_I$, are killed in the presence of IL-1β and the assumption that A375 cells that do not express IL-1R$_I$ would not be sensitive to the actions of IL-1β, since IL-1R$_I$ is required for IL-1β signaling. An intrabody that binds to IL-1R$_I$ might prevent its export to the cell surface, thereby making cells insensitive to IL-1β. Thus, A375 cells are "target cells," as meant herein.

A naïve human antibody phage scFv library was subjected to three rounds of panning with IL-1R$_I$ as described above in Example 1. Phage plasmid DNA was stored after each round of panning. After the third round of panning, individual antibodies were tested for IL-1R$_I$ binding as described in Example 1. Sequences of 27 antibodies that displayed binding to IL-1R$_I$ are used below to compare to the antibodies recovered in the following functional selection.

The coding sequences of the scFv's from phage plasmid DNA from the first round of panning were subcloned into a lentiviral intrabody vector for expression as intracellular scFv-Fcs, which comprised an Fc region fused to the scFv and an intracellular localization sequence. Viral particles assembled using these constructs were used to transduce IL-1β-sensitive A375 cells. Intrabody-transduced A375 cells were treated with IL-1β. After 2 to 3 days, more than 99% of the cells died. Surviving cells were recovered, and allowed to expand in culture in the absence of IL-1β for about a week, at which time they were again treated with IL-1β. This process was repeated four times in all. After 4 such rounds of selection with IL-1β, surviving cells were expanded, and their genomic DNA was isolated. The intrabody sequences were amplified by PCR, and DNAs encoding the scFv domains were subcloned into a scFv-Fc expression vector suitable for production of secreted soluble scFv-Fcs comprising an scFv and an Fc region by transient transfection.

Figure 9:
FIG. 9: This is a comparison of the scFv sequences obtained subsequent to functional selection in mammalian cells with sequences of known IL-1R$_1$-binding scFv's using the program PileUp. The lengths of the vertical lines are proportional to the number of amino acid differences between the sequences. Sequences are represented by either a dot, for sequences identified in this study, or an asterisk, for previously-identified scFv's that bind to IL-1R$_1$.

Plasmid DNA from 192 of these *E. coli* transformants was sequenced, and the sequences were compared to the sequences of the panel of 27 known IL-1$R_I$-binding scFv's from Example 1. Each of these antibodies from Example 1 is represented as an asterisk in FIG. 9, and the test sequences are represented by dots. Results are displayed in FIG. 9 as a dendrogram generated by the computer software PILEUP (Feng and Doolittle (1987), *J. Mol. Evol.* 25:351-360). Two of the selected antibodies were identical to the known IL-1$R_I$-binding antibodies. One had only a single amino acid difference from a known IL-1$R_I$-binding antibody, and a number had very high percent identities with known IL-1$R_I$ binding scFv's. FIG. 9. Moreover, many of the selected antibodies were the same or very similar to each other in sequence, which also indicates that selection had taken place. Twenty of the scFv-Fc expression constructs were transfected into 293MSR cells in order to produce secreted, soluble scFv-Fcs. Only 9 of the 20 transfectants produced an amount of scFv-Fc detectable on a Western blot. Of these, 7 scFv-Fcs bound to type I IL-1$R_I$-expressing 293 cells, but not to control 293 cells, as shown by FACS analysis.

For comparison, 96 of the nucleic acid sequences encoding scFv's resulting from the first round of panning the phage library were determined. These did not display similarity to each other and to the known IL-1$R_I$-binding antibodies as high as that shown by the antibodies isolated from the A375 cell selection described above. Compare FIG. 10 to FIG. 9. In addition, the 12 scFv's with the highest degree of similarity to known IL-1$R_I$-binding antibodies were subcloned into a vector suitable for production of secreted, soluble scFv-Fcs. These scFv-Fc vectors were used to transfect 293MSR cells. Only two of the twelve transfectants produced an amount of scFv-Fc protein detectable on a Western blot. Neither of these scFv-Fcs bound to IL-1$R_I$-expressing 293 cells as determined by FACS analysis. These results suggest that the selection in A375 cells resulted in a very substantial enrichment for antibodies that bind to IL-1$R_I$. In addition, due to the nature of the selection scheme, it is possible that the selected antibodies interfere with the interaction between IL-1$R_I$ and IL-1β.

EXAMPLE 3

Effective Suppression of Gene Expression by Intracellular Antibodies Comprising an Fc Region Two single chain Fv clones selected for their ability to bind human interleukein 4 receptor (IL4R) alpha chain were chosen for assessment of their ability to function as intrabodies. Clone 63 antibody is a high-affinity, neutralizing (i.e. blocks IL4 interaction with IL4R alpha) anti-IL4R alpha antibody, while clone e11 antibody has a lower affinity and is not a neutralizing antibody. Three different intracellular localization schemes were assessed. The first utilized a C-terminal, 6-amino acid ER localization sequence (SerGluLysAspGluLeu), the second utilized the transmembrane domain of human IgM, and the third utilized the transmembrane and cytoplasmic domains of human CMV open reading frame UL16. Intrabody expression cassettes were constructed as scFv's and scFv-Fcs. The scFv-Fc forms utilized a human IgG1 Fc domain between the scFv and intracellular localization sequences.

Figure 11:
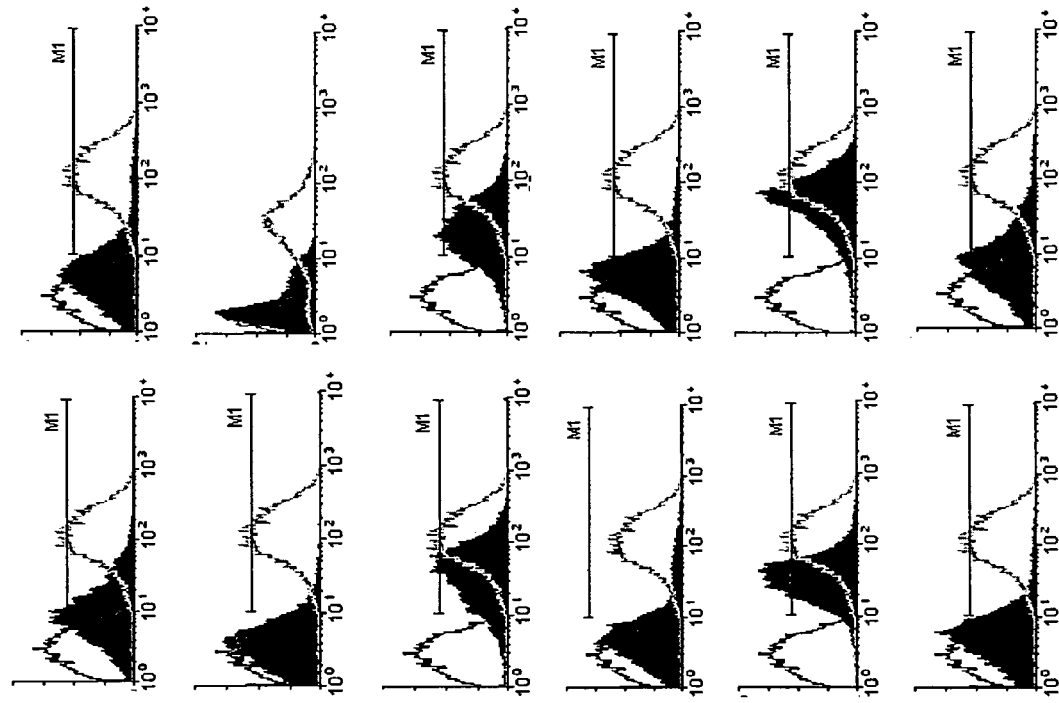
FIG. 11: On the left are diagrammed six lentiviral constructs (A-F) encoding intracellular antibodies that bind to interleukin 4 receptor (IL4R). The markings signify as follows: signal sequence, ▧; scFv, ■; myc tag, ▩; ER retention sequence (SEKDEL), ▤; IgM transmembrane domain (which functions as an intracellular retention sequence), ▬; cytomegalovirus UL16 transmembrane and cytoplasmic domains (which function as an intracellular retention sequence), ▦; and IgG1 Fc region, ▥. On the right are shown the results of FACS analyses of IL4R-expressing cells transfected with the constructs shown at left using a primary antibody that binds to IL4R and a fluorescently-labeled secondary antibody that binds to the primary antibody. The FACS scans are from cells transfected with constructs made with antibody-encoding sequences from either clone 63 (left column) or clone e11 (right column). Intensity of fluorescence is shown on the horizontal axis, and the number of cells having that level of fluorescence is shown on the vertical axis. The gray line (which, in every case, defines a hill-shaped curve to the right of that defined by the black line) represents untransfected cells in the presence of both primary and secondary antibodies. The filled area represents cells transfected with the constructs shown at left in the presence of both primary and secondary antibodies. The black line shows the background signal in the presence of secondary antibody alone.
Figure 11:
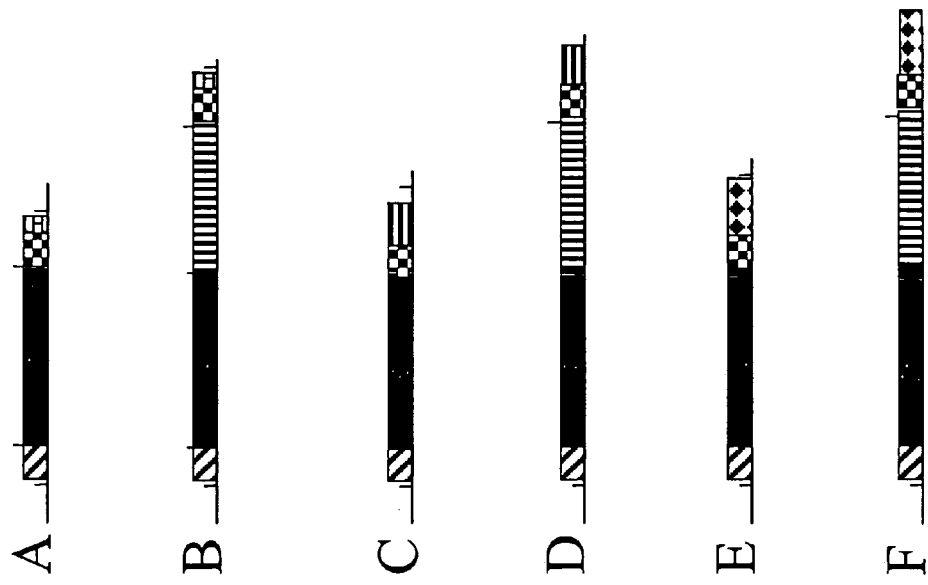

To assess the ability of each construct to inhibit the cell surface expression of IL4R, each scFv coding domain was ligated to the appropriate C-terminal coding sequences, and assembled in a lentiviral expression construct as diagrammed on the left of each panel of FIG. 11. Lentiviral particles were prepared from each construct, and used to transduce cell line CTLL-D, a murine cytotoxic T lymphocyte (CTL) line that was engineered to constitutively express high levels of human IL4R alpha. Following transduction, the effectiveness of each intrabody construct was measured by FACS analysis of surface IL4R levels in transduced cells. These FACS scans (shown to the right of each construct in FIG. 11) were performed with cells transduced with each of the two forms of each construct, those expressing a clone 63-derived variable region (left) and those expressing a clone e11-derived variable region (right). All 12 constructs were effective in reducing cell surface expression of IL4R (FIGS. 11A-11F). Further, in each case, the scFv-Fc form of each construct was more effective than the corresponding scFv form in reducing surface IL4R levels. These results indicate that scFv-Fc forms of intrabodies, utilizing the human IgG1 Fc domain as a dimerizing domain, are more effective than scFv forms in inhibiting the cell surface expression of IL4R.

EXAMPLE 4

Identification of a Proapoptotic Antibody

The following screening procedure shows that proapoptotic antibodies can be identified using the methods of the invention. In a first step, a phage scFv library was subjected to a pre-selection for binding to a colon cancer cell line, Colo205. The regions encoding the scFv's from the nucleic acids of these selected phage were excised and cloned into a vector pDC409a-huG1Fc-TM, which is like pDC409a-huG1Fc described above in Example 1 except that it additionally encodes a transmembrane domain. This vector allows high expression of the cell surface scFv-Fcs it encodes. Using the automated methods discussed above, individual *E. coli* transformant colonies were picked robotically and cultured. Thereafter, groups of 36 colonies were pooled, and plasmid DNA was prepared from each pool. Optimal pool size can be determined empirically. A pool size of 48 was also tried, but no positive results were obtained in this trial. Plasmid DNA from each pool was used to transfect Cos1 cells, which was also done robotically. To perform the screening, Cos1 cells expressing the cell surface antibodies were mixed with Colo205 cells, and a whole cell caspase activity assay marketed by BeckmanCoulter (CELLPROBE™ HT Caspase-3/7 Whole Cell Assay, part nos. 390763 or 390773) was performed. The assay utilizes a short peptide substrate of Caspase 3 that can be specifically cleaved by caspase 3, an event that is detected as a fluorescent signal because cleavage unblocks a rhodamine moiety that is fused to the peptide. The fact that this substrate can enter cells through their membranes makes it possible to perform the assay using whole cells.

Figure 10:
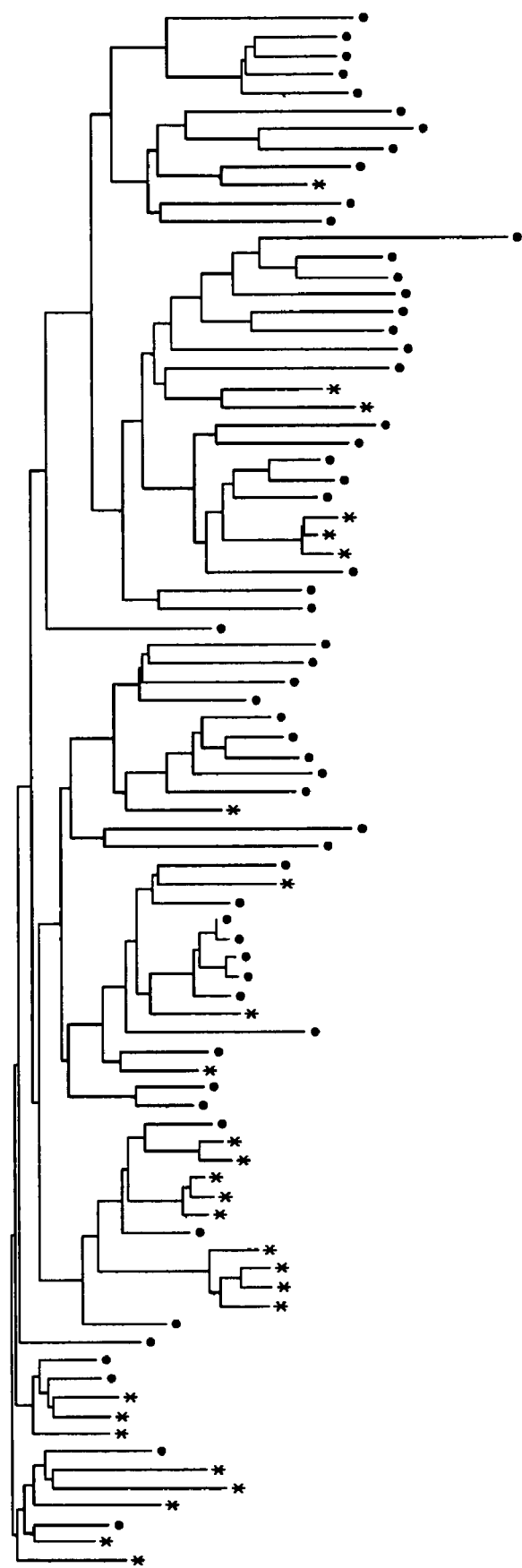
FIG. 10: This is a comparison of the scFv sequences obtained after one round of panning of a phage scFv library with sequences of known IL-1R$_1$-binding scFv's. As in FIG. 9, the lengths of the vertical lines are proportional to the number of amino acid differences between the sequences. Sequences are represented by either a dot, for sequences identified in this study, or an asterisk, for previously-identified scFv's that bind to IL-1R$_1$.
Figure 12B:
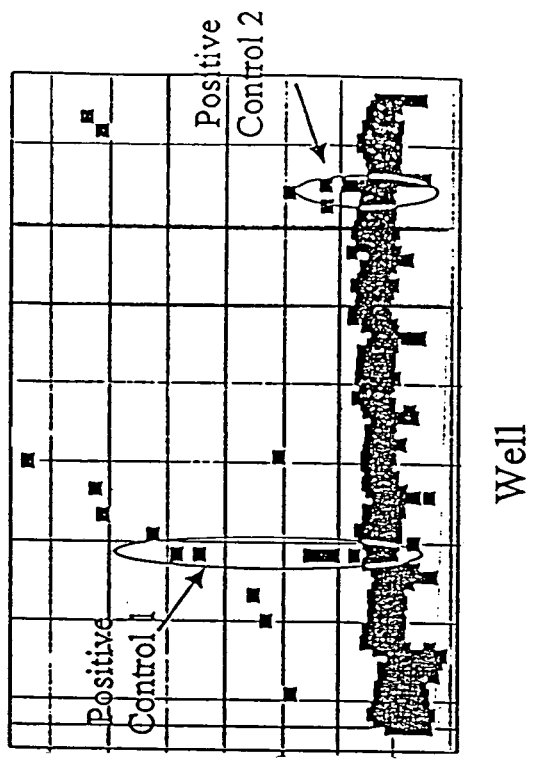
FIG. 12: This shows the results of caspase assays performed with a mixture of Colo205 cells and cells expressing the scFv-Fcs being tested on their surface. The vertical axis shows fluorescence, and the horizontal axis indicates the microtiter well being tested. Results from numerous microtiter plates are aggregated in this figure. Panel A shows the initial screening, and Panel B shows a subsequent rescreening of the pool of antibodies expressed in the positive pool 30E1 identified in Panel A.
Figure 12A:
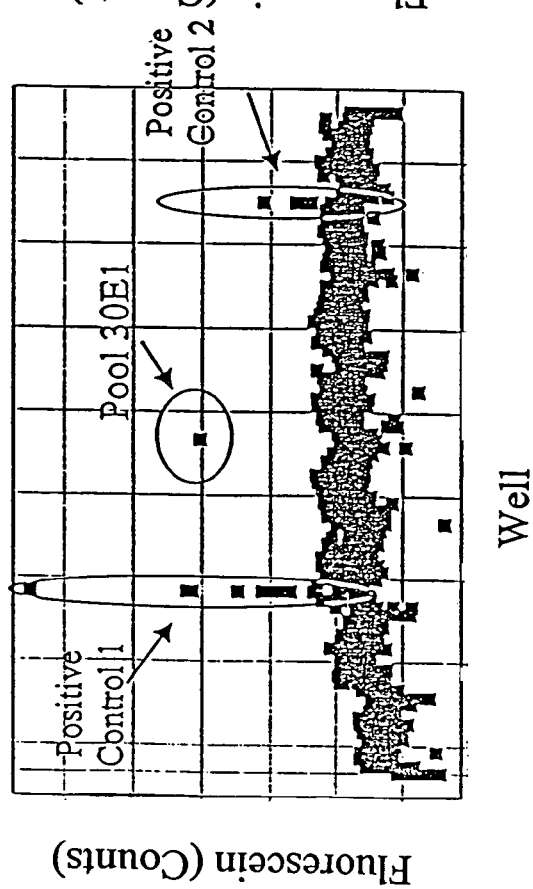

In all, scFv-Fcs from about 300,000 independent *E. coli* transformants were screened in pools of 36. As is known in the art, caspase activity is indicative of apoptosis or programmed cell death. Two positive controls were included comprising Cos1 cells transfected with a TRAIL receptor type 2 (TRAIL-R2) cell surface antibody known to induce caspase activity in Colo205 cells. See Walczak et al. (1997), EMBO J. 16(17):5386-5397; Griffith et al. (1999), *J. Immunol.* 162:2597-2605. One positive well, pool 30E1 of FIG. 12A, did not correspond to a positive control. The *E. coli* plasmid DNA corresponding to this well was used to generate a panel of *E. coli* transformants, 290 of which were used for transfections to generate a panel of 290 transfectants, each expressing a single cell-surface antibody. These were tested using the same caspase assay. As shown in FIG. 12B, 10 positive clones other than the positive controls were identified, which is approximately the number expected if the DNA encoding the positive antibody were 1/36 of the DNA in the *E. coli* plasmid DNA pool. Thus, this experiment shows that antibodies having a therapeutically relevant biological function can be screened for using the methods of the invention. Moreover, the identity of the antigen to which the selected antibodies bind need not be known.

Further screening of 320,000 scFv-Fcs with these methods using pool sizes of 36 and 48 led to the isolation of five positives comprising nucleic acids encoding three different antibodies, all of which bound to TRAILR2. As mentioned above, some TRAILR2 antibodies were already known to induce apoptosis and were used as positive controls in these experiments. Thus, these results suggest that antibodies that induce apoptosis can be isolated using the methods described herein.

EXAMPLE 5

Identification of Antibodies that Inhibit Proliferation of Cancer Cells

The following screening procedure shows that soluble antibodies that can inhibit proliferation of Colo205 cells can be identified using the methods of the invention. The process was performed as follows. A large group of phage-displayed scFv antibodies was combined with primary human umbilical vein endothelial cells (HUVEC) that expressed green fluorescent protein (GFP) and CD25. Nucleic acids encoding GFP and CD25 had been introduced by transduction using a lentiviral vector containing sequences encoding these proteins. The mixture of cells and antibody-expressing phage was centrifuged to remove the cells and the phage that bound to them. Thereafter, this depleted phage library, i.e., the phage in the supernatant, was subjected to either of two procedures.

In a first procedure, the depleted phage library mixed with Colo205 cells expressing GFP and CD25 (genes encoding which had been introduced via transduction). Then Colo205 cells and phage that bound to them were separated from the non-binding phage by centrifugation. The phage were then eluted from the Colo205 cells.

In an alternate second procedure, the depleted phage library was combined with Colo205 cells expressing GFP and CD25 along with HUVEC. A murine antibody against CD25 was added to this mixture, as were magnetic beads coated with an antibody against the constant region of the murine antibody. The Colo205 cells were thus isolated using a magnet, and phage that bound to them were eluted and then mixed again with Colo205 cells expressing GFP and CD25. The Colo205 cells, along with the phage that bound to them, were then isolated by centrifugation. The phage were then eluted.

Phage isolated using either the first or second procedure were then amplified by propagation in *E. coli* and thereafter subjected to an additional round of panning with Colo205 cells to enrich again for phage that bind to Colo205 cells. DNA was isolated from these phage and a NcoI to NotI fragment encoding the selected scFv's was subcloned into the vector pcDNA5/FRT-TM, which had been cleaved with PciI and NotI (shown in FIG. 2). Plasmid DNA from the pool of *E. coli* transformants resulting from this ligation, along with a second vector encoding FLP recombinase, was used to transfect CHO cells comprising an FRT site. The transfected cells were selected in hygromycin for one week. Subsequently, transfectants expressing an Fc region on their cell surface were isolated by FACS and deposited in small pools (about 10 to 20 cells per pool) in 96 well microtiter plates.

Figure 13:
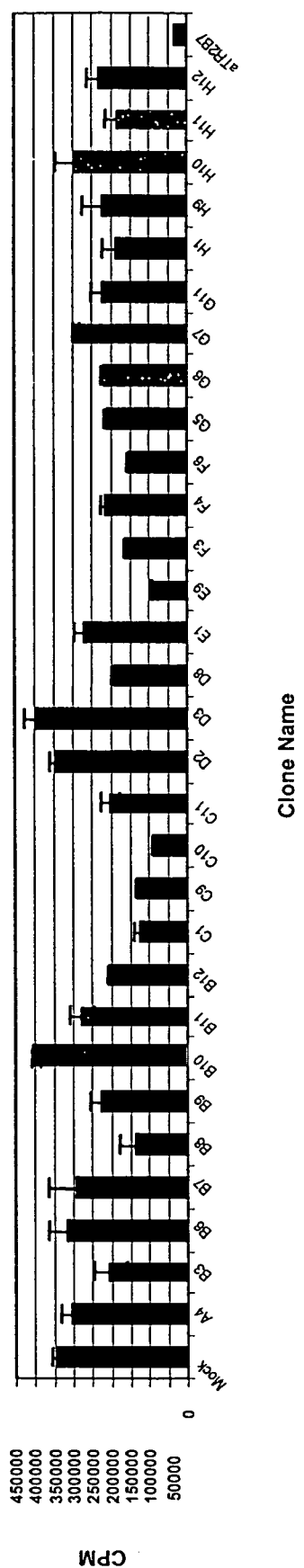
FIG. 13: This is a bar graph showing the results of an assay testing secreted, soluble antibodies for their effects on the proliferation of Colo205 cells.

The pools were tested for activity using the same caspase assay described in Example 4. From this testing, 48 potential positive pools were identified, and these were expanded and retested for caspase activity in duplicate. Two pools with the highest caspase activity were identified. Genomic DNA was isolated from these and used to generate a PCR fragment comprising the scFv-encoding region that had been originally introduced via transfection. This fragment was introduced into a high expression vector in which the scFv-encoding region was linked in frame to an Fc region (encoding a soluble scFv-Fc) or into a high expression vector in which the scFv-encoding region was linked in frame to an Fc region and a transmembrane domain (encoding a cell surface scFv-Fc). *E. coli* transformants were generated. Plasmid DNA from single colonies was used to transfect Cos1 cells. Transfectants expressing cell surface antibodies and soluble antibodies produced by Cos1 transfectants were tested for their ability to inhibit the proliferation of Colo205 cells. For soluble scFv-Fcs, the culture medium in which the transfected Cos1 cells were grown, containing soluble antibodies, was used to perform the assay. Colo205 cells were combined with the culture medium or with the Cos1 cells expressing cell surface antibodies and incubated for 24 hours before adding 2 μCi of $^3$H-thymidine and incubating an additional 24 hours. Cells were harvested, washed, and counted to determine how much radioactivity they had incorporated. FIG. 13 shows the results obtained from individual soluble antibodies generated from the highest scoring original pool. Results using cell surface scFv-Fcs were similar. Colo205 cells incubated with medium from mock-transfected Cos1 cells (labeled "mock") incorporated almost 350,000 cpm, whereas medium from cells transfected with the positive control, TRAIL-R2 antibody, incorporated less than 50,000 cpm. Two wells incorporated less than about 100,000 cpm (C10 and E9), and three others incorporated less than about 150,000 cpm (B8, C1, and C9). Thus, the methods of the invention can be used to identify soluble antibodies that can inhibit proliferation of Colo205 cells.

EXAMPLE 6

Use of Mammalian Display of Antibodies and FACS to Enrich for Mammalian Cells Expressing an Antibody that Binds to a Known Antigen The following experiment was designed to determine whether mammalian display of antibodies can be used to enrich for antibodies that bind to a specific, known antigen. Two expression vectors were constructed so as to express two different antibodies binding to different antigens, which both contain human IgG Fc regions and are designated antibody A and antibody B. The vectors were transfected into CHO cells containing a single FRT site (FCHO) to form two cell populations, one expressing each of the antibodies. These two cell populations were mixed in a ratio of 1 (expressing antibody A) to 1000 (expressing antibody B). The cell mixture was stained with a fluorescently-labeled antigen bound by antibody A plus a fluorescently-labeled antibody that binds to a human IgG Fc region and subjected to a first FACS analysis. Cells staining with both labeled molecules were sorted out, cultured for five days and subjected to a second FACS analysis to determine whether the proportion of cells binding to the antigen bound by antibody A had increased.

Figure 14:
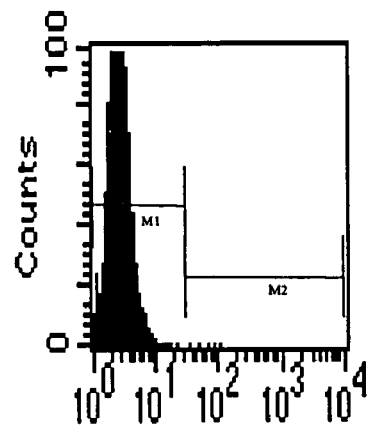
FIG. 14: The graph at upper left shows a FACS analysis of a 1000:1 mixture of CHO cells containing a single FRT site (FCHO cells) transfected with nucleic acids encoding antibody B and antibody A, respectively, stained with the target protein for antibody A. At upper right the percentage of cells within the two populations (M1 and M2) within the gated regions of the FACS analysis at upper left are shown, as well as the mean fluorescence within each population. At lower left is a similar FACS analysis of cells within the M2 region from above after five days of culture. At lower right is shown the percentage of cells within the gated regions of the FACS analysis at lower left, as well as the mean fluorescence within each region.
Figure 14:
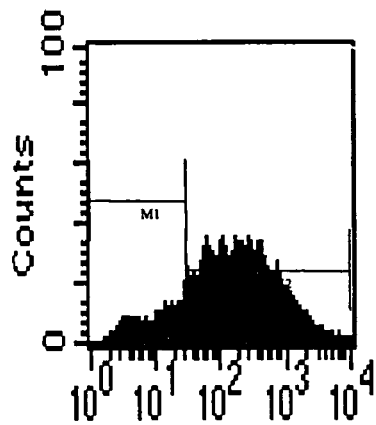

A relevant portion of the results is shown in FIG. 14. The upper left panel of FIG. 14 shows the first FACS analysis, depicting only fluorescence due to the antigen bound by antibody A. As expected, the vast majority of cells do not bind to the antigen bound by antibody A. The upper right portion of FIG. 14 shows the percentages of cells within the gated regions, M1 (99.94%) and M2 (0.06%), and the mean fluorescence of the cells within each region. These results indicated that slightly less than one in a thousand cells could bind to the antigen bound by antibody A at this stage, which is consistent with expectations given the input ratio of antibody A- to antibody B-expressing cells. Cells within the M2 region (which bound the antibody A antigen) were sorted out, cultured for five days, and then re-analyzed by FACS. The lower left portion of FIG. 14 shows the fluorescence due to the antigen bound by antibody A in this second FACS analysis, and the lower right portion of FIG. 14 shows percentages of cells within the gated regions, M1 and M2. These data indicate that more than 80% of the cells could bind to the antigen bound by antibody A, a substantial enrichment when compared to the 0.06% detected in the first FACS analysis. Thus, these results demonstrate that it is possible to use mammalian display of antibodies in conjunction with FACS to enrich for cells expressing an antibody that binds to a known antigen.

EXAMPLE 7

Conversion of Phage-Displayed Fab Fragments into Full Length Antibodies Displayed on the Surface of Mammalian Cells This example shows how antibody fragments selected from a phage antibody library can be converted to full length antibodies displayed on the surface of mammalian cells, a format in which they can be subjected to further selection as shown in Examples 6, 8, 9, and 10. Since full length antibodies produced in mammalian cells can be useful in some applications where antibody fragments are not and may have different binding properties than antibody fragments, it is useful to subject a full length antibody library to selection. Further, the heavy and light chain shuffling that occurs using the methods described in this example can lead to a greater diversity among the antibodies. Finally, this example provides evidence that each mammalian cell transfected using a FLP-IN™-type system expresses a single kind of antibody encoded by the transfecting DNA.

A phage-displayed human Fab library was panned with insulin-like growth factor receptor (IGF-1R), and phage expressing Fabs binding to IGF-R1 were isolated. Nucleic acids encoding heavy chain variable regions were amplified from the phage nucleic acids by PCR using the following primers: 5'-CAG CAG AAG CTT CTA GAC CAC CAT GCG TAC TCT GGC TAT CCT TG-3' and 5'-AAG ACC GAT GGG CCC TTG GTG-3'. These PCR products were inserted into a mammalian expression vector encoding heavy chain constant regions so as to form a complete heavy chain coding region. This material was used to generate a first set of *E. coli* transformants. Nucleic acids encoding light chain variable regions were amplified from the phage nucleic acids by PCR using the following primers: 5'-CAG CAG AAG CTT CTA GAC CAC CAT GAA AAT CCT GAT TCT CGG TAT CTT C-3' and 5'-CTT GTC GAC TCA ACA CTC TCC CCT GTT GAA GCT C-3'. These PCR products were inserted into a mammalian expression vector that encoded a light chain constant region so as to form a complete light chain coding region. This DNA was used to generate a second set of *E. coli* transformants. Variable region-encoding plasmid DNA from each of 91 individual transformants from each of these two sets of *E. coli* transformants was sequenced.

A library of full length antibodies was constructed as follows. Plasmid DNA comprising the 91 heavy chain coding regions was pooled, and the entire heavy chain coding region was amplified from this pool using the following two primers: 5'-CAG CAG AAG CTT CTA GAC CAC CAT GCG TAC TCT GGC TAT CCT TG-3' and 5'-TTA TCA GGA TCC TTT ACC CGG AGA CAG G-3'. Plasmid DNA comprising the 91 light chain-encoding regions was pooled, and the entire light chain coding region was amplified from this pool using the following two primers: 5'-CAG CAG ATC GAT AGA CCA CCA TGA AAA TCC TGA TTC TCG GTA TCT TC-3' and 5'-CTT CTT CTC GAG TCA ACA CTC TCC CCT GTT GAA GCT C-3'. In a first cloning step, the amplified heavy chain coding region was used to replace the unrelated heavy chain coding region in a vector like that shown in FIG. 3, thereby creating a library of about 91 different heavy chain coding regions and a single light chain coding region. In a second cloning step, the amplified light chain coding regions, were used to replace the unrelated light chain coding region present in the heavy chain library, thereby creating a library comprising about 91 different heavy chain and 91 different light chain coding regions. These two cloning steps created a full length antibody library in which the heavy and light chains present in the phage Fab library were shuffled into many new heavy and light chain combinations.

Mammalian cells genetically engineered to contain a single FRT site were transfected with this *E. coli* library of nucleic acids plus another vector encoding the FLP recombinase. The transfectants were analyzed by FACS, and cells that stained with both an anti-kappa antibody and IGF-1R were deposited into microtiter plate wells with one cell in each well. These cells were allowed to proliferate. The colonies of cells arising from a single cell were reanalyzed by FACS to ensure that the cells continued to stain with both anti-kappa antibody and IGF-1R. RNA from such colonies of cells was isolated, and the $V_H$ and $V_L$ regions were amplified by reverse transcription plus PCR (see e.g. Murphy et al. (1990), *Biochemistry* 29(45):10351-10356) using primers designed to amplify the variable region-encoding portions of the nucleic acids used for transfection. The primers used to do this were: heavy chain variable region, 5'-ACT TAA GCT TCG TCT CTA GTC CAC CAT GCG TAC TCT GGC TAT CCT TG-3' and 5'-ACC GAT GGG CCC TTG GTG CTA GCT GAG GAG ACG-3'; and light chain variable region, 5'-CAG CAG CCA CCT GAT TGG AGA CCA CCA TGA AAA TCC TGA TTC TCG GTA TCT TC-3' and 5'-CTT CTT CCA GAG TCA TGG TCA ACA CTC TCC CCT GTT GAA GCT C-3'. The PCR products were sequenced using the same primers used to amplify the variable regions. Sequence results from eight clonal cell colonies showed that a single kind of heavy chain and a single kind of light chain variable region was expressed in each colony of cells arising from a single transfectant. These data suggest that only one antibody gene was integrated into the genome via transfection and expressed in each of these transfectants.

EXAMPLE 8

The Use of Antibody Display on Mammalian Cells to Enrich for Neutralizing Antibodies In this example, the feasibility of using FACS to isolate mammalian cells expressing antibodies on their surfaces that can be displaced by the presence of a counterstructure of the antigen is demonstrated. Antibodies that can be displaced by a counterstructure are likely to inhibit the biological activity of the antigen and/or be neutralizing antibodies.

Figure 15:
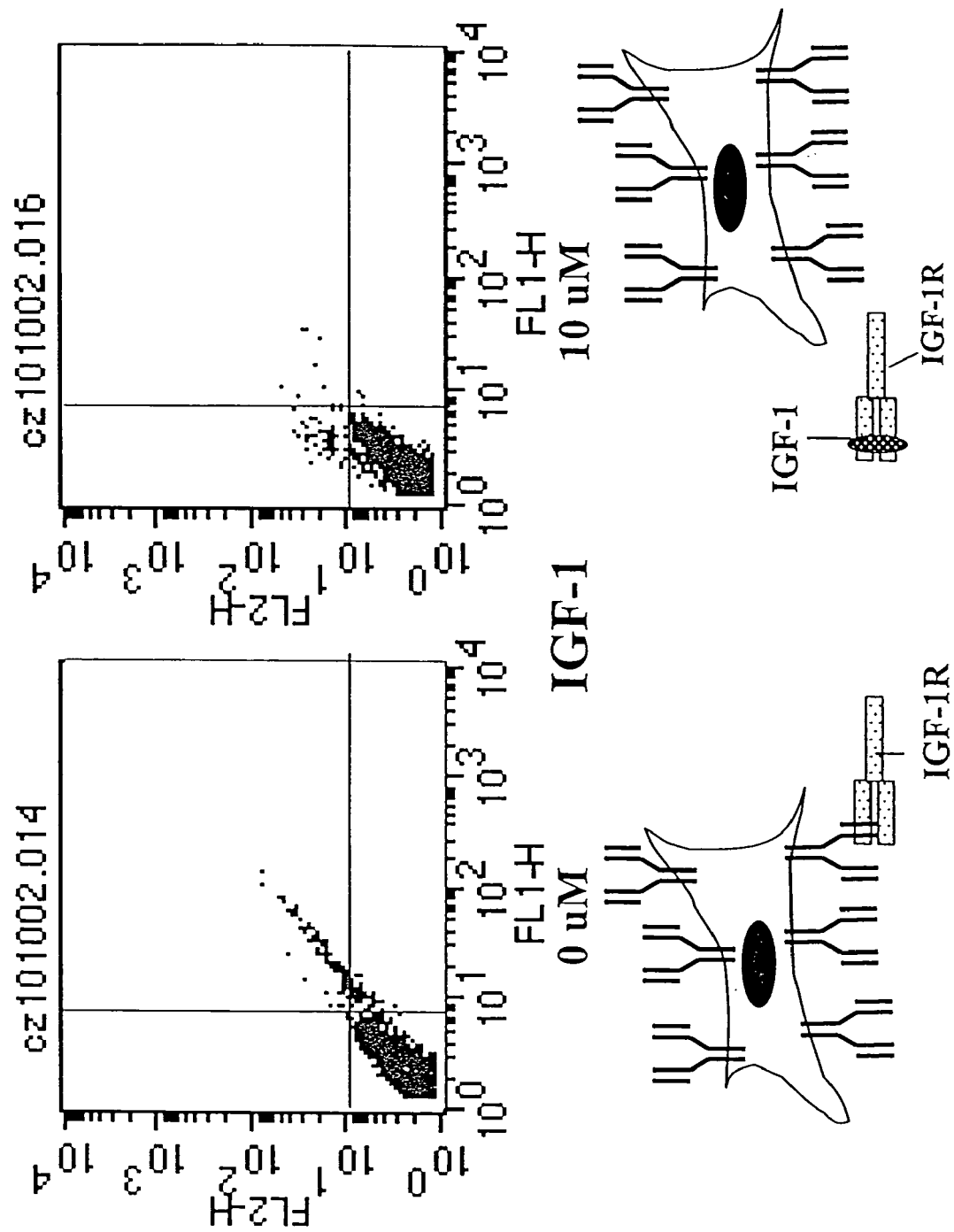
FIG. 15: The top two panels show the results of FACS analysis of cells expressing a full length cell surface antibody that binds to insulin like growth factor-1 receptor (IGF-1R) in the absence (left), but not in the presence (right), of insulin like growth factor-1 (IGF-1), as indicated. The horizontal axis represents fluorescence due to fluorescently-labeled IGF-1R. The vertical axis represents fluorescence due to a fluorescently-labeled antibody that binds to the kappa light chain. Below each panel are diagrammed cells expressing a full length antibody that binds to IGF-1R in the absence (left), but not in the presence (right) of IGF-1.

One transfected cell from Example 7 was subjected to further analysis by FACS to determine whether FACS could distinguish an antibody that could be displaced by a counterstructure from one that could not be displaced. This single transfected cell, which stained with both an anti-kappa antibody and with IGF-1R, was isolated using a FACS machine and allowed to proliferate. After 10 days of growth in a plate, the cells arising from this single transfectant were divided into two groups, one with and one without IGF-1. To mimic the situation that would be expected using a library, a majority of cells that did not bind to either the anti-kappa antibody or IGF-1R were added to both of the two groups of cells. FIG. 15 shows FACS analyses of these two groups of cells stained with an anti-kappa chain antibody (plus a fluorescently-labeled antibody that binds to it, vertical axis) and a fluorescently-labeled IGF-1R (horizontal axis), in the absence (left) and the presence (right) of IGF-1. In the absence of IGF-1, a diagonal smear extending from the lower left corner towards the middle of the square indicates that some cells (those that fall in the upper right quadrant) express proteins that bind to both the anti-kappa antibody and IGF-1R. In the presence of IGF-1, few cells bind to both IGF-1R and the anti-kappa antibody (upper right quadrant), and more cells bind to the anti-kappa antibody without binding to IGF-1R (upper left quadrant). These data indicate that the antibodies expressed by the single transfectant analyzed here can be displaced by IGF-1. Further, these results suggest that it is feasible to distinguish cells expressing antibodies that can be displaced by a counterstructure from those that cannot.

In a screening procedure to isolate cells expressing antibodies that can be displaced by a counterstructure, cells expressing antibodies that can, for example, bind to an anti-kappa antibody but not to the antigen in the presence of a counterstructure will be isolated by sequestering cells falling in the upper left quadrant of a FACS scan such as that on the right of FIG. 15. Then these cells will be allowed to proliferate and subjected to a second FACS analysis in the absence of the counterstructure, such as that shown on the left of FIG. 15, in which cells from the upper right quadrant will be sequestered. Such cells would be expected to be enriched for cells expressing antibodies that can bind to the antigen but are displaced by the counterstructure. The order of these FACS analyses could be reversed, and/or either of these analyses could be performed multiple times. The cells may or may not be allowed to proliferate between the FACS steps. Such a procedure can be used to screen for antibodies expressed on mammalian cells to enrich for cells expressing antibodies that bind to an antigen but can be displaced by its counterstructure. Such antibodies are likely to inhibit the biological activity of the antigen.

EXAMPLE 9

Selection of an Antibody with a Low Dissociation Constant

The following example shows that FACS analysis of mammalian cells expressing antibodies on their cell surface can distinguish antibodies with different dissociation constants. Three kinds of cells were combined in a ratio of about 500:498:2, respectively, cells binding to neither interferon gamma or an anti-kappa antibody, cells binding to an anti-κ chain antibody and to interferon gamma with an equilibrium dissociation constant of about 125 pM, and cells binding to an anti-κ chain antibody and to interferon gamma with an equilibrium dissociation constant of about 23 pM. Thus, the tighter-binding antibody was present as a minority species.

To adjust the FACS conditions so that differences in affinity could be detected, a series of FACS analyses was done using different concentrations of fluorescently-labeled interferon gamma mixed with cells displaying anti-interferon gamma antibodies. A plot of intensity of fluorescence versus interferon gamma concentration reveals a curve in which the intensity of fluorescence increases with increasing interferon gamma concentration up to a certain concentration, above which fluorescence intensity does not substantially increase. A concentration of interferon gamma that was about half of this concentration was chosen for this experiment.

Figure 16B:
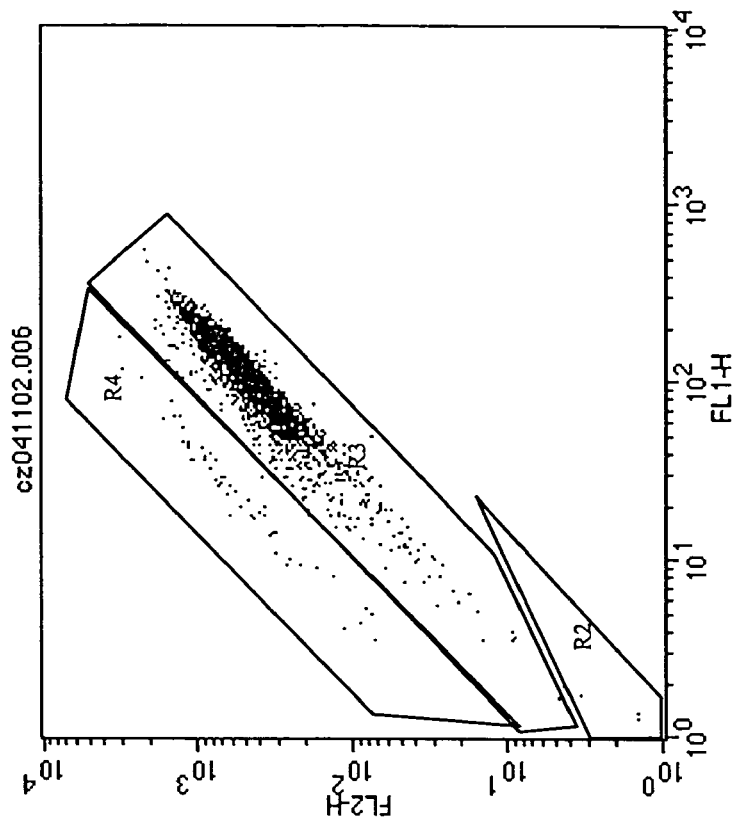
FIGS. 16A and 16B show the results of FACS analysis of cells transfected with a mixture of nucleic acids encoding two antibodies with different dissociation constants that bind to interferon gamma carried on a vector such that the full length antibodies are expressed on the cell surface. The horizontal axis represents fluorescence due to fluorescently-labeled interferon gamma. The vertical axis represents fluorescence due to a fluorescently-labeled antibody that binds to the kappa light chain of the antibody.
Figure 16A:
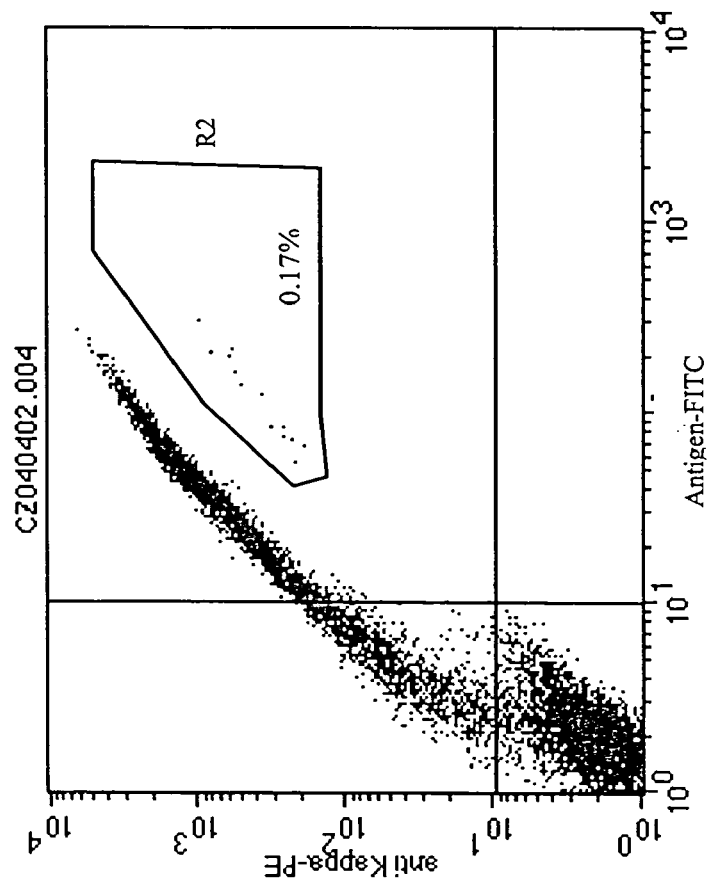

FIG. 16A shows a FACS analysis of this mixture of cells stained with an anti-kappa chain antibody (plus a fluorescently-labeled secondary antibody that binds to it, vertical axis) and fluorescently-labeled interferon gamma (horizontal axis). As expected, a small proportion of the cells show more intense fluorescence than the majority of cells and thus likely express the tighter binding antibody (boxed in the region labeled "R2"). The majority of cells show less intense fluorescence and thus probably express the other antibody. The cells falling into the "R2" area were sequestered as a pool and allowed to proliferate for about 5 days. Upon a second FACS analysis (FIG. 16B), the vast majority of these cells appeared to express the antibody with the lower dissociation constant. Thus, the method of the invention can be effective in enriching for cells expressing antibodies with higher or lower binding affinities, even those present as minority species. Using this method, one high affinity antibody to IGF-1R has been identified from the cell pool generated in the experiments described in Example 7. The sequence of this antibody was identical to the sequence of a high affinity antibody from the same pool of antibodies identified by converting the Fab fragments to full length antibodies individually and testing the antibodies individually for function.

EXAMPLE 10

The Use of Mammalian Display for Affinity Maturation

The following experiment was designed to determine whether mammalian display could be used to screen for antibody sequence variants having greater binding affinity than a starting antibody. The process of isolating such antibodies is referred to herein as "affinity maturation." Affinity maturation using phage display is described in, e.g. Schier et al. (1996), J. Mol. Biol. 263:551-567, Yang et al. (1995), J. Mol. Biol. 254:392-403, and Desiderio et al. (2001), J. Mol. Biol. 310: 603-615.

A full length antibody against OX40 ligand (OX40L) was chosen as the starting antibody. Amino acids at four positions within the heavy chain variable region, one within CDR1, one within CDR2, and two within CDR3, were selected for site-directed mutagenesis. PCR primers were designed so as to introduce mutations into the chosen codons, and PCR was carried out using a vector encoding the heavy chain variable region of the starting antibody as a template. The resulting PCR fragment, which encoded the entire heavy chain variable region, contained sequence variations within codons 33, 50, 96, and 97 (according to Kabat numbering system for the heavy chain variable region). Kabat et al., supra. The PCR fragment was inserted into an FRT-containing vector designed for high expression of full length antibodies in mammalian cells such that the vector with the inserted PCR fragment encoded a library of full length antibodies identical to the starting antibody except at positions 33, 50, 96, and 97. This DNA was introduced into E. coli by transformation. Plasmid DNA from a large pool of transformants was purified and used to transfect FCHO cells along with another vector containing nucleic acids encoding the FLP recombinase. FACS analysis indicated that the OX40L specific antibody was displayed on the cell surfaces of transfectants.

To enrich for transfectants expressing the highest affinity antibodies, sequential FACS sorting was carried out using a fluorescently-labeled OX40L and an anti-human kappa chain antibody. As in Example 9, the concentration of fluorescently-labeled antigen was adjusted such that it was about half the lowest concentration at which maximal labeling of the cells occurred. Starting with the original pool of transfectants, a gated window was set such that about 3% of the cells showing the greatest amount of fluorescence in the FACS analysis were sequestered. These cells were allowed to expand in culture for four days and were then subjected to a second FACS analysis, which showed that more than 40% of the cells were located in the window used in first sorting. A gated window was set such that about 5% of the cells showing the greatest fluorescence were sequestered. After expansion in culture, more than forty single cells that bound OX40L were isolated in a third FACS analysis. These cells were allowed to expand, and the resulting clonal cell lines were analyzed by FACS to determine whether they could bind to OX40L using a fluorescently labeled OX40L antibody and anti-human kappa chain antibody. Fourteen of these cell lines were selected for further analysis. The heavy chain variable regions of 12 of the 14 clones were amplified using RT-PCR and sequenced. These twelve cell lines expressed seven different heavy chain variable regions. One of the antibody coding regions had the starting antibody variable region-encoding sequence, and the other six expressed variant sequences.

DNA encoding the heavy chain variable region of each the six variant antibodies was inserted into an expression vector containing an FRT site designed to express full length, secreted, soluble heavy chains, and each of these DNAs were separately introduced into E. coli, and plasmid DNA was recovered from these transformants. FCHO cells were transfected with each of these heavy chain-encoding vectors plus a light chain-encoding vector. Conditioned medium from each transfected line was collected at 72 hours post transfection, and the binding activity to OX40L of each antibody contained in the conditioned medium was analyzed by testing for binding to AM-1/D cells, which overexpress OX40L on the cell surface, in a competition assay using OX40 as the competitor. Four of the six antibodies showed strong specific binding activity to OX40L expressed on the AM-1/D cell surface as measured by FACS. One of these four antibodies (#13) showed approximately a four-fold decrease in $EC_{50}$ (concentration needed for half of the maximal response) relative to the original antibody in a competition assay with OX40 for binding to OX40L. Data from this assay are shown in Table 3 below. Among the four variant antibodies tested, three (#7, #10, and #32) had higher $EC_{50}$'s than the original antibody, and one (#13) had a lower $EC_{50}$.

TABLE III

| Antibody | original | #7 | #10 | #13 | #32 |
|---|---|---|---|---|---|
| $EC_{50}(M)$ | $8.95 \times 10^{-10}$ | $8.53 \times 10^{-8}$ | $1.20 \times 10^{-9}$ | $2.01 \times 10^{-10}$ | $1.34 \times 10^{-9}$ |

These data show that the methods of the invention can be successfully used to directly isolate an antibody with enhanced binding characteristics compared to a starting antibody.

Similar experiments starting with a different original antibody, in which 13 positions within the DNA encoding the heavy chain variable region were varied, yielded several antibodies with lower $K_D$ values (by as much as about eight fold) and higher biological activity than the starting antibody.

What is claimed is:

1. A method for enriching for variant antibodies that bind to a molecule with different affinity than does an original antibody that binds to the molecule comprising the steps of:
   (a) providing a library of nucleic acids that encodes about 100 or more different variant antibodies, each having a variant antibody amino acid sequence, wherein the variant antibody amino acid sequences are identical to an original antibody amino acid sequence, except that they differ from the original antibody amino acid sequence at one or more selected sites within one or more complementarity determining regions, wherein the variant antibody amino acid sequences comprise an amino-terminal signal sequence in their immature form, wherein the library encodes variant antibodies including a membrane association sequence downstream from the variant antibody amino acid sequence, and wherein the variant antibodies can be expressed from the library of nucleic acids as cell surface antibodies in mammalian cells;
   (b) transfecting the library of nucleic acids into mammalian cells, thereby enabling the mammalian cells to express the variant antibodies as cell surface proteins; and
   (c) isolating cells that express variant antibodies that bind to the molecule with different affinity than do cells expressing the original antibody,
   wherein most of the individual mammalian cells expressing the variant antibodies express only variant antibodies having a single sequence, and
   wherein the mammalian cells comprise a FLP recombination target (FRT) site and the library of nucleic acids comprises an FRT site.

2. The method of claim 1, wherein the isolated cells express variant antibodies that bind to the molecule with higher affinity than do cells expressing the original antibody.

3. The method of claim 1, wherein the cells of (c) are isolated using fluorescence activated cell sorting.

4. The method of claim 1, wherein the original antibody and the variant antibodies comprise an Fc region.

5. The method of claim 4, wherein the original antibody and the variant antibodies are full length antibodies.

* * * * *